US012233106B2

(12) United States Patent
Day et al.

(10) Patent No.: US 12,233,106 B2
(45) Date of Patent: Feb. 25, 2025

(54) C-TYPE NATRIURETIC PEPTIDE VARIANTS TO TREAT SKELETAL DYSPLASIA IN CHILDREN

(71) Applicant: BIOMARIN PHARMACEUTICAL INC., Novato, CA (US)

(72) Inventors: Jonathan Day, Buckinghamshire (GB); Elena Fisheleva, Novato, CA (US)

(73) Assignee: BIOMARIN PHARMACEUTICAL INC., Novato, CA (US)

(*) Notice: Subject to any disclaimer, the term of this patent is extended or adjusted under 35 U.S.C. 154(b) by 0 days.

(21) Appl. No.: 17/811,748

(22) Filed: Jul. 11, 2022

(65) Prior Publication Data

US 2023/0140311 A1 May 4, 2023

Related U.S. Application Data

(60) Provisional application No. 63/350,196, filed on Jun. 8, 2022, provisional application No. 63/220,275, filed on Jul. 9, 2021.

(51) Int. Cl.

| | |
|---|---|
| *A61K 38/22* | (2006.01) |
| *A61K 9/00* | (2006.01) |
| *A61K 9/19* | (2006.01) |
| *A61K 38/00* | (2006.01) |
| *A61K 38/17* | (2006.01) |
| *A61K 47/10* | (2017.01) |
| *A61K 47/12* | (2006.01) |
| *A61K 47/18* | (2017.01) |
| *A61P 19/08* | (2006.01) |
| *C07K 7/00* | (2006.01) |
| *C07K 14/00* | (2006.01) |

(52) U.S. Cl.
CPC ........ *A61K 38/2242* (2013.01); *A61K 9/0019* (2013.01); *A61K 38/1709* (2013.01); *A61K 47/10* (2013.01); *A61K 47/12* (2013.01); *A61K 47/183* (2013.01); *A61K 9/19* (2013.01)

(58) Field of Classification Search
CPC .... A61K 38/2242; A61K 38/22; A61K 38/00; A61K 9/0019; A61K 38/1709; A61K 47/10; A61K 47/12; A61K 47/183; A61K 9/19; A61P 19/08; C07K 7/00; C07K 14/00
See application file for complete search history.

(56) References Cited

U.S. PATENT DOCUMENTS

| | | | |
|---|---|---|---|
| 5,352,770 A | 10/1994 | Matsuo | |
| 6,034,231 A | 3/2000 | Tanaka et al. | |
| 7,276,481 B2 | 10/2007 | Golembo et al. | |
| 7,642,243 B2 | 1/2010 | Nakao et al. | |
| 8,198,242 B2 | 6/2012 | Wendt et al. | |
| 8,377,884 B2 | 2/2013 | Wendt et al. | |
| 8,598,121 B2 | 12/2013 | Wendt et al. | |
| 8,658,373 B2 | 2/2014 | Nakao et al. | |
| 9,907,834 B2 | 3/2018 | Bullens et al. | |
| 10,646,550 B2 | 5/2020 | Bullens et al. | |

FOREIGN PATENT DOCUMENTS

| | | |
|---|---|---|
| WO | 94/20534 A1 | 9/1994 |
| WO | 2009/067639 A2 | 5/2009 |
| WO | 2010/135541 A2 | 11/2010 |
| WO | 2021/030411 A1 | 2/2021 |
| WO | 2021/055497 A1 | 3/2021 |

OTHER PUBLICATIONS

Alfonzo et al., Characterization of a G protein-coupled guanylyl cyclase-B receptor from bovine tracheal smooth muscle, J. Recept. Signal. Transduct. Res., 26:269-297 (2006).
Altschul et al., Basic local alignment search tool, J. Mol. Biol., 215(3):403-410 (1990).
Bartels et al., Mutations in the transmembrane natriuretic peptide receptor NPR-B impair skeletal growth and cause acromesomelic dysplasia, type Maroteaux, Am. J. Hum. Genet., 75:27-34 (2004).
Bellus et al., Hypochondroplasia: molecular analysis of the fibroblast growth factor receptor 3 gene, Ann. N.Y. Acad. Sci., 785:182-187 (1996).
Chen et al., Next-generation sequencing identifies rare variants associated with Noonan syndrome, Proc. Natl. Acad. Sci. USA, 111(31):11473-8 (2014).
Coffin et al., Abnormal bone growth and selective translational regulation in basic fibroblast growth factor (FGF-2) transgenic mice, Mol. Biol. Cell., 6:1861-73 (1995).
Colvin et al., Skeletal overgrowth and deafness in mice lacking fibroblast growth factor receptor 3, Nature Genet., 12:390-397 (1996).
Feng et al., Progressive sequence alignment as a prerequisite to correct phylogenetic trees, J. Mol. Evol., 25:351-360 (1987).
Gardner et al., Molecular biology of the natriuretic peptide system: implications for physiology and hypertension, Hypertension, 49:419-426 (2007).
GenBank: Accession No. NP_002512: natriuretic peptides B preproprotein [*Homo sapiens*], dated Nov. 27, 2022.
GenBank: Accession No. NP_006163: natriuretic peptides A preproprotein [*Homo sapiens*], dated Dec. 27, 2022.
GenBank: Accession No. NP_077720: C-type natriuretic peptide preproprotein [*Homo sapiens*], dated Dec. 18, 2022.
Henikoff et al., Amino acid substitution matrices from protein blocks, Proc. Natl. Acad. Sci. USA., 89:10915-10919 (1992).
Higgins et al., Fast and sensitive multiple sequence alignments on a microcomputer, Comp. Appl. Biosci., 5:151-153 (1989).
Hunt et al., Bioactivity and metabolism of C-type natriuretic peptide in normal man, J. Clin. Endocrinol. Metab., 78:1428-35 (1994).

(Continued)

*Primary Examiner* — Julie Ha
(74) *Attorney, Agent, or Firm* — MARSHALL, GERSTEIN & BORUN LLP

(57) ABSTRACT treatment of skeletal dysplasias in children, and improvement in one or more symptoms of skeletal dysplasias, such as long bone growth or growth velocity, by administering variants of C-type natriuretic peptide (CNP) is described.

14 Claims, 4 Drawing Sheets

Specification includes a Sequence Listing.

(56) References Cited

OTHER PUBLICATIONS

International Application No. PCT/US2022/073605, International Search Report and Written Opinion, mailed Dec. 15, 2022.
Karlin et al., Applications and statistics for multiple high-scoring segments in molecular sequences, Proc. Natl. Acad. Sci. U.S.A., 90(12):5873-5877 (1993).
Kelly et al., Age-based reference ranges for annual height velocity in US children, J. Clin. Endocrinol. Metab., 99(6):2104-2112 (2014).
Kenny et al., Hydrolysis of human and pig brain natriuretic peptides, urodilatin, C-type natriuretic peptide and some C-receptor ligands by endopeptidase-24.11, Biochem. J., 291(Pt 1):83-88 (1993).
Koller et al., Selective activation of the B natriuretic peptide receptor by C-type natriuretic peptide (CNP), Science, 252:120-123 (1991).
Krejci et al., Interaction of fibroblast growth factor and C-natriuretic peptide signaling in regulation of chondrocyte proliferation and extracellular matrix homeostasis, J. Cell Sci., 118:5089-5100 (2005).
Lehninger, Biochemistry (Worth Publishers, Inc., 4th Edition, (2004).
Levin et al., Natriuretic Peptides, N. Engl. J. Med., 339: 321-328 (1998).
Maack et al., Physiological role of silent receptors of atrial natriuretic factor, Science, 238:675-678 (1987).
Milosavljevic et al., Two cases of RIT1 associated Noonan syndrome: Further delineation of the clinical phenotype and review of the literature, Am. J. Med Genet., 170(7):1874-80 (2016).
Nakao et al., Molecular biology and biochemistry of the natriuretic peptide system. I: Natriuretic peptides, J. Hypertens., 10:907-912 (1992).
Nakao et al., Molecular biology and biochemistry of the natriuretic peptide system. II: Natriuretic peptide receptors, J. Hypertens., 10:1111-1114 (1992).
Needleman et al., A general method applicable to the search for similarities in the amino acid sequence of two proteins, J. Mol. Biol., 48:443-53 (1970).
Olney et al., Heterozygous mutations in natriuretic peptide receptor-B (NPR2) are associated with short stature, J. Clin. Endocrinol. Metab., 91(4):1229-1232 (2006).
Olney, C-type natriuretic peptide in growth: a new paradigm, Growth Hormone & IGF Res., 16:S6-S14 (2006).
Pearson et al., Improved tools for biological sequence comparison, Proc. Natl. Acad. Sci. U.S.A., 85(8):2444-2448 (1988).
Remington'S Pharmaceutical Sciences, 18th Edition, pp. 1435-1712, Mack Publishing Co. (Easton, Pennsylvania (1990)).
Romano et al., Noonan syndrome: clinical features, diagnosis, and management guidelines, Pediatrics, 126(4):746-59 (2010).
Rousseau et al., Missense FGFR3 mutations create cysteine residues in thanatophoric dwarfism type I (TD1), Hum. Mol. Genet., 5:509-512 (1996).
Rousseau et al., Mutations in the gene encoding fibroblast growth factor receptor-3 in achondroplasia, Nature, 371:252-254 (1994).
Savarirayan et al., C-Type Natriuretic Peptide Analogue Therapy in Children with Achondroplasia, the N. Engl. J. Med., 381(1):25-35 (2019).
Savarirayan, et al., Once-daily, subcutaneous vosoritide therapy in children with achondroplasia: a randomised, double-blind, phase 3, placebo-controlled, multicentre trial, Lancet., 396(10252):684-692 (2020).
Shiang et al., Mutations in the transmembrane domain of FGFR3 cause the most common genetic form of dwarfism, achondroplasia, Cell, 78:335-342 (1994).
Smith et al., Comparison of biosequences, Adv. Appl. Math., 2:482-489 (1981).
Sudoh et al., C-type natriuretic peptide (CNP): a new member of natriuretic peptide family identified in porcine brain, Biochem. Biophys. Res. Commun., 168: 863-870 (1990).
Tajan et al., The RASopathy Family: Consequences of Germline Activation of the RAS/MAPK Pathway, Endocr. Rev., 39(5):676-700 (2018).
Tavormina et al., Thanatophoric dysplasia (types I and II) caused by distinct mutations in fibroblast growth factor receptor 3, Nat. Genet., 9:321-328 (1995).
Thomas et al., "Osteocrin, a Local Mediator of the Natriuretic System", J. Bone Miner. Res., vol. 19(S1), pp. S20, 1075 (Jan. 2004).
Thompson et al., CLUSTAL W: improving the sensitivity of progressive multiple sequence alignment through sequence weighting, position-specific gap penalties and weight matrix choice, Nucleic Acids Research, 22:4673-4680 (1994).
Wilkie et al., Functions of fibroblast growth factors and their receptors, Curr. Biol., 5:500-507 (1995).
Wu et al., "Furin-mediated Processing of Pro-C-type Natriuretic Peptide", J. Biol. Chem. 278: 25847-852 (2003).
Yamashita et al., Concentration of mRNA for the natriuretic peptide receptor-C in hypertrophic chondrocytes of the fetal mouse tibia, J. Biochem., 127:177-179 (2000).
Yeung et al., Binding of CNP-22 and CNP-53 to cultured mouse astrocytes and effects on cyclic GMP, Peptides, 17:101-106 (1996).

Figure 1

|  | Overall | | Cohort 1 | | Cohort 2 | | Cohort 3 | |
|---|---|---|---|---|---|---|---|---|
|  | Vosoritide (N=32) | Placebo (N=32) | Vosoritide (N=15) | Placebo (N=16) | Vosoritide (N=8) | Placebo (N=8) | Vosoritide (N=9) | Placebo (N=8) |
| Age on Day 1, Months | | | | | | | | |
| Mean (SD) | 24.39 (16.83) | 27.82 (19.25) | 39.62 (10.11) | 44.33 (11.54) | 17.00 (5.79) | 16.87 (6.21) | 5.56 (0.44) | 5.76 (0.59) |
| Median | 23.29 | 26.43 | 36.86 | 40.39 | 17.92 | 18.56 | 5.78 | 5.91 |
| Q1, Q3 | 5.93, 36.58 | 7.67, 40.39 | 30.19, 49.38 | 34.55, 56.36 | 11.50, 22.52 | 10.46, 22.16 | 5.32, 5.88 | 5.72, 5.95 |
| Sex, n(%) | | | | | | | | |
| Male | 17 (53.1) | 13 (40.6) | 7 (46.7) | 7 (43.8) | 5 (62.5) | 5 (62.5) | 5 (55.6) | 1 (12.5) |
| Female | 15 (46.9) | 19 (59.4) | 8 (53.3) | 9 (56.3) | 3 (37.5) | 3 (37.5) | 4 (44.4) | 7 (87.5) |
| Race* | | | | | | | | |
| White | 21 (65.6) | 25 (78.1) | 8 (53.3) | 13 (81.3) | 6 (75.0) | 6 (75.0) | 7 (77.8) | 6 (75.0) |
| Asian | 10 (31.3) | 6 (18.8) | 6 (40.0) | 3 (18.8) | 2 (25.0) | 1 (12.5) | 2 (22.2) | 2 (25.0) |
| Japanese | 4 (12.5) | 4 (12.5) | 2 (13.3) | 3 (18.8) | 1 (12.5) | 1 (12.5) | 1 (11.1) | 0 |

Cohort 1: Ages 24 to <60 months
Cohort 2: Ages 6 to <24 months
Cohort 3: Ages 0 to <6 months Cohort 1: Ages 24 to <60 months
Cohort 2: Ages 6 to <24 months
Cohort 3: Ages 0 to <6 months Cohort 1: Ages 24 to <60 months
Cohort 2: Ages 6 to <24 months
Cohort 3: Ages 0 to <6 months

```
                            SEQUENCE LISTING

Sequence total quantity: 68
SEQ ID NO: 1            moltype = AA  length = 39
FEATURE                 Location/Qualifiers
source                  1..39
                        mol_type = protein
                        organism = synthetic construct
SEQUENCE: 1
PGQEHPNARK YKGANKKGLS KGCFGLKLDR IGSMSGLGC                            39

SEQ ID NO: 2            moltype = AA  length = 54
FEATURE                 Location/Qualifiers
source                  1..54
                        mol_type = protein
                        organism = synthetic construct
SEQUENCE: 2
GDLRVDTKSR AAWARLLQEH PNARKYKGAN KKGLSKGCFG LKLDRIGSMS GLGC           54

SEQ ID NO: 3            moltype = AA  length = 54
FEATURE                 Location/Qualifiers
source                  1..54
                        mol_type = protein
                        organism = synthetic construct
SEQUENCE: 3
PDLRVDTKSR AAWARLLQEH PNARKYKGAN KKGLSKGCFG LKLDRIGSMS GLGC           54

SEQ ID NO: 4            moltype = AA  length = 54
FEATURE                 Location/Qualifiers
source                  1..54
                        mol_type = protein
                        organism = synthetic construct
SEQUENCE: 4
MDLRVDTKSR AAWARLLQEH PNARKYKGAN KKGLSKGCFG LKLDRIGSMS GLGC           54

SEQ ID NO: 5            moltype = AA  length = 53
FEATURE                 Location/Qualifiers
source                  1..53
                        mol_type = protein
                        organism = synthetic construct
SEQUENCE: 5
DLRVDTKSRA AWARLLQEHP NARKYKGANK KGLSKGCFGL KLDRIGSNSG LGC            53

SEQ ID NO: 6            moltype = AA  length = 52
FEATURE                 Location/Qualifiers
source                  1..52
                        mol_type = protein
                        organism = synthetic construct
SEQUENCE: 6
LRVDTKSRAA WARLLQEHPN ARKYKGANKK GLSKGCFGLK LDRIGSMSGL GC             52

SEQ ID NO: 7            moltype = AA  length = 51
FEATURE                 Location/Qualifiers
source                  1..51
                        mol_type = protein
                        organism = synthetic construct
SEQUENCE: 7
RVDTKSRAAW ARLLQEHPNA RKYKGANKKG LSKGCFGLKL DRIGSMSGLG C              51
```

```
SEQ ID NO: 8              moltype = AA  length = 50
FEATURE                   Location/Qualifiers
source                    1..50
                          mol_type = protein
                          organism = synthetic construct
SEQUENCE: 8
VDTKSRAAWA RLLQEHPNAR KYKGANKKGL SKGCFGLKLD RIGSMSGLGC                 50

SEQ ID NO: 9              moltype = AA  length = 49
FEATURE                   Location/Qualifiers
source                    1..49
                          mol_type = protein
                          organism = synthetic construct
SEQUENCE: 9
DTKSRAAWAR LLQEHPNARK YKGANKKGLS KGCFGLKLDR IGSMSGLGC                   49

SEQ ID NO: 10             moltype = AA  length = 48
FEATURE                   Location/Qualifiers
source                    1..48
                          mol_type = protein
                          organism = synthetic construct
SEQUENCE: 10
TKSRAAWARL LQEHPNARKY KGANKKGLSK GCFGLKLDRI GSMSGLGC                    48

SEQ ID NO: 11             moltype = AA  length = 47
FEATURE                   Location/Qualifiers
source                    1..47
                          mol_type = protein
                          organism = synthetic construct
SEQUENCE: 11
KSRAAWARLL QEHPNARKYK GANKKGLSKG CFGLKLDRIG SMSGLGC                     47

SEQ ID NO: 12             moltype = AA  length = 46
FEATURE                   Location/Qualifiers
source                    1..46
                          mol_type = protein
                          organism = synthetic construct
SEQUENCE: 12
SRAAWARLLQ EHPNARKYKG ANKKGLSKGC FGLKLDRIGS MSGLGC                      46

SEQ ID NO: 13             moltype = AA  length = 45
FEATURE                   Location/Qualifiers
source                    1..45
                          mol_type = protein
                          organism = synthetic construct
SEQUENCE: 13
RAAWARLLQE HPNARKYKGA NKKGLSKGCF GLKLDRIGSM SGLGC                       45

SEQ ID NO: 14             moltype = AA  length = 44
FEATURE                   Location/Qualifiers
source                    1..44
                          mol_type = protein
                          organism = synthetic construct
SEQUENCE: 14
AAWARLLQEH PNARKYKGAN KKGLSKGCFG LKLDRIGSMS GLGC                        44

SEQ ID NO: 15             moltype = AA  length = 43
FEATURE                   Location/Qualifiers
source                    1..43
                          mol_type = protein
                          organism = synthetic construct
SEQUENCE: 15
AWARLLQEHP NARKYKGANK KGLSKGCFGL KLDRIGSMSG LGC                         43

SEQ ID NO: 16             moltype = AA  length = 42
FEATURE                   Location/Qualifiers
source                    1..42
                          mol_type = protein
                          organism = synthetic construct
SEQUENCE: 16
WARLLQEHPN ARKYKGANKK GLSKGCFGLK LDRIGSMSGL GC                          42

SEQ ID NO: 17             moltype = AA  length = 41
FEATURE                   Location/Qualifiers
source                    1..41
                          mol_type = protein
                          organism = synthetic construct
SEQUENCE: 17
```

```
ARLLQEHPNA RKYKGANKKG LSKGCFGLKL DRIGSMSGLG C                    41

SEQ ID NO: 18           moltype = AA   length = 40
FEATURE                 Location/Qualifiers
source                  1..40
                        mol_type = protein
                        organism = synthetic construct
SEQUENCE: 18
RLLQEHPNAR KYKGANKKGL SKGCFGLKLD RIGSMSGLGC                      40

SEQ ID NO: 19           moltype = AA   length = 39
FEATURE                 Location/Qualifiers
source                  1..39
                        mol_type = protein
                        organism = synthetic construct
SEQUENCE: 19
LLQEHPNARK YKGANKKGLS KGCFGLKLDR IGSMSGLGC                       39

SEQ ID NO: 20           moltype = AA   length = 38
FEATURE                 Location/Qualifiers
source                  1..38
                        mol_type = protein
                        organism = synthetic construct
SEQUENCE: 20
LQEHPNARKY KGANKKGLSK GCFGLKLDRI GSMSGLGC                        38

SEQ ID NO: 21           moltype = AA   length = 37
FEATURE                 Location/Qualifiers
source                  1..37
                        mol_type = protein
                        organism = synthetic construct
SEQUENCE: 21
QEHPNARYK GANKKGLSKG CFGLKLDRIG SMSGLGC                          37

SEQ ID NO: 22           moltype = AA   length = 36
FEATURE                 Location/Qualifiers
source                  1..36
                        mol_type = protein
                        organism = synthetic construct
SEQUENCE: 22
EHPNARYKG ANKKGLSKGC FGLKLDRIGS MSGLGC                           36

SEQ ID NO: 23           moltype = AA   length = 35
FEATURE                 Location/Qualifiers
source                  1..35
                        mol_type = protein
                        organism = synthetic construct
SEQUENCE: 23
HPNARYKGA NKKGLSKGCF GLKLDRIGSM SGLGC                            35

SEQ ID NO: 24           moltype = AA   length = 34
FEATURE                 Location/Qualifiers
source                  1..34
                        mol_type = protein
                        organism = synthetic construct
SEQUENCE: 24
PNARKYKGAN KKGLSKGCFG LKLDRIGSMS GLGC                            34

SEQ ID NO: 25           moltype = AA   length = 33
FEATURE                 Location/Qualifiers
source                  1..33
                        mol_type = protein
                        organism = synthetic construct
SEQUENCE: 25
NARKYKGANK KGLSKGCFGL KLDRIGSMSG LGC                             33

SEQ ID NO: 26           moltype = AA   length = 32
FEATURE                 Location/Qualifiers
source                  1..32
                        mol_type = protein
                        organism = synthetic construct
SEQUENCE: 26
ARKYKGANKK GLSKGCFGLK LDRIGSMSGL GC                              32

SEQ ID NO: 27           moltype = AA   length = 31
FEATURE                 Location/Qualifiers
source                  1..31
                        mol_type = protein
                        organism = synthetic construct
```

```
SEQUENCE: 27
RKYKGANKKG LSKGCFGLKL DRIGSMSGLG C                                    31

SEQ ID NO: 28           moltype = AA  length = 30
FEATURE                 Location/Qualifiers
source                  1..30
                        mol_type = protein
                        organism = synthetic construct
SEQUENCE: 28
KYKGANKKGL SKGCFGLKLD RIGSMSGLGC                                      30

SEQ ID NO: 29           moltype = AA  length = 29
FEATURE                 Location/Qualifiers
source                  1..29
                        mol_type = protein
                        organism = synthetic construct
SEQUENCE: 29
YKGANKKGLS KGCFGLKLDR IGSMSGLGC                                       29

SEQ ID NO: 30           moltype = AA  length = 28
FEATURE                 Location/Qualifiers
source                  1..28
                        mol_type = protein
                        organism = synthetic construct
SEQUENCE: 30
KGANKKGLSK GCFGLKLDRI GSMSGLGC                                        28

SEQ ID NO: 31           moltype = AA  length = 27
FEATURE                 Location/Qualifiers
source                  1..27
                        mol_type = protein
                        organism = synthetic construct
SEQUENCE: 31
GANKKGLSKG CFGLKLDRIG SMSGLGC                                         27

SEQ ID NO: 32           moltype = AA  length = 26
FEATURE                 Location/Qualifiers
source                  1..26
                        mol_type = protein
                        organism = synthetic construct
SEQUENCE: 32
ANKKGLSKGC FGLKLDRIGS MSGLGC                                          26

SEQ ID NO: 33           moltype = AA  length = 25
FEATURE                 Location/Qualifiers
source                  1..25
                        mol_type = protein
                        organism = synthetic construct
SEQUENCE: 33
NKKGLSKGCF GLKLDRIGSM SGLGC                                           25

SEQ ID NO: 34           moltype = AA  length = 24
FEATURE                 Location/Qualifiers
source                  1..24
                        mol_type = protein
                        organism = synthetic construct
SEQUENCE: 34
KKGLSKGCFG LKLDRIGSMS GLGC                                            24

SEQ ID NO: 35           moltype = AA  length = 23
FEATURE                 Location/Qualifiers
source                  1..23
                        mol_type = protein
                        organism = synthetic construct
SEQUENCE: 35
KGLSKGCFGL KLDRIGSMSG LGC                                             23

SEQ ID NO: 36           moltype = AA  length = 21
FEATURE                 Location/Qualifiers
source                  1..21
                        mol_type = protein
                        organism = synthetic construct
SEQUENCE: 36
LSKGCFGLKL DRIGSMSGLG C                                               21

SEQ ID NO: 37           moltype = AA  length = 20
FEATURE                 Location/Qualifiers
source                  1..20
                        mol_type = protein
```

```
                                organism = synthetic construct
SEQUENCE: 37
SKGCFGLKLD RIGSMSGLGC                                                            20

SEQ ID NO: 38           moltype = AA  length = 19
FEATURE                 Location/Qualifiers
source                  1..19
                        mol_type = protein
                        organism = synthetic construct
SEQUENCE: 38
KGCFGLKLDR IGSMSGLGC                                                             19

SEQ ID NO: 39           moltype = AA  length = 18
FEATURE                 Location/Qualifiers
source                  1..18
                        mol_type = protein
                        organism = synthetic construct
SEQUENCE: 39
GCFGLKLDRI GSMSGLGC                                                              18

SEQ ID NO: 40           moltype = AA  length = 37
FEATURE                 Location/Qualifiers
source                  1..37
                        mol_type = protein
                        organism = synthetic construct
SEQUENCE: 40
QEHPNARKYK GANKKGLSKG CFGLKLDRIG SNSGLGC                                         37

SEQ ID NO: 41           moltype = AA  length = 38
FEATURE                 Location/Qualifiers
source                  1..38
                        mol_type = protein
                        organism = synthetic construct
SEQUENCE: 41
PQEHPNARKY KGANKKGLSK GCFGLKLDRI GSMSGLGC                                        38

SEQ ID NO: 42           moltype = AA  length = 38
FEATURE                 Location/Qualifiers
source                  1..38
                        mol_type = protein
                        organism = synthetic construct
SEQUENCE: 42
MQEHPNARKY KGANKKGLSK GCFGLKLDRI GSMSGLGC                                        38

SEQ ID NO: 43           moltype = AA  length = 38
FEATURE                 Location/Qualifiers
source                  1..38
                        mol_type = protein
                        organism = synthetic construct
SEQUENCE: 43
GQEHPNARKY KGANKKGLSK GCFGLKLDRI GSMSGLGC                                        38

SEQ ID NO: 44           moltype = AA  length = 38
FEATURE                 Location/Qualifiers
source                  1..38
                        mol_type = protein
                        organism = synthetic construct
SEQUENCE: 44
GQEHPNARKY KGANKKGLSK GCFGLKLDRI GSNSGLGC                                        38

SEQ ID NO: 45           moltype = AA  length = 39
FEATURE                 Location/Qualifiers
source                  1..39
                        mol_type = protein
                        organism = synthetic construct
SEQUENCE: 45
MGQEHPNARK YKGANKKGLS KGCFGLKLDR IGSMSGLGC                                       39

SEQ ID NO: 46           moltype = AA  length = 38
FEATURE                 Location/Qualifiers
source                  1..38
                        mol_type = protein
                        organism = synthetic construct
SEQUENCE: 46
GHKSEVAHRF KGANKKGLSK GCFGLKLDRI GSMSGLGC                                        38

SEQ ID NO: 47           moltype = AA  length = 38
FEATURE                 Location/Qualifiers
source                  1..38
```

```
                           mol_type = protein
                           organism = synthetic construct
SEQUENCE: 47
GHKSEVAHRF KGANKKGLSK GCFGLKLDRI GSNSGLGC                                    38

SEQ ID NO: 48              moltype = AA    length = 39
FEATURE                    Location/Qualifiers
source                     1..39
                           mol_type = protein
                           organism = synthetic construct
SEQUENCE: 48
PGHKSEVAHR FKGANKKGLS KGCFGLKLDR IGSMSGLGC                                   39

SEQ ID NO: 49              moltype = AA    length = 39
FEATURE                    Location/Qualifiers
source                     1..39
                           mol_type = protein
                           organism = synthetic construct
SEQUENCE: 49
MGHKSEVAHR FKGANKKGLS KGCFGLKLDR IGSMSGLGC                                   39

SEQ ID NO: 50              moltype = AA    length = 27
FEATURE                    Location/Qualifiers
source                     1..27
                           mol_type = protein
                           organism = synthetic construct
SEQUENCE: 50
GANRRGLSRG CFGLKLDRIG SMSGLGC                                                27

SEQ ID NO: 51              moltype = AA    length = 27
FEATURE                    Location/Qualifiers
source                     1..27
                           mol_type = protein
                           organism = synthetic construct
SEQUENCE: 51
GANRRGLSRG CFGLKLDRIG SNSGLGC                                                27

SEQ ID NO: 52              moltype = AA    length = 28
FEATURE                    Location/Qualifiers
source                     1..28
                           mol_type = protein
                           organism = synthetic construct
SEQUENCE: 52
PGANRRGLSR GCFGLKLDRI GSMSGLGC                                               28

SEQ ID NO: 53              moltype = AA    length = 28
FEATURE                    Location/Qualifiers
source                     1..28
                           mol_type = protein
                           organism = synthetic construct
SEQUENCE: 53
MGANRRGLSR GCFGLKLDRI GSMSGLGC                                               28

SEQ ID NO: 54              moltype = AA    length = 27
FEATURE                    Location/Qualifiers
source                     1..27
                           mol_type = protein
                           organism = synthetic construct
MOD_RES                    1
                           note = PEG1K
SEQUENCE: 54
GANRRGLSRG CFGLKLDRIG SMSGLGC                                                27

SEQ ID NO: 55              moltype = AA    length = 27
FEATURE                    Location/Qualifiers
source                     1..27
                           mol_type = protein
                           organism = synthetic construct
MOD_RES                    1
                           note = PEG1K
SEQUENCE: 55
GANRRGLSRG CFGLKLDRIG SNSGLGC                                                27

SEQ ID NO: 56              moltype = AA    length = 28
FEATURE                    Location/Qualifiers
source                     1..28
                           mol_type = protein
                           organism = synthetic construct
MOD_RES                    1
```

```
                             note = PEG1K
SEQUENCE: 56
PGANRRGLSR GCFGLKLDRI GSMSGLGC                                       28

SEQ ID NO: 57            moltype = AA  length = 28
FEATURE                  Location/Qualifiers
source                   1..28
                         mol_type = protein
                         organism = synthetic construct
MOD_RES                  1
                         note = PEG1K
SEQUENCE: 57
MGANRRGLSR GCFGLKLDRI GSMSGLGC                                       28

SEQ ID NO: 58            moltype = AA  length = 27
FEATURE                  Location/Qualifiers
source                   1..27
                         mol_type = protein
                         organism = synthetic construct
MOD_RES                  1
                         note = PEO12
SEQUENCE: 58
GANRRGLSRG CFGLKLDRIG SMSGLGC                                        27

SEQ ID NO: 59            moltype = AA  length = 27
FEATURE                  Location/Qualifiers
source                   1..27
                         mol_type = protein
                         organism = synthetic construct
MOD_RES                  1
                         note = PEO12
SEQUENCE: 59
GANRRGLSRG CFGLKLDRIG SNSGLGC                                        27

SEQ ID NO: 60            moltype = AA  length = 28
FEATURE                  Location/Qualifiers
source                   1..28
                         mol_type = protein
                         organism = synthetic construct
MOD_RES                  1
                         note = PEO12
SEQUENCE: 60
PGANRRGLSR GCFGLKLDRI GSMSGLGC                                       28

SEQ ID NO: 61            moltype = AA  length = 28
FEATURE                  Location/Qualifiers
source                   1..28
                         mol_type = protein
                         organism = synthetic construct
MOD_RES                  1
                         note = PEO12
SEQUENCE: 61
MGANRRGLSR GCFGLKLDRI GSMSGLGC                                       28

SEQ ID NO: 62            moltype = AA  length = 27
FEATURE                  Location/Qualifiers
source                   1..27
                         mol_type = protein
                         organism = synthetic construct
MOD_RES                  1
                         note = PEO24
SEQUENCE: 62
GANRRGLSRG CFGLKLDRIG SMSGLGC                                        27

SEQ ID NO: 63            moltype = AA  length = 27
FEATURE                  Location/Qualifiers
source                   1..27
                         mol_type = protein
                         organism = synthetic construct
MOD_RES                  1
                         note = PEO24
SEQUENCE: 63
GANRRGLSRG CFGLKLDRIG SNSGLGC                                        27

SEQ ID NO: 64            moltype = AA  length = 28
FEATURE                  Location/Qualifiers
source                   1..28
                         mol_type = protein
                         organism = synthetic construct
```

```
MOD_RES              1
                     note = PEO24
SEQUENCE: 64
PGANRRGLSR GCFGLKLDRI GSMSGLGC                              28

SEQ ID NO: 65        moltype = AA  length = 28
FEATURE              Location/Qualifiers
source               1..28
                     mol_type = protein
                     organism = synthetic construct
MOD_RES              1
                     note = PEO24
SEQUENCE: 65
MGANRRGLSR GCFGLKLDRI GSMSGLGC                              28

SEQ ID NO: 66        moltype = AA  length = 39
FEATURE              Location/Qualifiers
source               1..39
                     mol_type = protein
                     organism = synthetic construct
SEQUENCE: 66
PGQEHPQARR YRGAQRRGLS RGCFGLKLDR IGSMSGLGC                  39

SEQ ID NO: 67        moltype = AA  length = 39
FEATURE              Location/Qualifiers
source               1..39
                     mol_type = protein
                     organism = synthetic construct
SEQUENCE: 67
PGQEHPNARR YRGANRRGLS RGCFGLKLDR IGSMSGLGC                  39

SEQ ID NO: 68        moltype = AA  length = 39
FEATURE              Location/Qualifiers
source               1..39
                     mol_type = protein
                     organism = synthetic construct
SEQUENCE: 68
PGQEHPQARK YKGAQKKGLS KGCFGLKLDR IGSMSGLGC                  39
```

C-TYPE NATRIURETIC PEPTIDE VARIANTS TO TREAT SKELETAL DYSPLASIA IN CHILDREN

CROSS-REFERENCE TO RELATED APPLICATIONS

The present application claims the priority benefit of U.S. Provisional Patent Application No. 63/220,275, filed Jul. 9, 2021 and U.S. Provisional Patent Application No. 63/350,196 filed Jun. 8, 2022, hereby incorporated by reference in their entireties.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "57038 SubSeqlisting.xml", which was created on Jan. 19, 2023 and is 66,072 bytes in size. The subject matter of the Sequence Listing is incorporated herein in its entirety by reference.

FIELD OF THE DISCLOSURE

The disclosure relates, in general, to the use of variants of C-type natriuretic peptide (CNP) to treat skeletal dysplasias in children.

BACKGROUND

The natriuretic peptide family consists of three structurally related peptides: atrial natriuretic peptide (ANP) (Genbank Accession No. NP_006163, for the ANP precursor protein, NPPA), brain natriuretic peptide (BNP) (GenBank Accession No. NP_002512, for the BNP precursor protein, NPPB), and C-type natriuretic peptide (CNP) (Biochem. Biophys. Res. Commun., 168: 863–870 (1990) (GenBank Accession No. NP_077720, for the CNP precursor protein, NPPC) (J. Hypertens., 10: 907–912 (1992)). These small, single chain peptides (ANP, BNP, CNP) have a 17-amino acid loop structure (Levin et al., N. Engl. J. Med., 339: 863–870 (1998)) and have important roles in multiple biological processes. ANP and BNP bind to and activate the natriuretic peptide receptor A (NPR-A), also termed guanalyl cyclase A (GC-A), resulting in higher intracellular cyclic guanosine monophosphate (cGMP) levels. Likewise, CNP interacts with NPR-B (GC-B) to stimulate the generation of cGMP (J. Hypertens., 10: 1111-1114 (1992)). A third type of receptor, NPR-C, binds each of the natriuretic peptides with high affinity and functions primarily to capture the peptides from the extracellular compartment and deposit the peptides into lysosomes, where they are degraded (Science, 238: 675–678 (1987)). ANP and BNP are produced primarily within the muscle cells of the heart, and are believed to have important roles in cardiovascular homeostasis (Science, 252: 120–123 (1991)). CNP is expressed more widely, including in the central nervous system, reproductive tract, bone and endothelium of blood vessels (Hypertension, 49: 419-426 (2007)).

In humans, CNP is initially produced from the natriuretic peptide precursor C (NPPC) gene as a single chain 126-amino acid pre-pro polypeptide (Biochem. Biophys. Res. Commun., 168: 863-870 (1990)). Removal of the signal peptide yields pro-CNP, and further cleavage by the endoprotease furin generates an active 53-amino acid peptide (CNP-53), which is secreted and cleaved again to produce the mature 22-amino acid peptide (CNP-22) (Wu, J. Biol. Chem. 278: 25847-852 (2003)). CNP-53 and CNP-22 differ in their distribution, with CNP-53 predominating in tissues, while CNP-22 is mainly found in plasma and cerebrospinal fluid (J. Alfonzo, Recept. Signal. Transduct. Res., 26: 269–297 (2006)). The predominant CNP form in cartilage is unknown. Both CNP-53 and CNP-22 bind similarly to NPR-B. Furthermore, they both induce cGMP production in a dose-dependent and similar fashion (VT Yeung, Peptides, 17: 101-106 (1996)).

Natural CNP genes and polypeptides have been previously described. U.S. Pat. No. 5,352,770 discloses isolated and purified CNP-22 from porcine brain identical in sequence to human CNP and its use in treating cardiovascular indications. U.S. Pat. No. 6,034,231 discloses the human gene and polypeptide of proCNP (126 amino acids) and the human CNP-53 gene and polypeptide.

Clearance of CNP from the extracellular space occurs through the action of membrane-bound neutral endopeptidase (NEP), which rapidly degrades CNP (Biochem. J., 291(Pt 1): 83-88 (1993)), and through NPR-C, which binds to and deposits CNP into lysosomes, where CNP is degraded. CNP has been shown to have an in vivo half-life of 2.6 min in the normal human (J. Clin. Endocrinol. Metab., 78: 1428-35 (1994)). The low plasma concentration of CNP (J. Bone Moner. Res., 19 (Suppl. 1)S20 (2004)) and its co-expression with NPR-B in a number of tissues suggests that CNP functions primarily through an autocrine/paracrine mechanism.

As stated above, CNP binds to and activates natriuretic peptide receptor B (NPR-B), also termed guanylyl cyclase B (GC-B), resulting in higher intracellular cyclic guanosine monophosphate (cGMP) levels. Downstream signaling mediated by cGMP generation influences a diverse array of biological processes that include endochondral ossification. Accordingly, elevated or depressed levels of any of the components in this pathway may lead to aberrant bone or cartilage growth. For example, knockout of either CNP or NPR-B in mouse models results in animals having a dwarfed phenotype with shorter long bones and vertebrae. Mutations in human NPR-B that block proper CNP signaling have been identified and result in dwarfism (Olney, et al., J. Clin. Endocrinol. Metab. 91(4): 1229-1232 (2006); Bartels, et al., Am. J. Hum. Genet. 75: 27-34 (2004)). In contrast, mice engineered to produce elevated levels of CNP display elongated long bones and vertebrae.

Achondroplasia is a result of an autosomal dominant mutation in the gene for fibroblast growth factor receptor 3 (FGFR-3), which causes an abnormality of cartilage formation. FGFR-3 normally has a negative regulatory effect on chondrocyte growth, and hence bone growth. In achondroplasia, the mutated form of FGFR-3 is constitutively active, which leads to severely shortened bones. Both chondrocyte proliferation and differentiation appear to be disturbed, leading to remarkably short growth plate cartilage (P. Krejci et al., J. Cell Sci. 118: 5089-5100 (2005)). Endochondral ossification is the process that governs longitudinal long-bone growth. There are four zones of the growth plate—resting, proliferative, hypertrophic and zone of calcification. In the growth plate, NPR-B is expressed by proliferative cells while NPR-C is expressed by hypertrophic cells (Yamashite et al., J. Biochem. 127: 177-179 (2000)). In normal endochondral bone growth, chondrocytes organize in columns and proliferate in the proliferative zone of the growth plate. These columns are disorganized in achondroplasia patients. Additionally, the hypertrophic zone is where the cells become large and eventually apoptose (lyse), leading to osteocyte invasion and mineralization. The hypertrophic chondrocytes and the overall size of the zone are much smaller in achondroplasia patients than in normal patients. CNP is an agonist for NPR-B, a positive regulator of chondrocyte and bone growth. Downstream signaling of CNP/NPR-B inhibits the FGFR-3 pathway at the level of mitogen-activated protein kinase (MAPK). Inhibition at MAPK promotes proliferation and differentiation of the chondrocytes in the proliferative and hypertrophic zones of the growth plate, resulting in bone growth.

In humans activating mutations of FGFR-3 are the primary cause of genetic dwarfism. Mice having activated FGFR-3 serve as a model of achondroplasia, the most common form of the skeletal dysplasias, and overexpression of CNP rescues these animals from dwarfism. Accordingly, CNP and functional variants of CNP are potential therapeutics for treatment of the various skeletal dysplasias.

Therapeutic use of CNP is currently limited by its short plasma half-life, which has been shown to be 2.6 minutes in vivo in humans (Hunt et al., J Clin. Endocrinol. Metab., 78: 1428-35 (1994)). To increase CNP concentration above intrinsic levels (about 5 pM) typically found in human plasma, continuous infusion has been necessary in all human and animal studies using systemically administered CNP. Two mechanisms by which the half-life of CNP is reduced in human plasma are degradation by neutral endopeptidase (NEP) and clearance by natriuretic peptide receptor C (NPR-C) (Olney, Growth Horm. & IGF Res., 16: S6-S14 (2006)). A CNP variant having a longer in vivo serum half-life and exhibiting similar or improved activity to that of wild-type CNP is important for a sustainable therapeutic strategy.

The biological activities of various analogs and derivatives of CNP have been evaluated. See e.g., U.S. Pat. No. 7,276,481, PCT Publication No. WO 94/20534 which discloses a chimera of CNP-22 and the 5-amino acid C-terminus of ANP designated as the vasonatrin peptide (VNP). U.S. Pat. Nos. 8,198,242, 8,598,121, 9,907,834 and 10,646,550 disclose use of CNP variants to treat skeletal dysplasias, such as achondroplasia. U.S. Pat. Nos. 7,642,243 and 8,658,373 describe use of variants of CNP-22 or CNP-53 to treat arthritis.

SUMMARY

The present disclosure relates to use of CNP variant peptides to treat skeletal dysplasias in children, for example, children between 2 and 5 years old, and in particular children less than or about 2 years old, to treat one or more skeletal dysplasia-associated symptom(s), or to improve one or more consequence(s) or physiological symptom(s) of a skeletal dysplasia in a subject suffering therefrom, when the CNP variant peptide is administered above a certain dose amount and/or under a certain drug administration regime as herein described. It is disclosed herein that administration of CNP variant peptides can lead to improved growth velocity in achondroplasia subjects.

In various embodiments, the disclosure provides a method of treating skeletal dysplasia in a subject from about 2 years old to about 5 years old, comprising administering to the subject a composition comprising a C type natriuretic peptide (CNP) variant in an amount effective to treat the skeletal dysplasia in the subject, or improve at least one symptom or physiological consequence of the skeletal dysplasia, wherein the CNP variant is selected from the group consisting of the CNP variants disclosed herein.

In various embodiments, the disclosure provides a method of treating skeletal dysplasia in a subject less than or about 2 years old, comprising administering to the subject a composition comprising a C type natriuretic peptide (CNP) variant in an amount effective to treat the skeletal dysplasia in the subject, or improve at least one symptom or physiological consequence of the skeletal dysplasia, wherein the CNP variant is selected from the group consisting of the CNP variants disclosed herein.

In various embodiments, the composition is administered at a dose of 30 µg/kg. In various embodiments, the subject is about 6 months to about 2 years old. In various embodiments, the subject is 0 to about 6 months old. In various embodiments, the subject is about 3 to about 6 months old. In various embodiments, the subject is 0 to about 3 months old. In various embodiments, if the subject starts treatment at younger than about 2 years old, the dosage may be decreased to 15 µg/kg when the subject reaches 2 years old.

In one embodiment, the treatment is an improvement in one or more symptoms of skeletal dysplasia selected from the group consisting of increased absolute growth, improved or increased growth velocity, increased QCT bone mineral density (BMD), improvement in growth plate morphology, increased long-bone growth, improvement in the morphology of the spine, improved or increased elbow joint range of motion and decreased sleep apnea.

In one embodiment, the skeletal dysplasia is selected from the group consisting of achondroplasia, hypochondroplasia, short stature, dwarfism, osteochondrodysplasias, thanatophoric dysplasia, osteogenesis imperfecta, achondrogenesis, chondrodysplasia punctata, homozygous achondroplasia, campomelic dysplasia, congenital lethal hypophosphatasia, perinatal lethal type of osteogenesis imperfecta, short-rib polydactyly syndromes, hypochondroplasia, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, spondyloepimetaphyseal dysplasia, NPR2 mutation, SHOX mutation (Turner's syndrome/Leri Weill), PTPN11 mutations (Noonan's syndrome), and idiopathic short stature. In one embodiment, the skeletal dysplasia is achondroplasia.

Also provided is a method of increasing long bone growth in a subject less than or about 2 years old, comprising administering a composition comprising a CNP variant peptide to a subject in need thereof, wherein the administering increases long bone growth. Also provided is a method of increasing long bone growth in a subject about 2 years old to about 5 years old, comprising administering a composition comprising a CNP variant peptide to a subject in need thereof, wherein the administering increases long bone growth. In one embodiment, the subject has achondroplasia.

The disclosure also contemplates a method of enhancing or increasing the velocity of growth (i.e., growth velocity) in a subject less than or about 2 years old, comprising administering a composition comprising a CNP variant peptide to a subject in need thereof, wherein the administering enhances or increases growth velocity in the subject. Also provided is a method of enhancing or increasing the velocity of growth (i.e., growth velocity) in a subject about 2 years old to about 5 years old, comprising administering a composition comprising a CNP variant peptide to a subject in need thereof, wherein the administering enhances or increases growth velocity in the subject. In one embodiment, the subject has achondroplasia. In various embodiments, the enhancement or increase in growth velocity is an increase in annualized growth velocity in the range of 25%-50% change from baseline in the subject. In one embodiment, the enhancement or increase in growth velocity is an increase in annualized growth velocity of at least about 25%, more preferably at least about 40%, change from baseline in the subject.

It is contemplated that the enhancement in growth velocity may be assessed by measuring standing height, sitting height, weight, head circumference, upper arm length, lower arm length, upper leg length, lower leg length, hand length and/or foot length.

In the various methods and compositions described herein, the CNP variant peptide is selected from the group consisting of:

```
(Pro-Gly-CNP37)
                                       (SEQ ID NO: 1)
PGQEHPNARKYKGANKKGLSKGCFGLKLDRIGSMSGLGC;

(Gly-CNP53)
                                       (SEQ ID NO: 2)
GDLRVDTKSRAAWARLLQEHPNARKYKGANKKGLSKGCFGLKLDRIGSMS

GLGC;

(Pro-CNP53)
                                       (SEQ ID NO: 3)
PDLRVDTKSRAAWARLLQEHPNARKYKGANKKGLSKGCFGLKLDRIGSMS

GLGC;

(Met-CNP53)
                                       (SEQ ID NO: 4)
MDLRVDTKSRAAWARLLQEHPNARKYKGANKKGLSKGCFGLKLDRIGSMS

GLGC;

[CNP-53(M48N)]
                                       (SEQ ID NO: 5)
DLRVDTKSRAAWARLLQEHPNARKYKGANKKGLSKGCFGLKLDRIGSNSG

LGC;

(CNP-52)
                                       (SEQ ID NO: 6)
LRVDTKSRAAWARLLQEHPNARKYKGANKKGLSKGCFGLKLDRIGSMSGL

GC;

(CNP-51)
                                       (SEQ ID NO: 7)
RVDTKSRAAWARLLQEHPNARKYKGANKKGLSKGCFGLKLDRIGSMSGLG

C;

(CNP-50)
                                       (SEQ ID NO: 8)
VDTKSRAAWARLLQEHPNARKYKGANKKGLSKGCFGLKLDRIGSMSGLG

C;

(CNP-49)
                                       (SEQ ID NO: 9)
DTKSRAAWARLLQEHPNARKYKGANKKGLSKGCFGLKLDRIGSMSGLGC;

(CNP-48)
                                      (SEQ ID NO: 10)
TKSRAAWARLLQEHPNARKYKGANKKGLSKGCFGLKLDRIGSMSGLGC;

(CNP-47)
                                      (SEQ ID NO: 11)
KSRAAWARLLQEHPNARKYKGANKKGLSKGCFGLKLDRIGSMSGLGC;

(CNP-46)
                                      (SEQ ID NO: 12)
SRAAWARLLQEHPNARKYKGANKKGLSKGCFGLKLDRIGSMSGLGC;

(CNP-45)
                                      (SEQ ID NO: 13)
RAAWARLLQEHPNARKYKGANKKGLSKGCFGLKLDRIGSMSGLGC;

(CNP-44)
                                      (SEQ ID NO: 14)
AAWARLLQEHPNARKYKGANKKGLSKGCFGLKLDRIGSMSGLGC;

(CNP-43)
                                      (SEQ ID NO: 15)
AWARLLQEHPNARKYKGANKKGLSKGCFGLKLDRIGSMSGLGC;

(CNP-42)
                                      (SEQ ID NO: 16)
WARLLQEHPNARKYKGANKKGLSKGCFGLKLDRIGSMSGLGC;

(CNP-41)
                                      (SEQ ID NO: 17)
ARLLQEHPNARKYKGANKKGLSKGCFGLKLDRIGSMSGLGC;

(CNP-40)
                                      (SEQ ID NO: 18)
RLLQEHPNARKYKGANKKGLSKGCFGLKLDRIGSMSGLGC;

(CNP-39)
                                      (SEQ ID NO: 19)
LLQEHPNARKYKGANKKGLSKGCFGLKLDRIGSMSGLGC;

(CNP-38)
                                      (SEQ ID NO: 20)
LQEHPNARKYKGANKKGLSKGCFGLKLDRIGSMSGLGC;

(CNP-37)
                                      (SEQ ID NO: 21)
QEHPNARKYKGANKKGLSKGCFGLKLDRIGSMSGLGC;

(CNP-36)
                                      (SEQ ID NO: 22)
EHPNARKYKGANKKGLSKGCFGLKLDRIGSMSGLGC;

(CNP-35)
                                      (SEQ ID NO: 23)
HPNARKYKGANKKGLSKGCFGLKLDRIGSMSGLGC;

(CNP-34)
                                      (SEQ ID NO: 24)
PNARKYKGANKKGLSKGCFGLKLDRIGSMSGLGC;

(CNP-33)
                                      (SEQ ID NO: 25)
NARKYKGANKKGLSKGCFGLKLDRIGSMSGLGC;

(CNP-32)
                                      (SEQ ID NO: 26)
ARKYKGANKKGLSKGCFGLKLDRIGSMSGLGC;

(CNP-31)
                                      (SEQ ID NO: 27)
RKYKGANKKGLSKGCFGLKLDRIGSMSGLGC;

(CNP-30)
                                      (SEQ ID NO: 28)
KYKGANKKGLSKGCFGLKLDRIGSMSGLGC;

(CNP-29)
                                      (SEQ ID NO: 29)
YKGANKKGLSKGCFGLKLDRIGSMSGLGC;

(CNP-28)
                                      (SEQ ID NO: 30)
KGANKKGLSKGCFGLKLDRIGSMSGLGC;
```

```
(CNP-27)
                                        (SEQ ID NO: 31)
GANKKGLSKGCFGLKLDRIGSMSGLGC;

(CNP-26)
                                        (SEQ ID NO: 32)
ANKKGLSKGCFGLKLDRIGSMSGLGC;

(CNP-25)
                                        (SEQ ID NO: 33)
NKKGLSKGCFGLKLDRIGSMSGLGC;

(CNP-24)
                                        (SEQ ID NO: 34)
KKGLSKGCFGLKLDRIGSMSGLGC;

(CNP-23)
                                        (SEQ ID NO: 35)
KGLSKGCFGLKLDRIGSMSGLGC;

(CNP-21)
                                        (SEQ ID NO: 36)
LSKGCFGLKLDRIGSMSGLGC;

(CNP-20)
                                        (SEQ ID NO: 37)
SKGCFGLKLDRIGSMSGLGC;

(CNP-19)
                                        (SEQ ID NO: 38)
KGCFGLKLDRIGSMSGLGC;

(CNP-18)
                                        (SEQ ID NO: 39)
GCFGLKLDRIGSMSGLGC;

[CNP37(M32N)
                                        (SEQ ID NO: 40)
QEHPNARKYKGANKKGLSKGCFGLKLDRIGSNSGLGC;

(Pro-CNP37)
                                        (SEQ ID NO: 41)
PQEHPNARKYKGANKKGLSKGCFGLKLDRIGSMSGLGC;

(Met-CNP37)
                                        (SEQ ID NO: 42)
MQEHPNARKYKGANKKGLSKGCFGLKLDRIGSMSGLGC;

(Gly-CNP37)
                                        (SEQ ID NO: 43)
GQEHPNARKYKGANKKGLSKGCFGLKLDRIGSMSGLGC;

[Gly-CNP37(M32N)]
                                        (SEQ ID NO: 44)
GQEHPNARKYKGANKKGLSKGCFGLKLDRIGSNSGLGC;

(Met-Gly-CNP37)
                                        (SEQ ID NO: 45)
MGQEHPNARKYKGANKKGLSKGCFGLKLDRIGSMSGLGC;

(HSA-CNP27)
                                        (SEQ ID NO: 46)
GHKSEVAHRFKGANKKGLSKGCFGLKLDRIGSMSGLGC;

[HSA-CNP27(M22N)]
                                        (SEQ ID NO: 47)
GHKSEVAHRFKGANKKGLSKGCFGLKLDRIGSNSGLGC;

(Pro-HSA-CNP27)
                                        (SEQ ID NO: 48)
PGHKSEVAHRFKGANKKGLSKGCFGLKLDRIGSMSGLGC;

(Met-HSA-CNP27)
                                        (SEQ ID NO: 49)
MGHKSEVAHRFKGANKKGLSKGCFGLKLDRIGSMSGLGC;

[CNP27(K4, 5, 9R)]
                                        (SEQ ID NO: 50)
GANRRGLSRGCFGLKLDRIGSMSGLGC;

[CNP27(K4, 5, 9R, M22N)]
                                        (SEQ ID NO: 51)
GANRRGLSRGCFGLKLDRIGSNSGLGC;

[Pro-CNP27(K4, 5, 9R)]
                                        (SEQ ID NO: 52)
PGANRRGLSRGCFGLKLDRIGSMSGLGC;

[Met-CNP27(K4, 5, 9R)]
                                        (SEQ ID NO: 53)
MGANRRGLSRGCFGLKLDRIGSMSGLGC;

[PEG1K-CNP27(K4, 5, 9R)]
                                        (SEQ ID NO: 54)
PEG1K-GANRRGLSRGCFGLKLDRIGSMSGLGC;

[PEG1K-CNP27(K4, 5, 9R, M22N)]
                                        (SEQ ID NO: 55)
PEG1K-GANRRGLSRGCFGLKLDRIGSNSGLGC;

[PEG1K-Pro-CNP27(K4, 5, 9R)]
                                        (SEQ ID NO: 56)
PEG1K-PGANRRGLSRGCFGLKLDRIGSMSGLGC;

[PEG1K-Met-CNP27(K4, 5, 9R)]
                                        (SEQ ID NO: 57)
PEG1K-MGANRRGLSRGCFGLKLDRIGSMSGLGC;

[PEO12-CNP27(K4, 5, 9R)]
                                        (SEQ ID NO: 58)
PEO12-GANRRGLSRGCFGLKLDRIGSMSGLGC;

[PEO12-CNP27(K4, 5, 9R, M22N)]
                                        (SEQ ID NO: 59)
PEO12-GANRRGLSRGCFGLKLDRIGSNSGLGC;

[PEO12-Pro-CNP27(K4, 5, 9R)]
                                        (SEQ ID NO: 60)
PEO12-PGANRRGLSRGCFGLKLDRIGSMSGLGC;

[PEO12-Met-CNP27(K4, 5, 9R)]
                                        (SEQ ID NO: 61)
PEO12-MGANRRGLSRGCFGLKLDRIGSMSGLGC;

[PEO24-CNP27(K4, 5, 9R)]
                                        (SEQ ID NO: 62)
PEO24-GANRRGLSRGCFGLKLDRIGSMSGLGC;

PEO24-
[PEO24-CNP27(K4, 5, 9R, M22N)]
                                        (SEQ ID NO: 63)
GANRRGLSRGCFGLKLDRIGSNSGLGC;

[PEO24-Pro-CNP27(K4, 5, 9R)]
                                        (SEQ ID NO: 64)
PEO24-PGANRRGLSRGCFGLKLDRIGSMSGLGC;
and

[PEO24-Met-CNP27(K4, 5, 9R)]
                                        (SEQ ID NO: 65)
PEO24-MGANRRGLSRGCFGLKLDRIGSMSGLGC.
```

In various embodiments, the CNP variant is selected from the group consisting of

```
(Pro-Gly-CNP-37)
                                        (SEQ ID NO: 1)
PGQEHPNARKYKGANKKGLSKGCFGLKLDRIGSMSGLGC;

(Gly-CNP-37)
                                        (SEQ ID NO: 43)
GQEHPNARKYKGANKKGLSKGCFGLKLDRIGSMSGLGC;

(CNP-38)
                                        (SEQ ID NO: 20)
LQEHPNARKYKGANKKGLSKGCFGLKLDRIGSMSGLGC;
```

```
[CNP-37(M32N)]
                                  (SEQ ID NO: 40)
QEHPNARKYKGANKKGLSKGCFGLKLDRIGSNSGLGC;

(Met-CNP-37)
                                  (SEQ ID NO: 42)
MQEHPNARKYKGANKKGLSKGCFGLKLDRIGSMSGLGC;

(Pro-CNP-37)
                                  (SEQ ID NO: 41)
PQEHPNARKYKGANKKGLSKGCFGLKLDRIGSMSGLGC;

[Gly-CNP-37(M32N)
                                  (SEQ ID NO: 44)
GQEHPNARKYKGANKKGLSKGCFGLKLDRIGSNSGLGC;

(Met-Gly-CNP-37)
                                  (SEQ ID NO: 45)
MGQEHPNARKYKGANKKGLSKGCFGLKLDRIGSMSGLGC;

(CNP-37)
                                  (SEQ ID NO: 21)
QEHPNARKYKGANKKGLSKGCFGLKLDRIGSMSGLGC;

(CNP-36)
                                  (SEQ ID NO: 22)
EHPNARKYKGANKKGLSKGCFGLKLDRIGSMSGLGC;

(CNP-35)
                                  (SEQ ID NO: 23)
HPNARKYKGANKKGLSKGCFGLKLDRIGSMSGLGC;
and (CNP-34)
                                  (SEQ ID NO: 24)
PNARKYKGANKKGLSKGCFGLKLDRIGSMSGLGC.
```

In various embodiments, the CNP variant is selected from the group consisting of

```
(Pro-Gly-CNP-37)
                                  (SEQ ID NO: 1)
PGQEHPNARKYKGANKKGLSKGCFGLKLDRIGSMSGLGC;
and (CNP-38)
                                  (SEQ ID NO: 20)
LQEHPNARKYKGANKKGLSKGCFGLKLDRIGSMSGLGC;
```

In the various methods described herein, the amount of CNP variant peptide administered ranges from about 15 µg/kg to about 100 µg/kg, preferably about 15 µg/kg to about 60 µg/kg, more preferably about 30 µg/kg to about 60 µg/kg. In various embodiments, the amount of CNP variant peptide administered is at least about 15 µg/kg, or at least about 30 µg/kg.

In the various methods described herein, the CNP variant peptide or composition or formulation comprising the same is administered either subcutaneously or parenterally, preferably subcutaneously. It is also contemplated that the CNP variant peptide is administered by other routes. Exemplary routes of administration include, but are not limited to subcutaneous, intraarticular, intravenous, intra-arterial, intraperitoneal, intramuscular, intradermal, intrathecal, intraperitoneal, intramuscular, intradermal, intrathecal, topical, transdermal, or transmucosal administration.

In the various methods described herein, the CNP variant peptide or composition or formulation comprising the same is administered to the subject in a single treatment or in multiple doses. The multiple doses may be administered once daily, or in multiple doses over the course of treatment. In various embodiments, it is contemplated that the CNP variant peptide or composition or formulation comprising the same is administered, in a single dose or in multiple doses, daily, every other day, every 3 days, 2 times per week, 3 times per week, weekly, bi-weekly, every 3 weeks, monthly, every 6 weeks, every 2 months, every 3 months or other as deemed appropriate by a treating physician. In particularly preferred embodiments, the CNP variant peptide or composition or formulation comprising the same is administered to the subject once daily for a period of at least one month, two months, three months, four months, five months, six months, seven months, eight months, nine months, ten months, eleven months, twelve months, or longer.

In certain embodiments of the methods described herein, administration of the CNP variant peptide or composition or formulation comprising the same is adjusted to allow for periods of preventative or therapeutic treatment followed by a recovery period. For example, the CNP variant peptide or composition or formulation comprising the same may be administered intraarticularly, subcutaneously, intravenously, or by another mode daily or multiple times per week for a period of time, followed by a period of no treatment, then the cycle is repeated. In some embodiments, the initial period of treatment (e.g., administration of the CNP variant peptide daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the CNP variant peptide is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

In the various methods described herein, it is preferred that administration of the CNP variant peptide or composition or formulation comprising the same not cause or result in an adverse event in the subject rated as grade two or higher. In other embodiments of the methods described herein, administration of the CNP variant peptide or composition or formulation comprising the same results in no clinically significant change in blood hemoglobin concentration, blood platelet number, blood electrolyte concentration, blood urea nitrogen concentration, blood creatinine concentration, blood alkaline phosphatase concentration, blood alanine amino transferase concentration and/or blood aspartate aminotransferase concentration in said subject.

In the various methods described herein, in preferred embodiments, administration of the CNP variant peptide or composition or formulation comprising the same results in a change in (i) the upper body length to lower body length ratio, (ii) the upper arm length to forearm length ratio, or (iii) the upper leg length to lower leg length ratio, of between about −0.25 and about 0.25, about −0.20 and about 0.20, about −0.15 and about 0.15, about −0.10 and about 0.10, or about −0.05 and about 0.05, compared to baseline (i.e., prior to administration of the CNP variant peptide or composition or formulation comprising the same).

In various embodiments, the disclosure provides for compositions or formulations comprising a CNP variant peptide, or use of a composition or formulation comprising a CNP variant peptide in the methods described herein. In one embodiment, the composition or formulation further comprises a pharmaceutically acceptable excipient, carrier or diluent. In certain embodiments, the composition is prepared from a formulation, either liquid or lyophilized, comprising a citric acid/citrate buffer or an acetic acid/acetate buffer having a pH from about 4 to about 6. In various embodiments, the pH is about 5.5.

Also contemplated is a method of treatment as described herein further comprising administration of a second agent.

In various embodiments, the CNP variant peptides used in the methods and compositions or formulations described herein can be attached to a hydrophobic acid, and can be attached to one or more hydrophobic acids. Non-limiting examples of hydrophobic acids include straight-chain or branched, saturated or unsaturated C5-C12 carboxylic acids (e.g., pentanoic acid, heptanoic acid, etc.) and natural fatty acids. The hydrophobic acids can be attached to the N-terminus, the C-terminus, and/or the side chain of one or more amino acid residues. In one embodiment, the hydrophobic acids are conjugated to the N-terminus.

In yet another embodiment, the CNP variant peptides used in the methods and compositions of the present invention are chimera, or fusion proteins, comprising a CNP variant peptide, and a cleavable peptide or protein, or peptide tag. Exemplary cleavable proteins or peptides include, but are not limited to, histidine (e.g., hexa-His) tags; TAF12: human transcription factor TAF12; KSI: ketosteroid isomerase; MBP: maltose-binding protein; 13-Gal: 13-galactosidase; GST: glutathione-S-transferase; Trx: thioredoxin; CBD: chitin binding domain; BMPM: BMP-2 mutation, SUMO, CAT, TrpE, staphylococcal protein A, streptococcal proteins, starch-binding protein, cellulose-binding domain of endoglucanase A, cellulose-binding domain of exoglucanase Cex, biotin-binding domain, recA, Flag, c-Myc, poly(His), poly(Arg), poly(Asp), poly(Gln), poly(Phe), poly(Cys), green fluorescent protein, red fluorescent protein, yellow fluorescent protein, cyan fluorescent protein, biotin, avidin, streptavidin, antibody epitopes, and fragments thereof.

In various embodiments, the CNP variant peptide useful in the methods may be a monomer or a dimer. In a related embodiment the monomers of dimeric CNP variant peptides can be attached N-terminus to N-terminus via a linker or no linker, N-terminus to C-terminus via a linker or no linker, or C-terminus to C-terminus via a linker or no linker.

In any of the embodiments disclosed herein, the CNP variant peptides may have substantially the same or better biological activity than wild-type CNP-22. For example, the CNP variant peptides may retain at least 50%, 60%, 70%, 80%, 90%, 95% or more of the activity of wild-type CNP-22, or may have greater activity than CNP-22, e.g., with respect to interaction with NPR-B (GC-B) to stimulate the generation of cGMP. Alternatively, or in addition, the CNP variant peptides may retain at least 50%, 60%, 70%, 80%, 90%, 95% or more of the activity of wild-type CNP-22, or may have greater activity than CNP-22, with respect to regulating endochondral bone growth and chondrocyte activity, including but not limited to chondrocyte proliferation, chondrocyte differentiation, inhibition of the mitogen activated protein (MAP) kinase/MEK (Raf-1) kinase signaling pathway, and promoting endochondral ossification. In any of the embodiments described herein, the CNP variant peptides may comprise an amino acid sequence that is at least 40%, 50%, 60%, 70%, 80%, 90%, 95% or more identical or homologous to amino acids 6-22 or 1-22 of wild-type CNP-22.

In various embodiments, the CNP variant peptides can optionally have conjugation(s) or extension(s), e.g., at the N- and/or C-terminus to facilitate cartilage targeting, reduce renal clearance, and/or increase resistance to NEP degradation. Such conjugation(s) or extension(s) can comprise molecules or sequences formed or derived from, e.g., polyAsp, polyGlu, cartilage-targeting peptides, sialoprotein, PEGs, carbohydrates, hydrophobic acids, NPPC or non-CNP (poly) peptides, or combinations thereof.

It is further contemplated that the CNP variant peptides can be conjugated to a hydrophobic polymeric or non-polymeric moiety, such as, e.g., heptanoic acid, pentanoic acid, or fatty acids. The hydrophobic moiety can be conjugated to the side chain of an amino acid residue, including but not limited to a lysine, a serine, a cysteine or a threonine, or can be attached to the N-terminus and/or C-terminus of the CNP variant.

In various embodiments, the CNP variant comprises a synthetic polymeric group. In various embodiments, the variant comprises a synthetic polymeric group coupled to the variant through a hydrolysable linker. In various embodiments, the synthetic polymeric group comprises a hydrophilic polymer moiety. In various embodiments, the hydrophilic polymer moiety comprises polyethylene glycol (PEG).

In various embodiments, the disclosure provides for use of a pharmaceutical composition comprising a CNP variant peptide, optionally another biologically active agent, and optionally a pharmaceutically acceptable excipient, carrier or diluent. In various embodiments, the compositions are sterile pharmaceutical compositions suitable for parenteral injection. In some embodiments, the compositions comprise substantially pure CNP variant peptide, e.g. at least about 90% or 95% pure. In some embodiments, the compositions contain less than about 5%, 4%, 3%, 2%, 1% or 0.5% contaminants, such as other human proteins, porcine proteins, or CNP-53 or fragments thereof (other than the desired CNP variant peptide). In various embodiments, the sterile composition is administered to a subject for treating or preventing a skeletal dysplasia or one or more symptoms or physiological consequences of a skeletal dysplasia disclosed herein.

CNP variant peptides useful herein advantageously retain CNP activity and exhibit increased serum half-life. Retention of CNP activity can be shown, for example, as retention of desired in vivo biological effect, or retention of at least about 50%, 60%, 70%, 80%, 90%, 95% or at least about 100% of the cGMP stimulating activity of CNP-22, under the same concentration (e.g., 1 pM of CNP peptide or greater than the ED80). In some embodiments, CNP variant peptides exhibit at least about 1.5-fold, 2-fold, 3-fold, 4-fold, 5-fold, 10-fold, 15-fold, 20-fold, 25-fold, 30-fold, 35-fold or 40-fold increase in serum half-life compared to CNP-22.

In a related embodiment, the CNP variant peptides described herein have increased NEP resistance and exhibit increased half-life compared to wild-type CNP-22. In one embodiment, the half-life of the CNP variant peptides is increased by about 20%, 30%, 40%, 50%, 60%, 70%, 80%, 90%, 95%, 96%, 97%, 98%, 99% or about 100% compared to wild-type CNP-22.

Use of any of the foregoing CNP variant peptides, or composition or formulation comprising the same, described herein in preparation of a medicament for treatment of skeletal dysplasia in children less than or about 2 years old and symptoms or other physiological manifestations described herein associated with skeletal dysplasia is also contemplated. Use of any of the foregoing CNP variant peptides, or composition or formulation comprising the same, described herein in preparation of a medicament for treatment of skeletal dysplasia in children about 2 to about 5 years old and symptoms or other physiological manifestations described herein associated with skeletal dysplasia is also contemplated. Syringes, e.g., single use or pre-filled syringes, sterile sealed containers, e.g. vials, bottle, vessel, and/or kits or packages comprising any of the foregoing CNP variant peptides, or composition or formulation comprising the same, optionally with suitable instructions for use, are also contemplated.

It is also contemplated that the CNP variants are in a formulation comprising (a) a CNP variant peptide described herein and (b) one or more components selected from the group consisting of a buffering agent, an isotonicity agent, a stabilizer and an anti-adsorbent agent. In particularly preferred embodiments, buffering agents employed in the formulations may be citric acid monohydrate, sodium citrate dihydrate, or a combination of the two. In yet other preferred embodiments, isotonicity agents employed in the formulations of the present invention may be trehalose dihydrate, D-mannitol, or a combination of the two. In other preferred embodiments, the stabilizer employed in the formulations of the present invention is L-methionine. In yet other preferred embodiments, the anti-adsorbent agent employed in the formulations of the present invention is polysorbate 80.

In various embodiments, the formulations useful in the methods are lyophilized, in liquid form, or in liquid form that has been reconstituted from a previously lyophilized form. In certain embodiments, the formulations useful in the methods are preservative-free and, optionally, may be contained within a type 1 untreated borosilicate glass vial. Optionally, the formulations have a pH in the range of between about 5.0 and about 6.0, preferably about 5.5.

In some embodiments, the compositions are liquid formulations. In certain embodiments, the formulations comprise a CNP variant in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 0.5 to 5 mg/ml, or from about 0.5 to 3 mg/ml, or from about 0.5 mg/ml to about 2.0 mg/ml, or from about 0.8 to about 2.0 mg/ml, or from about 1 mg/ml to about 10 mg/ml. In various embodiments, the CNP variant is in a concentration of 0.5 mg/mL to 2 mg/mL. In various embodiments, the CNP variant is in a concentration of 0.8 mg/mL to 2 mg/mL. In various embodiments, the CNP variant is at a concentration of 0.8 mg/mL. In various embodiments, the CNP variant is at a concentration of 2.0 mg/mL. In various embodiments, the CNP variant is reconstituted from a lyophilized powder. In various embodiments, the CNP variant peptide of the formulation is CNP-38 or Pro-Gly-CNP-37 (BMN111).

In other embodiments, the formulations useful in the methods comprise a CNP variant peptide as described herein, citric acid monohydrate, sodium citrate dihydrate, trehalose dihydrate, D-mannitol, L-methionine and polysorbate 80. In certain embodiments, the CNP variant peptide is present at a concentration between about 0.5 mg/ml and about 2.0 mg/ml, the citric acid monohydrate is present at a concentration between about 0.15 mg/ml and about 0.40 mg/ml, the sodium citrate dihydrate is present at a concentration between about 0.5 mg/ml and about 1.5 mg/ml, the trehalose dihydrate is present at a concentration between about 30 mg/ml and about 70 mg/ml, the D-mannitol is present at a concentration between about 10 mg/ml and about 20.0 mg/ml, the L-methionine is present at a concentration between about 0.5 mg/ml and about 1.5 mg/ml and the polysorbate 80 is present at a concentration between about 0.01 mg/ml and about 0.1 mg/ml. In various embodiments, the CNP variant is present at a concentration of about 2.0 mg/ml, the citric acid monohydrate is present at a concentration of about 0.28 mg/ml, the sodium citrate dihydrate is present at a concentration of about 1.08 mg/ml, the trehalose dihydrate is present at a concentration of about 58.01 mg/ml, the D-mannitol is present at a concentration of about 15.0 mg/ml, the L-methionine is present at a concentration of about 0.73 mg/ml and the polysorbate 80 is present at a concentration of about 0.05 mg/ml. In various embodiments, the CNP variant is present at a concentration of about 0.8 mg/ml, the citric acid monohydrate is present at a concentration of about 0.28 mg/ml, the sodium citrate dihydrate is present at a concentration of about 1.08 mg/ml, the trehalose dihydrate is present at a concentration of about 58.01 mg/ml, the D-mannitol is present at a concentration of about 15.0 mg/ml, the L-methionine is present at a concentration of about 0.73 mg/ml and the polysorbate 80 is present at a concentration of about 0.05 mg/ml.

It is understood that each feature or embodiment, or combination, described herein is a non-limiting, illustrative example of any of the aspects of the disclosure and, as such, is meant to be combinable with any other feature or embodiment, or combination, described herein. For example, where features are described with language such as "one embodiment", "some embodiments", "further embodiment", "specific exemplary embodiments", and/or "another embodiment", each of these types of embodiments is a non-limiting example of a feature that is intended to be combined with any other feature, or combination of features, described herein without having to list every possible combination. Such features or combinations of features apply to any of the aspects of the disclosure. Where examples of values falling within ranges are disclosed, any of these examples are contemplated as possible endpoints of a range, any and all numeric values between such endpoints are contemplated, and any and all combinations of upper and lower endpoints are envisioned.

BRIEF DESCRIPTION OF THE FIGURES

FIG. 1 shows the demographic makeup of the study groups for 52-week vosoritide treatment in Cohorts 1-3.

DETAILED DESCRIPTION

Figure 2:
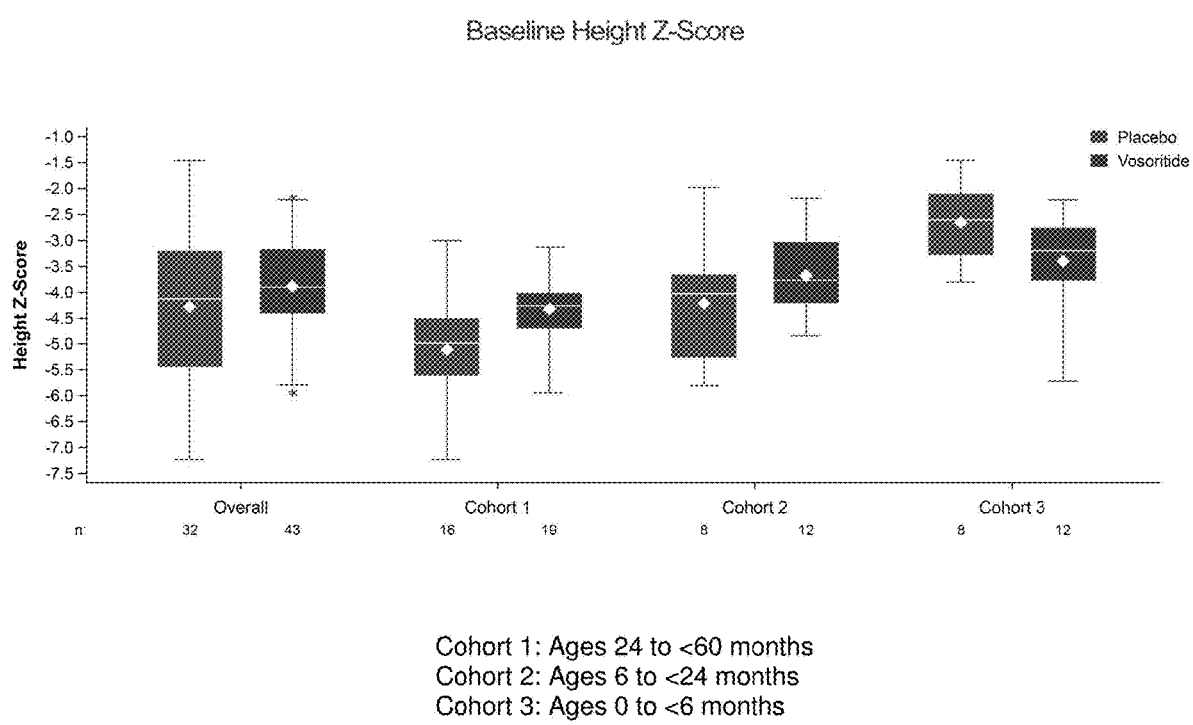
FIG. 2 represents baseline Z score for study Cohorts 1-3 at 52 weeks of treatment.

The present disclosure relates to methods of using CNP variant peptides to treat skeletal dysplasias in children less than or about 2 years old, one or more symptoms or physiological consequences of skeletal dysplasias and other disorders having a skeletal dysplasia and/or CNP-associated symptom or component. Treatment with a CNP variant peptide in skeletal dysplasia reduces one or more symptoms or physiological consequence of a skeletal dysplasia, increases long bone growth in a subject in need thereof, or improves or increases growth velocity in a subject in need thereof, for example in a subject suffering from a skeletal dysplasia.

Definitions

Unless otherwise stated, the following terms used in this application, including the specification and claims, have the definitions given below.

As used in the specification and the appended claims, the indefinite articles "a" and "an" and the definite article "the" include plural as well as singular referents unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range. Whenever the term "about" or "approximately" precedes the first numerical value in a series of two or more numerical values, it is understood that the term "about" or "approximately" applies to each one of the numerical values in that series.

Definition of standard chemistry terms may be found in reference works, including Carey and Sundberg, Advanced Organic Chemistry, 3rd Edition, Vols. A and B (Plenum Press, N.Y. 1992). The practice of the present disclosure may employ, unless otherwise indicated, certain conventional methods of synthetic organic chemistry, mass spectrometry, preparative and analytical chromatography, protein chemistry, biochemistry, recombinant DNA technology and pharmacology, within the skill of the art. See, e.g., T. E. Creighton, Proteins: Structures and Molecular Properties (W.H. Freeman and Company, 1993); A. L. Lehninger, Biochemistry (Worth Publishers, Inc., 4th Edition, 2004); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pennsylvania: Mack Publishing Company, 1990).

All publications, patents and patent applications cited herein, whether supra or infra, are hereby incorporated by reference in their entirety.

The following amino acid abbreviations are used throughout the text

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

Conventional notation is used herein to portray polypeptide and peptide sequences: the left-hand end of a polypeptide or peptide sequence is the amino-terminus; the right-hand end of a polypeptide sequence is the carboxyl-terminus.

In one embodiment, the CNP variant peptides described herein useful in the methods are generated via recombinant means, using a polynucleotide encoding a CNP variant peptide. CNP variant peptides expressed by such polynucleotides may be produced by methods including growing host cells in culture medium under conditions suitable for expression of the polynucleotide encoding a CNP variant, and isolating the expression product from the host cells or culture medium. Actual expression products may vary slightly from the encoded protein product depending on any post-translational processing. Methods for producing the CNP variant peptides of the present invention are disclosed at least in U.S. Pat. No. 8,198,242, incorporated herein by reference.

The terms "identical" and percent "identity", in the context of two or more polynucleotide or polypeptide sequences, refer to two or more sequences or subsequences that are the same or have a specified percentage of nucleotides or amino acid residues that are the same, when compared and aligned for maximum correspondence, as measured using one of the following sequence comparison algorithms or by visual inspection.

The phrase "substantially homologous" or "substantially identical", in the context of two nucleic acids or polypeptides, generally refers to two or more sequences or subsequences that have at least 40%, 50%, 60%, 70%, 80%, 90%, 95%, or 98% nucleotide or amino acid residue identity, when compared and aligned for maximum correspondence, as measured using one of the following sequence comparison algorithms or by visual inspection. In certain embodiments, the substantial homology or identity exists over regions of the sequences that are at least about 25, 50, 100 or 150 residues in length. In another embodiment, the sequences are substantially homologous or identical over the entire length of either or both comparison biopolymers.

For sequence comparison, typically one sequence acts as a reference sequence, to which test sequences are compared. When using a sequence comparison algorithm, test and reference sequences are inputted into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math., 2: 482 (1981), by the homology alignment algorithm of Needleman & Wunsch, J. Mol. Biol., 48: 443 (1970), by the search for similarity method of Pearson & Lipman, Proc. Natl. Acad. Sci. USA, 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by visual inspection. One example of a useful algorithm is PILEUP, which uses a simplification of the progressive alignment method of Feng & Doolittle, J. Mol. Evol., 35: 351-360 (1987) and is similar to the method described by Higgins & Sharp, CABIOS, 5: 151-153 (1989). Another algorithm useful for generating multiple alignments of sequences is Clustal W (Thompson et al., Nucleic Acids Research, 22: 4673-4680 (1994)). An example of an algorithm that is suitable for determining percent sequence identity and sequence similarity is the BLAST algorithm (Altschul et al., J. Mol. Biol., 215: 403-410 (1990); Henikoff & Henikoff, Proc. Natl. Acad. Sci. USA, 89: 10915 (1989); Karlin & Altschul, Proc. Natl. Acad. Sci. USA, 90: 5873-5787 (1993)). Software for performing BLAST analyses is publicly available through the National Center for Biotechnology Information.

"Wild-type" (wt) is a term referring to the natural form, including sequence, of a polynucleotide, polypeptide or protein in a species. A wild-type form is distinguished from a mutant form of a polynucleotide, polypeptide or protein arising from genetic mutation(s).

In one embodiment, a first peptide that is an "analog" or "variant" or "derivative" of a second peptide is a peptide having at least about 50%, 60% or 70% sequence homology, but less than 100% sequence homology, with the second peptide. Such analogs, variants or derivatives may be comprised of non-naturally occurring amino acid residues, including without limitation, homoarginine, ornithine, penicillamine, and norvaline, as well as naturally occurring amino acid residues.

The natriuretic peptide precursor C (NPPC) polypeptide is a single chain 126-amino acid pre-pro polypeptide, and which upon cleavage ultimately results in wild type CNP-22 (wtCNP-22). Removal of the signal peptide from NPPC yields pro-CNP, and further cleavage by the endoprotease furin generates an active 53-amino acid peptide (CNP-53), which is secreted and cleaved again to produce the mature 22-amino acid peptide (CNP, or CNP-22). In one embodiment, a "CNP variant peptide" is at least about 40%, 50%, 60%, 70%, 75%, 80%, 85%, 90%, or 95% homologous to the wild type NPPC over the same number of amino acid residues. It is further contemplated that a CNP variant peptide may comprise from about 1 to about 53, or 1 to 38, or 1 to 37, or 1 to 35, or 1 to 34, or 1 to 33, or 1 to 32, or 1 to 31, or 1 to 27, or 1 to 22, or 10 to 35, or about 15 to about 37 residues of the NPPC polypeptide. In one embodiment, a CNP variant may comprise a sequence of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, or 53 amino acids derived from the NPPC polypeptide.

The term "effective amount" means a dosage sufficient to produce a desired result on a health condition, pathology, or disease of a subject or for a diagnostic purpose. The desired result may comprise a subjective or objective improvement in the recipient of the dosage. "Therapeutically effective amount" refers to that amount of an agent effective to produce the intended beneficial effect on health. An appropriate "effective" amount in any individual case may be determined by one of ordinary skill in the art using routine experimentation. It will be understood that the specific dose level and frequency of dosage for any particular patient may be varied and will depend upon a variety of factors, including the activity of the specific compound employed; the bioavailability, metabolic stability, rate of excretion and length of action of that compound; the mode and time of administration of the compound; the age, body weight, general health, sex, and diet of the patient; and the severity of the particular condition.

"Treatment" refers to prophylactic treatment or therapeutic treatment or diagnostic treatment. In certain embodiments, "treatment" refers to administration of a compound or composition to a subject for therapeutic, prophylactic or diagnostic purposes.

A "prophylactic" treatment is a treatment administered to a subject who does not exhibit signs of a disease or exhibits only early signs of the disease, for the purpose of decreasing the risk of developing pathology. The compounds or compositions of the disclosure may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional or physical, subjective or objective. The compounds of the disclosure may also be given as a therapeutic treatment or for diagnosis.

"Pharmaceutical composition" or "formulation" refers to a composition suitable for pharmaceutical use in subject animal, including humans and mammals. A pharmaceutical composition comprises a therapeutically effective amount of a CNP variant peptide, optionally another biologically active agent, and optionally a pharmaceutically acceptable excipient, carrier or diluent. In an embodiment, a pharmaceutical composition encompasses a composition comprising the active ingredient(s), and the inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and a pharmaceutically acceptable excipient, carrier or diluent.

"Pharmaceutically acceptable carrier" refers to any of the standard pharmaceutical carriers, buffers, and the like, such as a phosphate buffered saline solution, 5% aqueous solution of dextrose, and emulsions (e.g., an oil/water or water/oil emulsion). Non-limiting examples of excipients include adjuvants, binders, fillers, diluents, disintegrants, emulsifying agents, wetting agents, lubricants, glidants, sweetening agents, flavoring agents, and coloring agents. Suitable pharmaceutical carriers, excipients and diluents are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration).

A "pharmaceutically acceptable salt" is a salt that can be formulated into a compound for pharmaceutical use, including but not limited to metal salts (e.g., sodium, potassium, magnesium, calcium, etc.) and salts of ammonia or organic amines.

By "pharmaceutically acceptable" or "pharmacologically acceptable" is meant a material that is not biologically or otherwise undesirable, i.e., the material may be administered to an individual without causing any undesirable biological effects or without interacting in a deleterious manner with any of the components of the composition in which it is contained or with any components present on or in the body of the individual.

"Physiological conditions" refer to conditions in the body of an animal (e.g., a human). Physiological conditions include, but are not limited to, body temperature and an aqueous environment of physiologic ionic strength, pH and enzymes. Physiological conditions also encompass conditions in the body of a particular subject which differ from the "normal" conditions present in the majority of subjects, e.g., which differ from the normal human body temperature of approximately 37° C. or differ from the normal human blood pH of approximately 7.4.

As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, and the like. The term does not denote a particular age or gender.

The terms "polyethylene glycol", "PEG", "polyethylene oxide" and "PEO" are used interchangeably herein unless indicated otherwise. A CNP variant conjugated via an amino group to a "PEOn" polymer associated with the number n, in general has the formula: CH3—[—O—CH2CH2—]—C(═O)—NHR, where n is the number of ethylene oxide units and R denotes the rest of the peptide. The "PEOn" polymer can optionally have an alkylene group, (CH2)m, where m is an integer from 1 to 5, between the carbonyl carbon and the repeating ethylene oxide units. Such a "PEOn" (e.g., PEO12 or PEO24) polymer is monodispersed, i.e., is a single discrete polymer of a particular molecular weight. Similarly, a CNP variant conjugated via an amino group to a "PEGnK" polymer associated with the number nK, in general has the formula: CH3—[—O—CH2CH2—]p—C(═O)—NHR, where p is an integer greater than 1. The "PEGnK" polymer also can optionally have an alkylene group, (CH2)m, where m is an integer from 1 to 5, between the carbonyl carbon and the repeating ethylene oxide units. However, such a "PEGnK" (e.g., PEG1K, PEG2K, PEG5K or PEG20K) polymer is polydispersed, i.e., contains a mixture of polymers having a distribution of molecular weights, where the number nK denotes the polymer number-average molecular weight (Mn) in kilo Daltons. For example, "PEG2K" conjugated to a CNP variant denotes a polydispersed PEG polymer having a polymer number-average molecular weight of around 2 kDa.

When a range of the mass of a polymer (e.g., PEG) is given (e.g., in units of kDa), the range refers to a range of polymer number-average molecular weights, not to a range of molecular weights of multiple polymers in a polydispersed mixture, unless expressly indicated otherwise.

CNP Variant Peptides

The use of CNP-22 as a therapeutic is limited by its short half-life in plasma (J. Clin. Endocrinol. Metab., 78: 1428-35 (1994)). In human plasma, the concentration of CNP-22 typically is less than five picomolar. CNP-22 is degraded and cleared from circulation by NEP and NPR-C in humans (Growth Hormone & IGF Res., 16: S6-S14). In all human and animal studies using systemically administered CNP-22, continuous infusion has been used to increase the CNP-22 concentration in the subjects. A CNP peptide having a longer half-life and at least a similar level of functionality would be beneficial to a CNP-based therapeutic strategy. CNP variant peptides having improved properties are disclosed in International Application Nos. WO 2009/067639 and WO 2010/135541 and U.S. Pat. Nos. 8,198,242, 8,598,121, 8,377,884, 9,907,834 and 10,646,550 all specifically incorporated herein by reference.

Exemplary CNP variant peptides contemplated for use in the methods include:

(Pro-Gly-CNP37)
(SEQ ID NO: 1)
PGQEHPNARKYKGANKKGLSKGCFGLKLDRIGSMSGLGC;

(Gly-CNP53)
(SEQ ID NO: 2)
GDLRVDTKSRAAWARLLQEHPNARKYKGANKKGLSKGCFGLKLDRIGSMS
GLGC;

(Pro-CNP53)
(SEQ ID NO: 3)
PDLRVDTKSRAAWARLLQEHPNARKYKGANKKGLSKGCFGLKLDRIGSMS
GLGC;

(Met-CNP53)
(SEQ ID NO: 4)
MDLRVDTKSRAAWARLLQEHPNARKYKGANKKGLSKGCFGLKLDRIGSMS
GLGC;

[CNP-53(M48N)]
(SEQ ID NO: 5)
DLRVDTKSRAAWARLLQEHPNARKYKGANKKGLSKGCFGLKLDRIGSNSG
LGC;

(CNP-52)
(SEQ ID NO: 6)
LRVDTKSRAAWARLLQEHPNARKYKGANKKGLSKGCFGLKLDRIGSMSGL
GC;

(CNP-51)
(SEQ ID NO: 7)
RVDTKSRAAWARLLQEHPNARKYKGANKKGLSKGCFGLKLDRIGSMSGLG
C;

(CNP-50)
(SEQ ID NO: 8)
VDTKSRAAWARLLQEHPNARKYKGANKKGLSKGCFGLKLDRIGSMSGLG
C;

(CNP-49)
(SEQ ID NO: 9)
DTKSRAAWARLLQEHPNARKYKGANKKGLSKGCFGLKLDRIGSMSGLGC;

(CNP-48)
(SEQ ID NO: 10)
TKSRAAWARLLQEHPNARKYKGANKKGLSKGCFGLKLDRIGSMSGLGC;

(CNP-47)
(SEQ ID NO: 11)
KSRAAWARLLQEHPNARKYKGANKKGLSKGCFGLKLDRIGSMSGLGC;

(CNP-46)
(SEQ ID NO: 12)
SRAAWARLLQEHPNARKYKGANKKGLSKGCFGLKLDRIGSMSGLGC;

(CNP-45)
(SEQ ID NO: 13)
RAAWARLLQEHPNARKYKGANKKGLSKGCFGLKLDRIGSMSGLGC;

(CNP-44)
(SEQ ID NO: 14)
AAWARLLQEHPNARKYKGANKKGLSKGCFGLKLDRIGSMSGLGC;

(CNP-43)
(SEQ ID NO: 15)
AWARLLQEHPNARKYKGANKKGLSKGCFGLKLDRIGSMSGLGC;

(CNP-42)
(SEQ ID NO: 16)
WARLLQEHPNARKYKGANKKGLSKGCFGLKLDRIGSMSGLGC;

(CNP-41)
(SEQ ID NO: 17)
ARLLQEHPNARKYKGANKKGLSKGCFGLKLDRIGSMSGLGC;

(CNP-40)
(SEQ ID NO: 18)
RLLQEHPNARKYKGANKKGLSKGCFGLKLDRIGSMSGLGC;

(CNP-39)
(SEQ ID NO: 19)
LLQEHPNARKYKGANKKGLSKGCFGLKLDRIGSMSGLGC;

(CNP-38)
(SEQ ID NO: 20)
LQEHPNARKYKGANKKGLSKGCFGLKLDRIGSMSGLGC;

-continued (CNP-37)
(SEQ ID NO: 21)
QEHPNARKYKGANKKGLSKGCFGLKLDRIGSMSGLGC;

(CNP-36)
(SEQ ID NO: 22)
EHPNARKYKGANKKGLSKGCFGLKLDRIGSMSGLGC;

(CNP-35)
(SEQ ID NO: 23)
HPNARKYKGANKKGLSKGCFGLKLDRIGSMSGLGC;

(CNP-34)
(SEQ ID NO: 24)
PNARKYKGANKKGLSKGCFGLKLDRIGSMSGLGC;

(CNP-33)
(SEQ ID NO: 25)
NARKYKGANKKGLSKGCFGLKLDRIGSMSGLGC;

(CNP-32)
(SEQ ID NO: 26)
ARKYKGANKKGLSKGCFGLKLDRIGSMSGLGC;

(CNP-31)
(SEQ ID NO: 27)
RKYKGANKKGLSKGCFGLKLDRIGSMSGLGC;

(CNP-30)
(SEQ ID NO: 28)
KYKGANKKGLSKGCFGLKLDRIGSMSGLGC;

(CNP-29)
(SEQ ID NO: 29)
YKGANKKGLSKGCFGLKLDRIGSMSGLGC;

(CNP-28)
(SEQ ID NO: 30)
KGANKKGLSKGCFGLKLDRIGSMSGLGC;

(CNP-27)
(SEQ ID NO: 31)
GANKKGLSKGCFGLKLDRIGSMSGLGC;

(CNP-26)
(SEQ ID NO: 32)
ANKKGLSKGCFGLKLDRIGSMSGLGC;

(CNP-25)
(SEQ ID NO: 33)
NKKGLSKGCFGLKLDRIGSMSGLGC;

(CNP-24)
(SEQ ID NO: 34)
KKGLSKGCFGLKLDRIGSMSGLGC;

(CNP-23)
(SEQ ID NO: 35)
KGLSKGCFGLKLDRIGSMSGLGC;

(CNP-21)
(SEQ ID NO: 36)
LSKGCFGLKLDRIGSMSGLGC;

(CNP-20)
(SEQ ID NO: 37)
SKGCFGLKLDRIGSMSGLGC;

(CNP-19)
(SEQ ID NO: 38)
KGCFGLKLDRIGSMSGLGC;

(CNP-18)
(SEQ ID NO: 39)
GCFGLKLDRIGSMSGLGC;

[CNP37(M32N)
(SEQ ID NO: 40)
QEHPNARKYKGANKKGLSKGCFGLKLDRIGSNSGLGC;

(Pro-CNP37)
(SEQ ID NO: 41)
PQEHPNARKYKGANKKGLSKGCFGLKLDRIGSMSGLGC;

(Met-CNP37)
(SEQ ID NO: 42)
MQEHPNARKYKGANKKGLSKGCFGLKLDRIGSMSGLGC;

(Gly-CNP37)
(SEQ ID NO: 43)
GQEHPNARKYKGANKKGLSKGCFGLKLDRIGSMSGLGC;

[Gly-CNP37(M32N)]
(SEQ ID NO: 44)
GQEHPNARKYKGANKKGLSKGCFGLKLDRIGSNSGLGC;

(Met-Gly-CNP37)
(SEQ ID NO: 45)
MGQEHPNARKYKGANKKGLSKGCFGLKLDRIGSMSGLGC;

(HSA-CNP27)
(SEQ ID NO: 46)
GHKSEVAHRFKGANKKGLSKGCFGLKLDRIGSMSGLGC;

[HSA-CNP27 (M22N)]
(SEQ ID NO: 47)
GHKSEVAHRFKGANKKGLSKGCFGLKLDRIGSNSGLGC;

(Pro-HSA-CNP27)
(SEQ ID NO: 48)
PGHKSEVAHRFKGANKKGLSKGCFGLKLDRIGSMSGLGC;

(Met-HSA-CNP27)
(SEQ ID NO: 49)
MGHKSEVAHRFKGANKKGLSKGCFGLKLDRIGSMSGLGC;

[CNP27(K4, 5, 9R)]
(SEQ ID NO: 50)
GANRRGLSRGCFGLKLDRIGSMSGLGC;

[CNP27(K4, 5, 9R, M22N)]
(SEQ ID NO: 51)
GANRRGLSRGCFGLKLDRIGSNSGLGC;

[Pro-CNP27(K4, 5, 9R)]
(SEQ ID NO: 52)
PGANRRGLSRGCFGLKLDRIGSMSGLGC;

[Met-CNP27(K4, 5, 9R)]
(SEQ ID NO: 53)
MGANRRGLSRGCFGLKLDRIGSMSGLGC;

[PEG1K-CNP27(K4, 5, 9R)]
(SEQ ID NO: 54)
PEG1K-GANRRGLSRGCFGLKLDRIGSMSGLGC;

[PEG1K-CNP27(K4, 5, 9R, M22N)]
(SEQ ID NO: 55)
PEG1K-GANRRGLSRGCFGLKLDRIGSNSGLGC;

[PEG1K-Pro-CNP27(K4, 5, 9R)]
(SEQ ID NO: 56)
PEG1K-PGANRRGLSRGCFGLKLDRIGSMSGLGC;

[PEG1K-Met-CNP27(K4, 5, 9R)]
(SEQ ID NO: 57)
PEG1K-MGANRRGLSRGCFGLKLDRIGSMSGLGC;

[PEO12-CNP27(K4, 5, 9R)]
(SEQ ID NO: 58)
PEO12-GANRRGLSRGCFGLKLDRIGSMSGLGC;

[PEO12-CNP27(K4, 5, 9R, M22N)]
(SEQ ID NO: 59)
PEO12-GANRRGLSRGCFGLKLDRIGSNSGLGC;

[PEO12-Pro-CNP27(K4, 5, 9R)]
(SEQ ID NO: 60)
PEO12-PGANRRGLSRGCFGLKLDRIGSMSGLGC;

```
-continued
[PEO12-Met-CNP27(K4, 5, 9R)]
                                            (SEQ ID NO: 61)
PEO12-MGANRRGLSRGCFGLKLDRIGSMSGLGC;

[PEO24-CNP27(K4, 5, 9R)]
                                            (SEQ ID NO: 62)
PEO24-GANRRGLSRGCFGLKLDRIGSMSGLGC;

[PEO24-CNP27(K4, 5, 9R, M22N)]
                                            (SEQ ID NO: 63)
PEO24-GANRRGLSRGCFGLKLDRIGSNSGLGC;
and/or

[PEO24-Pro-CNP27(K4, 5, 9R)]
                                            (SEQ ID NO: 64)
PEO24-PGANRRGLSRGCFGLKLDRIGSMSGLGC.
```

In certain embodiments, the CNP variant peptides are derivatives of CNP-37 or CNP-38. The CNP-37 variant peptides can contain amino acid addition(s), deletion(s), and/or substitution(s) with natural or unnatural amino acid(s) or peptidomimetic(s) (e.g., peptide bond isostere(s)) at any one or more of the 37 positions of CNP-37. Non-limiting examples of substitutions that can be made in CNP-37, based on the numbering of CNP-22, include K4R, G5S, G5R, G8S, K10R, G15S, S16Q, M17N, G19R, and combinations thereof.

In one embodiment, the CNP variant peptides is a CNP-38, CNP-37, CNP-36, CNP-35, CNP-34, CNP-33 or CNP-32 that has been modified to comprise a hydrophobic moiety. In various embodiments the hydrophobic moiety is a polyethylene glycol.

Additional CNP variants are disclosed in International Application PCT/US2020/045885, which describes hydrophobic peptide salts of CNP variants useful to treat skeletal dysplasias, and incorporated herein by reference. Still other CNP variants contemplated for use are described in PCT/US2020/051100 (herein incorporated by reference), which discloses CNP sequence variants PGQEHPQARRYR-GAQRRGLSRGCFGLKLDRIGSMSGLGC (SEQ ID NO: 66); PGQEHPNARKYKGANKKGLSKGCFGLKLDRI-GSMSGLGC(SEQ ID NO: 1); PGQEHPNARRYR-GANRRGLSRGCFGLKLDRIGSMSGLGC(SEQ ID NO: 67); and PGQEHPQARKYKGAQKKGLSKGCFGLKL-DRIGSMSGLGC(SEQ ID NO: 68), optionally wherein the variants further comprise an acetyl group. In various embodiments, the acetyl group is on the N-terminus of the peptide. In various embodiments, the peptide further comprises an OH or an NH2 group at the C-terminus. In various embodiments, the variant peptide comprises a conjugate moiety. In various embodiments, the conjugate moiety is on a residue of the CNP cyclic domain or at a site other than the CNP cyclic domain. In various embodiments, the conjugate moiety is on a lysine residue. In various embodiments, the conjugate moiety comprises one or more acid moieties. In various embodiments, the acid moiety is a hydrophobic acid. In various embodiments, the conjugate moiety comprises one or more acid moieties linked to a hydrophilic spacer. In various embodiments, the hydrophilic spacer is any amino acid. In various embodiments, the hydrophilic spacer is gamma glutamic acid (yGlu). In various embodiments, the hydrophilic spacer is OEG (8-amino-3,6-dioxaoctanoic acid). In various embodiments, the hydrophilic spacer is gamma glutamic acid (yGlu) or OEG (8-amino-3,6-dioxaoctanoic acid). In various embodiments, the hydrophilic spacer is gamma glutamic acid (yGlu) linked to one or two or more OEG (8-amino-3,6-dioxaoctanoic acid). In various embodiments, the acid moiety is a fatty acid. Exemplary fatty acids include short chain, medium chain, or long chain fatty acids, or a dicarboxylic fatty acid. In various embodiments, the fatty acid is saturated or unsaturated. Contemplated are C-6 to C-20 fatty acids, including but not limited to, C-6, C-8, C-10, C-12, C-14, C-16, C-18 or C-20 fatty acids, saturated or unsaturated. In various embodiments, the fatty acid is decanoic acid, dodecanoic acid, myristic acid, palmitic acid, stearic acid, arachidic acid, or diacids of the same.

In one embodiment, the CNP variant peptides are modified CNP-37 or CNP-38 peptides having mutation(s)/substitution(s) at the furin cleavage site, designed to improve in vivo resistance to the furin protease, and/or containing glycine or proline-glycine at the N-terminus, designed to improve plasma stability and prevent pyroglutamine formation. Exemplary CNP-37 variants include but are not limited to:

```
[CNP-37(M32N)]
                                            (SEQ ID NO: 40)
QEHPNARKYKGANKKGLSKGCFGLKLDRIGSNSGLGC;

(Met-CNP-37)
                                            (SEQ ID NO: 42)
MQEHPNARKYKGANKKGLSKGCFGLKLDRIGSMSGLGC;

(Pro-CNP-37)
                                            (SEQ ID NO: 41)
PQEHPNARKYKGANKKGLSKGCFGLKLDRIGSMSGLGC;

[Gly-CNP-37(M32N)
                                            (SEQ ID NO: 44)
GQEHPNARKYKGANKKGLSKGCFGLKLDRIGSNSGLGC;

(Pro-Gly-CNP-37)
                                             (SEQ NO: 1)
PGQEHPNARKYKGANKKGLSKGCFGLKLDRIGSMSGLGC;

(Met-Gly-CNP-37)
                                            (SEQ ID NO: 45)
MGQEHPNARKYKGANKKGLSKGCFGLKLDRIGSMSGLGC;
and (Gly-CNP-37)
                                            (SEQ ID NO: 43)
GQEHPNARKYKGANKKGLSKGCFGLKLDRIGSMSGLGC.
```

In certain embodiments, the CNP variants may comprise a synthetic polymeric group. In various embodiments, the variant comprises a synthetic polymeric group coupled to the variant through a hydrolysable linker. In various embodiments, the synthetic polymeric group comprises a hydrophilic polymer moiety. In an embodiment, the hydrophilic polymers are water-soluble so that the CNP peptides conjugated thereto do not precipitate out in an aqueous (e.g., physiological) environment. Further, the hydrophilic polymers are biocompatible, i.e., do not cause injury, toxicity or an immunological reaction in vivo. The hydrophilic polymers can be branched or unbranched. In one embodiment, the hydrophilic polymers are not branched. In various embodiments, the hydrophilic polymer moiety comprises polyethylene glycol (PEG). Various sites of conjugation of CNP variants to a hydrophilic polymer are possible, including but not limited to: (1) only at the N-terminus; (2) only at the C-terminus; (3) only at an internal site (e.g., Lys4 and/or Lys 10); (4) at both the N-terminus and the C-terminus; (5) at the N-terminus and an internal site; and (6) at the C-terminus and an internal site.

Methods for preparing PEGylated CNP variant peptides generally comprise the steps of (a) reacting CNP variant with a PEGylation reagent under conditions suitable for attaching PEG to the CNP peptide (e.g., at the N-terminus), and (b) obtaining the reaction product(s), using techniques known in the art.

Synthesis and Purification of CNP Variant Peptides

In some embodiments, the CNP variant peptides useful herein are produced by recombinant expression, using certain techniques known in the art in certain embodiments. See, e.g., Sambrook, Fritsch & Maniatis, Molecular Cloning: A Laboratory Manual, Second Edition. Cold Spring Harbor Laboratory Press (Cold Spring Harbor, N.Y. (1989)); DNA Cloning: A Practical Approach, Volumes I and II, D. N. Glover, Ed. (1985); and Current Protocols in Molecular Biology, John Wiley & Sons, Inc. (1994).

In certain embodiments, the CNP variant peptides are produced by a recombinant process that comprises culturing in a medium a host cell comprising a first polynucleotide encoding a CNP variant peptide linked to a second polynucleotide encoding a cleavable peptide or protein under conditions that result in expression of a fusion polypeptide encoded by the polynucleotides, wherein the fusion polypeptide comprises the CNP variant peptide directly linked to the cleavable peptide or protein or indirectly linked thereto via a linker. In some embodiments, the host cell is transformed with an expression vector comprising the polynucleotide encoding the CNP variant peptide linked to the polynucleotide encoding the cleavable peptide or protein. In certain embodiments, the fusion polypeptide is expressed as a soluble protein or as an inclusion body. The expressed fusion polypeptide can be isolated from the host cell or culture medium, and the isolated fusion polypeptide can be contacted with a cleaving agent to release the CNP variant peptide.

Methods of producing CNP variant peptides are described in U.S. Pat. Nos. 8,198,242, 8,377,884 and 8,598,121, 9,907,834 and 10,646,550 herein incorporated by reference.

Host cells used to produce CNP variant peptides can be bacterial, yeast, insect, non-mammalian vertebrate, or mammalian cells. Bacterial cells include without limitation *E. coli* cell lines and strains. Non-limiting examples of *E. coli* cell lines and strains include BL21, BL21(DE3), BL21 (DE3)pLysS, BL21(DE3)pGro7, ArcticExpress(DE3), C41 [also called C41(DE3)], C43 [also called C43(DE3)], Origami B(DE3), Origami B(DE3)pLysS, KRX, and Tuner (DE3). In an embodiment, CNP variant peptides and CNP fusion proteins are produced using BL21(DE3) cells. Mammalian cells include, but are not limited to, hamster, monkey, chimpanzee, dog, cat, bovine, porcine, mouse, rat, rabbit, sheep and human cells. The host cells can be immortalized cells (a cell line) or non-immortalized (primary or secondary) cells and can be any of a wide variety of cell types, such as, but not limited to, fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), chondrocytes and other bone-derived cells, and precursors of these somatic cell types. Host cells containing the CNP variant DNA or RNA are cultured under conditions appropriate for growth of the cells, expression of the DNA or RNA and identification/selection of cells expressing the CNP variant peptide.

In certain embodiments, the CNP variant peptides are recombinantly expressed as fusion proteins comprising a CNP variant peptide and a cleavable carrier protein or cleavable tag (e.g., peptide tag), wherein the fusion protein comprises the CNP variant peptide directly linked to the cleavable carrier protein or tag or indirectly linked thereto via a linker. Use of a carrier protein or tag facilitates, e.g., detection, isolation and/or purification of the fusion protein. Cleavable carrier proteins and tags include, but are not limited to, histidine (e.g., hexa-His) tags; human transcription factor TAF12 (TAF12), TAF12 fragments, TAF12 histone fold domain, mutants of TAF12 and fragments thereof, TAF12(C/A), TAF12(D/E), TAF12(4D/4E), TAF12(6D/6E), TAF12(10D/10E), TAF12(C/A & D/E), TAF12(C/A & 4D/4E), TAF12(C/A & 6D/6E), TAF12(C/A & 10D/10E); ketosteroid isomerase (KSI); maltose-binding protein (MBP); ß-galactosidase (ß-Gal); glutathione-S-transferase (GST); thioredoxin (Trx); chitin binding domain (CBD); BMP-2, BMP-2 mutants, BMP-2(C/A); SUMO; and mutants and fragments thereof.

In other embodiments, the CNP variant peptides described herein are synthesized using a peptide synthesizer and purified according to methods known in the art, e.g., according to the methods of Atherton and Sheppard, Solid Phase Peptide Synthesis: a Practical Approach, IRL Press (Oxford, England (1989)).

Methods of Using CNP Variant Peptides

Bone-Related Disorders/Skeletal Dysplasias

Fibroblast growth factors (FGFs) play important roles in bone formation, and mutations in FGF receptor genes (FGFR 1, 2 and 3) give rise to a variety of inherited skeletal malformations (Curr. Biol., 5: 500-507 (1995)). In particular, activating mutations in FGFR-3 are responsible for disorders of the long bones, including achondroplasia, the most common form of human genetic dwarfism (Nature, 371: 252-254 (1994); Cell, 78: 335-342 (1994)), the milder disorder hypochondroplasia (Ann. N.Y. Acad. Sci., 785: 182-187 (1996)), and the more severe and neonatal lethal thanatophoric dysplasia (TD) types I and II (Hum. Mol. Genet., 5: 509-512 (1996); Nat. Genet., 9: 321-328 (1995)). Mouse models overexpressing FGF-2, and consequentially activating FGFR-3, show shortened long bones and macrocephaly (Mol. Biol. Cell, 6: 1861-73 (1995)). Consistent with this model, mice deficient in FGFR-3 show remarkable skeletal overgrowth with wider growth plates (Nature Genet., 12: 390-397 (1996)).

By stimulating matrix production, proliferation and differentiation of chondrocytes and increasing long bone growth, the CNP variant peptides of the disclosure are useful for treating mammals, including humans, suffering from a bone-related disorder, such as a skeletal dysplasia. Non-limiting examples of CNP-responsive bone-related disorders and skeletal dysplasias include achondroplasia, hypochondroplasia, short stature, dwarfism, osteochondrodysplasias, thanatophoric dysplasia, osteogenesis imperfecta, achondrogenesis, chondrodysplasia punctata, homozygous achondroplasia, campomelic dysplasia, congenital lethal hypophosphatasia, perinatal lethal type of osteogenesis imperfecta, short-rib polydactyly syndromes, hypochondroplasia, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, spondyloepimetaphyseal dysplasia, NPR2 mutation, SHOX mutation (Turner's syndrome/Leri Weill), PTPN11 mutations (Noonan's syndrome), and idiopathic short stature. Further, the CNP variants are useful as an adjunct or alternative to growth hormone for treating idiopathic short stature and other skeletal dysplasias.

In addition, the CNP variant peptides are useful for treating other bone-related conditions and disorders, such as rickets, hypophosphatemic rickets [including X-linked hypophosphatemic rickets (also called vitamin D-resistant rickets) and autosomal dominant hypophosphatemic rickets], and osteomalacia [including tumor-induced osteomalacia (also called oncogenic osteomalacia or oncogenic hypophosphatemic osteomalacia)].

In various embodiments, the bone-related disorder, skeletal dysplasia or short stature disorder results from an NPR2 mutation, SHOX mutation (Turner's syndrome/Leri Weill), or PTPN11 mutations (Noonan's syndrome).

In various embodiments, the bone-related disorder, skeletal dysplasia or short stature disorder results from an NPR2 mutation, SHOX mutation (Turner's syndrome/Leri Weill), or PTPN11 mutations (Noonan's syndrome), or insulin growth factor 1 receptor (IGF1R).

In various embodiments, the CNP variants are useful to treat growth plate disorders and short stature, including familial short stature, dominant familial short stature which is also known as dominant inherited short stature, or idiopathic short stature. In various embodiments, the short stature or growth plate disorder is a result of a mutation in collagen (COL2A1, COL11A1, COL9A2, COL10), aggrecan (ACAN), indian hedgehog (IHH), PTPN11, NPR2, NPPC, or FGFR3.

In various embodiments, the growth plate disorder or short stature is associated with one or more mutations in a gene associated with a RASopathy.

In various embodiments, the bone-related disorder, skeletal dysplasia or short stature disorder results from a RASopathy. In various embodiments, the RASopathy is Noonan syndrome, Costello syndrome, Cardiofaciocutaneous syndrome, Neurofibromatosis Type 1, or LEOPARD syndrome.

In one embodiment, the RASopathy is hereditary gingival fibromatosis type 1.

In various embodiments, the CNP variants are useful to treat growth plate disorders and short stature, including familial short stature, dominant familial short stature which is also known as dominant inherited short stature, or idiopathic short stature. In various embodiments, the short stature or growth plate disorder is a result of a mutation in collagen (COL2A1, COL11A1, COL9A2, COL10), aggrecan (ACAN), indian hedgehog (IHH), PTPN11, NPR2, NPPC, FGFR3, or insulin growth factor 1 receptor (IGF1R).

In various embodiments, the short stature is associated with one or more mutations in a gene associated with a RASopathy.

RASopathies are a group of rare genetic conditions caused by mutations in genes of the Ras/mitogen-activated protein kinase (MAPK) pathway. RASopathies are a group of disorders characterized by increased signaling through RAS/MAPK pathway. This pathway leads to downstream activation of the RAF/MEK/ERK pathway. Short stature is a characteristic feature of certain RASopathies. For example, CNP signaling inhibits RAF and leads to decreased MEK and ERK activation.

Treatment of RASopathies are contemplated herein. RASopathies associated with short stature include Noonan syndrome, Costello syndrome, Cardiofaciocutaneous syndrome, Neurofibromatosis Type 1, and LEOPARD syndrome. Hereditary gingival fibromatosis type 1 is also a RASopathy contemplated herein. RASopathy patients (including Noonan syndrome, Costello syndrome, Cardiofaciocutaneous syndrome, Neurofibromatosis Type 1, LEOPARD syndrome, hereditary gingival fibromatosis type 1) include patients with heterozygous variants in one or more of the following genes: BRAF, CBL, HRAS, KRAS, LZTR1, MAP2K1, MAP2K2, MRAS, NF1, NRAS, PPPICB, PTPN11, RAF1, RRAS, RIT1, SHOC2, SOS1, or SOS2 (Tajan et al. Endocr. Rev. 2018;39(5):676-700).

Mutations in multiple genes can cause Noonan syndrome, which is characterized by short stature, heart defects, bleeding problems, and skeletal malformations. Mutations in the PTPN11 gene cause about half of all cases of Noonan's syndrome. SOS1 gene mutations cause an additional 10 to 15 percent, and RAF1 and RIT1 genes each account for about 5 percent of cases. Mutations in other genes each account for a small number of cases. The cause of Noonan syndrome in 15 to 20 percent of people with this disorder is unknown.

The PTPN11, SOS1, RAF1, and RIT1 genes all encode for proteins that are important in the RAS/MAPK cell signaling pathway, which is needed for cell division and growth (proliferation), differentiation, and cell migration. Many of the mutations in the genes associated with Noonan syndrome cause the resulting protein to be turned on (active) and this prolonged activation alters normal RAS/MAPK signaling, which disrupts the regulation of cell growth and division, leading to the characteristic features of Noonan syndrome. See, e.g., Chen et al., Proc Natl Acad Sci USA. 111(31):11473-8, 2014, Romano et al., Pediatrics. 126(4): 746-59, 2010, and Milosavljević et al., Am J Med Genet 170(7):1874-80, 2016. It is contemplated that a subject having mutations that activate the MAPK pathway would benefit from treatment with CNP variants as described herein to improve bone growth and short stature. It is also contemplated that a subject having mutations that activate the MAPK pathway would benefit from treatment with CNP variants as described herein to improve other comorbidities associated with an overactive MAPK pathway in other cells throughout the body where the NPR2 receptor is expressed on its surface.

In certain embodiments, the CNP variant peptides and compositions and formulations described herein are useful for improving one or more of the symptom(s) or physiological consequences of a skeletal dysplasia, wherein the improvement may be increased absolute growth, increased growth velocity, increased qualitative computed tomography (QCT) bone mineral density, improvement in growth plate morphology, increased long bone growth, improvement in spinal morphology, improved elbow joint range of motion and/or decreased sleep apnea. In this regard, it is noted that the terms "improved", "improvement", "increase", "decrease" and grammatical equivalents thereof are all relative terms that when used in relation to a symptom or physiological consequence of a disease state, refer to the state of the symptom or physiological consequence of the disease after treatment with a CNP variant peptide (or composition or formulation comprising the same) of the present invention as compared to the same symptom or physiological consequence of the disease before treatment with a CNP variant peptide (or composition or formulation comprising the same) of the present invention (i.e., as compared to "baseline"). As described above, a "baseline" state can be determined either through measurement of the state in the subject prior to treatment (which can subsequently be compared to the state in the same subject after treatment), or through measurement of that state in a population of subjects suffering from the same affliction that share the same or similar characteristics (e.g., age, sex and/or disease state or progression).

Increasing or Enhancing Growth Velocity

The compositions and formulations of the present disclosure may also be administered for the purpose of enhancing or increasing growth velocity in a subject suffering from skeletal dysplasia. In a preferred embodiment, the subject suffers from achondroplasia. Efficacy of treatment is measured by various parameters. In various embodiments, efficacy is assessed as the change in annualized growth velocity from the baseline period to the intervention period. Efficacy is also assessed as the change in height standard deviations score (SDS), also referred to as a height Z-score, from baseline to end of treatment as measured using the CDC growth curves, and growth velocity SDS is based on the Bone Mineral Density in Childhood Study (Kelly et al., J. Clin. Endocrinol. Metab. 2014;99(6):2104-2112).

Measurements of growth velocity in subjects may be made over time using standard techniques well known in the art. In certain embodiments, measurements of parameters such as standing height, sitting height, weight, head circumference, upper arm length, lower arm (forearm) length, upper leg length, lower leg length (knee to foot), hand length (wrist to end of finger) and/or foot length may be made over a specified period of time to determine the specific rate of growth as measured by any particular parameter (i.e., the growth velocity). Measurements of growth velocity over a specified period of time may be "annualized", wherein the rate of growth calculated over a specific period of time is converted to the expected rate of growth over a period of one year. Measurements of growth velocity in a subject prior to treatment with a CNP variant peptide of the present invention (i.e., a "baseline" growth velocity) may be compared to measurements of growth velocity during or after treatment with a CNP variant peptide of the present invention to determine the effect of treatment on changes in growth velocity in the subject. A "baseline" growth velocity may also be determined from a population of subjects of the same general age, sex and disease status as the individual being treated with a CNP variant peptide of the present invention.

Improvements in growth velocity as measured by assessment of one of more of the parameters described above (e.g., standing height, etc.) induced or caused by treatment of a subject in need thereof with a CNP variant peptide of the present invention (or composition or formulation comprising the same) may be quantitatively measured. In this regard, in certain embodiments, annualized increase or improvement of growth velocity of any particular parameter in a subject treated with a CNP variant of the present invention (or a composition or formulation comprising the same) are at least about 10%, 15%, 20%, 25%, 30%, 35%, 40%, 45%, or 50%, or more above baseline. In certain embodiments, the methods described herein result in an annualized increase in growth velocity as measured by standing height of at least about 10%, 15%, 20%, 25%, 30%, 35%, 40%, 45%, or 50%, or more above baseline. In other embodiments, the methods described herein result in an annualized increase in growth velocity as measured by either sitting height, weight, head circumference, upper arm length, lower arm (forearm) length, upper leg length, lower leg length (knee to foot), hand length (wrist to end of finger) or foot length of at least about 10%, 15%, 20%, 25%, 30%, 35%, 40%, 45%, or 50%, or more above baseline. As described herein, the baseline comparator may be the annualized growth velocity as measured by the specific parameter prior to treatment of the same subject with a CNP variant peptide of the present invention, or may be the growth velocity determined from a population of subjects of the same general age, sex and disease status as the individual being treated with a CNP variant peptide of the present invention.

Anthropometry data relating to proportionality of certain body segments to others may also be obtained from subjects both before and after treatment with a CNP variant peptide to determine whether administration of a CNP variant peptide results in changes in such proportionality. For example, ratios of upper body length (waist to top of head) to lower body length (waist to foot) may be calculated both prior to treatment with a CNP variant peptide (i.e., baseline) and after treatment with a CNP variant peptide to determine whether treatment with the CNP variant peptide has an adverse effect on body proportionality. In younger subjects, e.g., patients 0 to 2 years old, measurement of body length and crown to rump length may take precedence over standing height and sitting height for measurement of annualized growth velocity and Z-score.

Ratios of upper arm to forearm length or upper leg to lower leg (knee to foot) may also be calculated and compared to determine the effect of CNP variant peptide treatment on body proportionality. In a preferred embodiment, administration of a CNP variant peptide to a subject does not result in a significant change in body proportionality as measured by any specific ratio as compared to baseline. In this regard, in certain embodiments, treatment with a CNP variant peptide, or composition or formulation comprising the same, of the present invention results in a change in any of the above described ratios of no more than 0.5, 0.25, 0.20, 0.15, 0.10 or 0.05, preferably no more than 0.05.

In the various methods described herein, it is preferred that administration of the CNP variant peptide or composition or formulation comprising the same not result in an adverse event related to the study drug of grade two or higher, or grade three or higher, in the treated subject. In this regard, techniques for measuring and grading physiological events associated with the treatment of a subject with a compound, and a listing of graded adverse events, maintained by the US National Institute for Health (NIH) under the Common Terminology Criteria for Adverse Events (CTCAE) v5.0 (Quick Reference Guide, Common Terminology Criteria for Adverse Events (CTCAE) Version 5.0 Published: Nov. 27, 2017) which is herein incorporated by reference.

Moreover, in the various methods described herein, it is preferred that administration of the CNP variant peptide or composition or formulation comprising the same not result in a clinically significant change (either increase or decrease as compared to baseline) in one or more of the following physiological parameters; blood hemoglobin concentration, blood platelet number, blood electrolyte concentration, blood urea nitrogen concentration, blood creatinine concentration, blood alkaline phosphatase concentration, blood alanine amino transferase concentration or blood aspartate aminotransferase concentration. By "clinically significant change" is meant a change in any one or more of the above parameters that is observed to result in a detectable/observable, adverse physiological change in the subject's overall health.

Pharmaceutical Compositions and Formulations of CNP Variant Peptides

In additional embodiments, the disclosure contemplates use of pharmaceutical compositions and formulations comprising a CNP variant peptide, and one or more pharmaceutically acceptable excipients, carriers and/or diluents. In certain embodiments, the compositions further comprise one or more other biologically active agents (e.g., inhibitors of proteases, receptor tyrosine kinases, and/or the clearance receptor NPR—C).

Non-limiting examples of excipients, carriers and diluents include vehicles, liquids, buffers, isotonicity agents, additives, stabilizers, preservatives, solubilizers, surfactant, emulsifiers, wetting agents, adjuvants, and so on. The compositions can contain liquids (e.g., water, ethanol); diluents of various buffer content (e.g., Tris-HCl, phosphate, acetate buffers, citrate buffers), pH and ionic strength; detergents and solubilizing agents (e.g., Polysorbate 20, Polysorbate 80); anti-oxidants (e.g., methionine, ascorbic acid, sodium metabisulfite); preservatives (e.g., Thimerosol, benzyl alcohol, m-cresol); and bulking substances (e.g., lactose, mannitol, sucrose). The use of excipients, diluents and carriers in the formulation of pharmaceutical compositions is known in the art; see, e.g., Remington's Pharmaceutical Sciences, 18th Edition, pages 1435-1712, Mack Publishing Co. (Easton, Pennsylvania (1990)), which is incorporated herein by reference in its entirety.

For example, carriers include without limitation diluents, vehicles and adjuvants, as well as implant carriers, and inert, non-toxic solid or liquid fillers and encapsulating materials that do not react with the active ingredient(s). Non-limiting examples of carriers include phosphate buffered saline, physiological saline, water, and emulsions (e.g., oil/water emulsions). A carrier can be a solvent or dispersing medium containing, e.g., ethanol, a polyol (e.g., glycerol, propylene glycol, liquid polyethylene glycol, and the like), a vegetable oil, and mixtures thereof.

In some embodiments, the compositions are liquid formulations. In certain embodiments, the formulations comprise a CNP variant peptide in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml, or from about 2 mg/ml to about 10 mg/ml, or about 2 mg/ml or about 10 mg/ml. In other embodiments, the formulation may be a lyophilized formulation or may be a liquid formulation that was previously reconstituted from a lyophilized formulation.

In further embodiments, the compositions comprise a buffer solution or buffering agent to maintain the pH of a CNP-containing solution or suspension within a desired range. Non-limiting examples of buffer solutions include phosphate buffered saline, Tris buffered saline, and Hank's buffered saline. Buffering agents include without limitation sodium acetate, sodium phosphate, citric acid monohydrate and sodium citrate dihydrate. Mixtures of buffering agents can also be used. In certain embodiments, the buffering agent is acetic acid/acetate or citric acid/citrate. The amount of buffering agent suitable in a composition depends in part on the particular buffer used and the desired pH of the solution or suspension. For example, acetate is a more efficient pH buffer at pH 5 than pH 6, so less acetate may be used in a solution at pH 5 than at pH 6. In some embodiments, the buffering agent has a concentration of about 10 mM±5 mM. In certain embodiments, the pH of a composition is from about pH 3 to about pH 7.5, or from about pH 3.5 to about pH 7, or from about pH 3.5 to about pH 6.5, or from about pH 4 to about pH 6, or from about pH 4 to about pH 5, or is at about pH 5.0±1.0, or is at about pH 5.5±1.0.

In other embodiments, the compositions contain an isotonicity agent to render the solution or suspension isotonic and more compatible for injection. Non-limiting examples of isotonicity agents include NaCl, trehalose, mannitol, dextrose, glucose, glycerin, sorbitol, xylitol, and ethanol. In certain embodiments, the isotonicity agent is trehalose or mannitol, which can be employed individually or in combination. In certain embodiments, trehalose or mannitol is in a concentration of about 160±20 mM, or about 140 mM±20 mM, or about 120±20 mM, or about 100 mM±20 mM, or about 80 mM±20 mM, or about 60 mM±20 mM.

In various embodiments, the compositions may comprise a preservative. Preservatives include, but are not limited to, m-cresol and benzyl alcohol. In certain embodiments, the preservative is in a concentration of about 0.4%±0.2%, or about 1%±0.5%, or about 1.5%±0.5%, or about 2.0%±0.5%. In certain embodiments of the invention, the composition or formulation does not contain a preservative.

In various embodiments, the compositions contain an anti-adsorbent agent (e.g., to mitigate adsorption of a CNP variant to glass or plastic). Anti-adsorbent agents include without limitation benzyl alcohol, polysorbate 20, and polysorbate 80. In certain embodiments, the anti-adsorbent is in a concentration from about 0.001% to about 0.5%, or from about 0.01% to about 0.5%, or from about 0.1% to about 1%, or from about 0.5% to about 1%, or from about 0.5% to about 1.5%, or from about 0.5% to about 2%, or from about 1% to about 2%.

In various embodiments, the compositions comprise a stabilizer. Non-limiting examples of stabilizers include glycerin, glycerol, thioglycerol, methionine, and ascorbic acid and salts thereof. In some embodiments, when the stabilizer is thioglycerol or ascorbic acid or a salt thereof, the stabilizer is in a concentration from about 0.1% to about 1%.

In various embodiments, the compositions contain an antioxidant. An exemplary anti-oxidant is, without limitation, ascorbic acid. In certain embodiments, the molar ratio of antioxidant to CNP variant peptide is from about 0.1:1 to about 15:1, or from about 1:1 to about 15:1, or from about 0.5:1 to about 10:1, or from about 1:1 to about 10:1 or from about 3:1 to about 10:1.

Pharmaceutically acceptable salts can be used in the compositions, including without limitation mineral acid salts (e.g., hydrochloride, hydrobromide, phosphate, sulfate), salts of organic acids (e.g., acetate, propionate, malonate, benzoate, mesylate, tosylate), and salts of amines (e.g., isopropylamine, trimethylamine, dicyclohexylamine, diethanolamine). A thorough discussion of pharmaceutically acceptable salts is found in Remington's Pharmaceutical Sciences, 18th Edition, Mack Publishing Company, (Easton, Pennsylvania (1990)).

Formulations for parenteral administration can be prepared, e.g., as liquid solutions or suspensions, as solid forms suitable for solubilization or suspension in a liquid medium prior to injection, or as emulsions. For example, sterile injectable solutions and suspensions can be formulated according to techniques known in the art using suitable diluents, carriers, solvents (e.g., buffered aqueous solution, Ringer's solution, isotonic sodium chloride solution), dispersing agents, wetting agents, emulsifying agents, suspending agents, and the like. In addition, sterile fixed oils, fatty esters, polyols and/or other inactive ingredients can be used. As further examples, formulations for parenteral administration include aqueous sterile injectable solutions, which can contain antioxidants, buffers, bacteriostats, and solutes that render the formulation isotonic with the blood of the intended recipient; and aqueous and nonaqueous sterile suspensions, which can contain suspending agents and thickening agents.

Exemplary CNP peptide-containing formulations are described in U.S. Pat. Nos. 8,198,242, 8,598,121, 9,907,834 and 10,646,550. Use of CNP formulations having a pH in the range from about 4 to about 6 is contemplated.

In various embodiments, the composition is an extended release composition.

In various embodiments, CNP variant peptides can be formulated in pharmaceutical carriers for administration to subjects affected by skeletal dysplasia. In some embodiments, liquid formulations of CNP variant peptides are formulated according to any combinations of the ingredients and their amounts or concentrations are described below:

| Ingredient Class | Ingredient | Concentration Range |
|---|---|---|
| Active ingredient | CNP variant peptide | 10 mg/mL ± 9.9 mg/mL |
| Buffering agent | Acetic acid/acetate | 10 mM ± 5 mM, or pH 5 ± 1 |
| Buffering agent | Citric acid/citrate | 10 mM ± 5 mM, or pH 5 ± 1 |
| Isotonicity-adjusting agent | NaCl | 140 mM ± 20 mM |
| Isotonicity-adjusting agent | Trehalose; mannitol | 10% ± 5% |
| Preservative | m-Cresol | 0.4% ± 0.1% or 0.2% |

| Ingredient Class | Ingredient | Concentration Range |
|---|---|---|
| Preservative/anti-adsorbent | Benzyl alcohol | 1.5% ± 0.5% |
| Stabilizer | Glycerin (glycerol) | 5%-100% (neat) |
| Stabilizer | Methionine | 0.01%-0.2% |
| Stabilizer | Ascorbic acid/ascorbate salt | 0.1%-1% |
| Stabilizer | Thioglycerol | 0.1%-1% |
| Anti-adsorbent | Polysorbate 20 | 0.001%-0.5% |
| | Polysorbate 80 | 0.001%-0.5% |
| | Benzyl alcohol | 0.5%-1.5% |

Compositions comprising a CNP variant peptide can also be lyophilized formulations. In certain embodiments, the lyophilized formulations comprise a buffer and bulking agent, and optionally an antioxidant. Exemplary buffers include without limitation acetate buffers and citrate buffers. Exemplary bulking agents include without limitation mannitol, sucrose, dextran, lactose, trehalose, and povidone (PVP K24). In certain embodiments, mannitol and/or trehalose is in an amount from about 3% to about 10%, or from about 4% to about 8%, or from about 4% to about 6%. In certain embodiments, sucrose is in an amount from about 6% to about 20%, or from about 6% to about 15%, or from about 8% to about 12%.

In various embodiments, lyophilized formulations of CNP variant peptides are prepared from formulations formulated according to any combinations of the ingredients and their amounts or concentrations described below:

| Ingredient Class | Ingredient | Concentration Range |
|---|---|---|
| Active ingredient | CNP variant | 10 mg/mL ± 9.9 mg/mL |
| Buffering agent | Acetic acid/acetate | 10 mM ± 5 mM, or pH 5 ± 1 |
| Buffering agent | Citric acid/citrate | 10 mM ± 5 mM, or pH 5 ± 1 |
| Isotonicity-adjusting agent/bulking agent | Sorbitol | 5% ± 3% |
| Isotonicity-adjusting agent/bulking agent | Mannitol/Trehalose | 5% ± 3% |
| Isotonicity-adjusting agent/bulking agent | Sucrose | 10% ± 5% |
| Preservative | m-Cresol | 0.4% ± 0.2% |
| Preservative/anti-adsorbent | Benzyl alcohol | 1.5% ± 0.5% |

| Ingredient Class | Ingredient | Concentration Range |
|---|---|---|
| Stabilizer | Glycerin (glycerol) | 5%-100% (neat) |
| Stabilizer | Methionine | 0.01%-0.2% |
| Stabilizer | Ascorbic acid/ascorbate salt | 0.1%-1% |
| Stabilizer | Thioglycerol | 0.1%-1% |
| Anti-adsorbent | Polysorbate 20 | 0.001%-0.5% |
| | Polysorbate 80 | 0.001%-0.5% |
| | Benzyl alcohol | 0.5%-1.5% |

In various embodiments, a formulation comprising a CNP variant peptide has a pH of about 3-7, or about 3-6, or about 3.5-6.5, or about 4-6, or about 4-5, or about 4.5-5.5. In some embodiments, for pH 4-5.5 a suitable buffering agent is acetic acid/acetate (e.g., sodium acetate), and for pH 5.5-6 a suitable buffering agent is citric acid/citrate. Citric acid/citrate (e.g., sodium citrate) is also a suitable buffering agent in the range of pH 3-6 or pH 4-6. In certain embodiments, the buffering agent has a concentration in the formulation of about 2-50 mM, or about 2-40 mM, or about 2-30 mM, or about 5-30 mM, or about 2-20 mM, or about 5-20 mM, or about 5-15 mM.

Also to minimize or avoid deamidation of a CNP variant peptide, water can be removed from the formulation by lyophilization. In some embodiments, lyophilized formulations contain any combinations of the following components: buffer: sodium acetate and acetic acid, or sodium citrate and citric acid; isotonicity/bulking agent: mannitol (e.g., 3-10%, 2-8% or 4-6%); sucrose (e.g., 6-20%, 5-15% or 8-12%); antioxidants: methionine and/or ascorbic acid with molal ratio of each antioxidant to CNP variant peptide from about 0.1:1 to about 1:1, or from about 0.5:1 to about 5:1, or from about 1:1 to about 15:1, or from about 1:1 to about 10:1, or from about 3:1 to about 10:1.

Deamidation can also be minimized or avoided by storing a CNP composition (e.g., a liquid formulation or a lyophilized formulation) at lower temperature, such as at about 5° C., 0° C., −10° C., −20° C., −30° C., −40° C., −50° C., −60° C., −70° C., −80° C., −90° C., or −100° C.

To minimize or avoid oxidation of oxidizable residues (e.g., methionine) in a CNP variant peptide, the variant can be formulated with one or more antioxidants. Exemplary antioxidants include, but are not limited to, methionine, ascorbic acid, and thioglycerol. Oxidation of, e.g., methionine residues can also be minimized or prevented by purging oxygen from a liquid medium (if a liquid formulation) with nitrogen or argon, and/or by purging oxygen from a container or packaging with nitrogen or argon.

In some embodiments, to minimize or prevent adsorption (e.g., adsorption of a CNP variant peptide to plastic or glass), polysorbate 20, polysorbate 80 or benzyl alcohol, or a combination thereof, is added to a CNP formulation. In certain embodiments, each of the anti-adsorbent(s) is in a concentration from about 0.001% to about 0.5%, or from about 0.01% to about 0.5%, or from about 0.1% to about 1%, or from about 0.5% to about 1%, or from about 0.5% to about 1.5%, or from about 0.5% to about 2%, or from about 1% to about 2%. Exemplary range(s) of anti-adsorbent(s) in the formulation include without limitation from about 0.001% to about 0.5% of polysorbate 20, from about 0.001% to about 0.5% of polysorbate 80, and/or from about 0.5% to about 1.5% of benzyl alcohol.

In various embodiments, the formulation comprises citric acid, sodium citrate, trehalose, mannitol, methionine, polysorbate 80, and optionally sterile water for injection (WFI).

The disclosure also provides kits containing, e.g., bottles, vials, ampoules, tubes, cartridges and/or syringes that comprise a liquid (e.g., sterile injectable) formulation or a solid (e.g., lyophilized) formulation. The kits can also contain pharmaceutically acceptable vehicles or carriers (e.g., solvents, solutions and/or buffers) for reconstituting a solid (e.g., lyophilized) formulation into a solution or suspension for administration (e.g., by injection), including without limitation reconstituting a lyophilized formulation in a syringe for injection or for diluting concentrate to a lower concentration. Furthermore, extemporaneous injection solutions and suspensions can be prepared from, e.g., sterile powder, granules, or tablets comprising a CNP-containing composition. The kits can also include dispensing devices, such as aerosol or injection dispensing devices, pen injectors, autoinjectors, needleless injectors, syringes, and/or needles.

Dosages and Frequency of Dosing

As used herein, the term "therapeutically effective amount" of an active agent (e.g., a CNP variant peptide) refers to an amount that provides therapeutic benefit to a patient. The amount may vary from one individual to another and may depend upon a number of factors, including the overall physical condition of the patient. A therapeutically effective amount of a CNP variant peptide can be readily ascertained by one skilled in the art, using publicly available materials and procedures. For example, the amount of a CNP variant peptide used for therapy should give an acceptable rate of growth based on growth charts for children ages 0-17 years with achondroplasia (214 females and 189 males), which list height for age, head circumference, and segmental growth (Horton WA et al., Standard growth curves for achondroplasia, J. Pediatr., 93: 435–8 (1978)). CDC charts can be used to assess weight for age and weight for height or BMI for age. Secondary outcomes with courses that are more chronic in nature can also be measured.

The dosing frequency for a particular individual may vary depending upon various factors, including the disorder being treated and the condition and response of the individual to the therapy. In certain embodiments, a pharmaceutical composition containing a CNP variant peptide is administered to a subject about one time per day, one time per two days, one time per three days, or one time per week, twice per week, three times per week, once every two weeks, or monthly. In one embodiment, for treatment of bone-related disorders (e.g., skeletal dysplasias, including achondroplasia), a daily or weekly dose of a CNP variant peptide is administered to patients until and/or through adulthood.

In certain embodiments, the CNP variant compositions described herein are administered at a dose in the range from about 3, 4, 5, 6, 7, 8, 9 or 10 nmol/kg to about 300 nmol/kg, or from about 20 nmol/kg to about 200 nmol/kg. In some embodiments, the CNP compositions are administered at a dose of about 3, 4, 5, 6, 7, 8, 9, 10, 15, 20, 25, 30, 35, 40, 45, 50, 55, 60, 65, 70, 75, 80, 85, 90, 95, 100, 110, 120, 125, 130, 140, 150, 160, 170, 175,180, 190, 200, 210, 220, 230, 240, 250, 260, 270, 280, 290, 300, 350, 400, 450, 500, 750, 1000, 1250, 1500, 1750 or 2000 nmol/kg or other dose deemed appropriate by the treating physician. In other embodiments, the CNP variant compositions are administered at a dose of about 3, 4, 5, 6, 7, 8, 9, 10, 15, 20, 25, 30, 35, 40, 45, 50, 55, 60, 65, 70, 75, 80, 85, 90, 95, 100, 110, 120, 125, 130, 140, 150, 160, 170, 175, 180, 190, 200, 210, 220, 230, 240, 250, 260, 270, 280, 290, 300, 350, 400, 450, 500, 750, 1000, 1250, 1500, 1750 or 2000 nmol/kg or other dose deemed appropriate by the treating physician. In other embodiments, the CNP variant compositions are administered at a dose of about 3, 4, 5, 6, 7, 8, 9, 10, 15, 20, 25, 30, 40, 50, 60, 70, 80, 90, 100, 110, 120, 130, 140, 150, 160, 170, 180, 190, 200, 250, 300, 350, 400,450, 500, 550, 600, 650, 700, 750, 800, 850, 900, 950 or 1000 mg/kg, or about 0.5, 0.8, 1.0, 1.25, 1.5, 2, 2.5, 3, 3.5, 4, 4.5, 5, 5.5, 6, 6.5, 7, 7.5, 8, 8.5, 9, 9.5 or 10 mg/kg, or other dose deemed appropriate by the treating physician. The doses of CNP or CNP variant described herein can be administered according to the dosing frequency/frequency of administration described herein, including without limitation daily, 2 or 3 times per week, weekly, every 2 weeks, every 3 weeks, monthly, etc. In various embodiments, the CNP or CNP variant is administered daily subcutaneously. In various embodiments, the CNP or CNP variant is administered weekly subcutaneously. In various embodiments, the CNP variant is administered at a dose of 2.5 µg/kg/day to 60 µg/kg/day, 10 µg/kg/day to 45 µg/kg/day, or 15 µg/kg/day to 30 µg/kg/day. In various embodiments, the CNP variant is administered at a dose of 15 µg/kg/day. In various embodiments, the CNP variant is administered at a dose of 30 µg/kg/day. Administration of a CNP variant peptide may occur over an extended period of time, in some cases, over one month, three months, six months, 12 months or more. In various embodiments, treatment may start at 3 months or 6 months, or when a subject is determined to have a skeletal dysplasia, e.g., by genetic testing, and may be continued until the growth plates are closed.

The CNP variants or compositions thereof can also be administered by implantation of a depot at the target site of action (e.g., an abnormal or degenerated joint or cartilage area). Alternatively, the CNP variant can be administered sublingually under the tongue (e.g., sublingual tablet) by transdermal delivery (e.g., by means of a patch on the skin) or orally in the form of micro-spheres, microcapsules, liposomes (uncharged or charged (e.g., cationic)), polymeric microparticles (e.g., polyamides, polylactide, polyglycolide, poly(lactide-glycolide)), microemulsions, and the like.

The CNP variant compositions described herein can be administered to patients in need thereof at therapeutically effective doses to treat, ameliorate or prevent bone-related disorders (e.g., skeletal dysplasias, including achondroplasia). The safety and therapeutic efficacy of the CNP variant can be determined by standard pharmacological procedures in cell cultures or experimental animals, such as, for example, by determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Active agents exhibiting a large therapeutic index are normally preferred.

The frequency of dosing/administration of a CNP variant peptide for a particular subject may vary depending upon various factors, including the disorder being treated and the condition and response of the subject to the therapy. The CNP variant peptide can be administered in a single dose or in multiple doses per dosing. In certain embodiments, the CNP variant peptide is administered, in a single dose or in multiple doses, daily, every other day, every 3 days, 2 times per week, 3 times per week, weekly, bi-weekly, every 3 weeks, monthly, every 6 weeks, every 2 months, every 3 months, or as deemed appropriate by the treating physician.

In some embodiments, a CNP variant peptide is administered so as to allow for periods of growth (e.g., chondrogenesis), followed by a recovery period (e.g., osteogenesis). For example, the CNP variant peptide may be administered intravenously, subcutaneously, intraarticularly or by another mode daily or multiple times per week for a period of time, followed by a period of no treatment, then the cycle is repeated. In some embodiments, the initial period of treatment (e.g., administration of the CNP variant peptide daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the CNP variant peptide is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

Modes of Administration

The CNP variant peptides, or pharmaceutical compositions or formulations comprising them, can be administered to subjects in various ways such as, e.g., by injection subcutaneously, intraarticularly, intravenously, intra-arterially, intraperitoneally, intramuscularly, intradermally, or intrathecally. In one embodiment, the CNP variant peptides are administered by a single subcutaneous, intraarticular, intravenous, intra-arterial, intraperitoneal, intramuscular, intradermal or intrathecal injection once a day, one every other day, once every three days, or once a week.

The CNP variant peptides can also be administered by direct injection at or near the site of disease. Further, the CNP variant peptides can be administered by implantation of a depot at the target site of action (e.g., an abnormal or degenerated joint or cartilage area). Alternatively, the CNP variant peptides can be administered sublingually under the tongue (e.g., sublingual tablet) or by inhalation into the lungs (e.g., inhaler or aerosol spray), by delivery into the nasal cavity (e.g., intranasal spray), by delivery into the eye (e.g., eye drop), or by transdermal delivery (e.g., by means of a patch on the skin). The CNP variant peptides may also be administered orally in the form of microspheres, microcapsules, liposomes (uncharged or charged (e.g., cationic)), polymeric microparticles (e.g., polyamides, polylactide, polyglycolide, poly(lactide-glycolide)), microemulsions, and the like.

A further method of administration is by osmotic pump (e.g., an Alzet pump) or mini-pump (e.g., an Alzet mini-osmotic pump), which allows for controlled, continuous and/or slow-release delivery of the CNP variant peptide or pharmaceutical composition over a pre-determined period. The osmotic pump or mini-pump can be implanted subcutaneously, or near the target site (e.g., the long bones of limbs, the epiphyses, etc.).

It will be apparent to one skilled in the art that the CNP variant peptides or compositions thereof can also be administered by other modes. Determination of the most effective mode of administration of the CNP variant peptides or compositions thereof is within the skill of the skilled artisan.

Biomarkers

For treatment of bone-related disorders, indicators of growth can be measured, such as long bone growth measurements in utero and neonatal and measurements of bone growth biomarkers such as CNP, cGMP, Collagen II, Collagen X, osteocalcin, and Proliferating Cell Nu-clear Antigen (PCNA).

Biomarkers useful for assessing treatment of skeletal dysplasia also include NTproCNP, N terminal fragment of collagen X (CXM), CNP, cGMP, propeptides of collagen type II and fragments thereof, collagen type II and fragments thereof, propeptides of collagen type I and fragments thereof, collagen type I and fragments thereof, osteocalcin, proliferating cell nuclear antigen (PCNA), aggrecan chondroitin sulfate, collagen X, and alkaline phosphatase. Cartilage- and bone-associated biomarkers can be measured in any appropriate biological sample, including but not limited to tissues, blood, serum, plasma, cerebrospinal fluid, synovial fluid and urine. In some embodiments, the biomarkers are measured in blood, plasma or serum from animals undergoing efficacy/pharmacodynamic in vivo studies and/or from the conditioned media of ex vivo studies.

One CNP signaling marker is cGMP (guanosine 3',5' cyclic monophosphate). The level of this intracellular signaling molecule increases after CNP binds to and activates its cognate receptor NPR-B. Elevated levels of cGMP can be measured from cell culture extracts (in vitro) after CNP exposure, conditioned media from bone ex-plant studies (ex vivo) after CNP exposure, and in the plasma (in vivo) within minutes of CNP administration subcutaneously, intravenously, or via other routes of administration known in the art.

Cartilage and bone-specific analytes (or cartilage- and bone-associated markers) can also be measured to assess CNP efficacy. For example, fragments of cleaved collagen type II are a cartilage-specific marker for cartilage turnover. Type II collagen is the major organic constituent of cartilage and fragments of type II collagen (cleaved collagen) are released into circulation, and subsequently secreted into the urine, following cartilage turnover. Cartilage turnover precedes new bone formation.

A bone-specific biomarker for bone formation which can be measured is N-terminal propeptides of type I procollagen (PINP). The synthesis of type I collagen is an important step in bone formation, as type I collagen is the major organic component in bone matrix. During collagen synthesis, propeptides are released from the procollagen molecule and can be detected in serum. In addition, fragments of collagen type I can be measured as a marker for bone resorption.

Other potential biomarkers for cartilage and bone formation and growth include aggrecan chondroitin sulfate (cartilage-specific marker for cartilage turnover), propeptides of type II collagen (cartilage-specific marker for cartilage formation), collagen type I C-telopeptide (CTx), alkaline phosphatase (bone-specific) and osteocalcin (bone-specific marker for bone formation). Cartilage- and bone-associated biomarkers can be measured, e.g., in serum from efficacy/pharmacodynamic in vivo studies and from the conditioned media of ex vivo studies, using commercially available kits. Cartilage- and bone-associated biomarkers can be measured in any appropriate biological sample, including but not limited to tissues, blood, serum, plasma, cerebrospinal fluid, synovial fluid and urine.

In one embodiment, the level of at least one bone- or cartilage-associated biomarker is assayed or measured in a subject that has been administered a CNP variant or composition described herein in order to monitor the effects of the CNP composition on bone and cartilage formation and growth in vivo. For example, an increase in the level of at least one bone- or cartilage-associated biomarker may indicate that administration of a CNP variant or composition has a positive effect on bone growth and is a useful treatment for skeletal dysplasias and other bone- or cartilage-related diseases or disorders associated with decreased CNP activity. Exemplary bone- or cartilage-associated biomarkers include, but are not limited to, CNP (e.g., endogenous levels of CNP), cGMP, propeptides of collagen type II and fragments thereof, collagen type II and fragments thereof, collagen type I C-telopeptide (CTx), osteocalcin, proliferating cell nuclear antigen (PCNA), propeptides of type I procollagen (PINP) and fragments thereof, collagen type I and fragments thereof, collagen X, aggrecan chondroitin sulfate, and alkaline phosphatase. In various embodiments, measured biomarkers include NTproCNP, N terminal fragment of collagen X (CXM), CNP, cGMP, propeptides of collagen type II and fragments thereof, collagen type II and fragments thereof, propeptides of collagen type I and fragments thereof, collagen type I and fragments thereof, osteocalcin, proliferating cell nuclear antigen (PCNA), aggrecan chondroitin sulfate, collagen X, and alkaline phosphatase.

In various embodiments, biomarkers are measured by obtaining a biological sample from a subject who will be administered, is being administered or has been administered a CNP variant. Biomarkers can be measured using techniques known in the art, including, but not limited to, Western Blot, enzyme linked immunosorbant assay (ELISA), and enzymatic activity assay. The biological sample can be blood, serum, urine, or other biological fluids.

Additional aspects and details of the disclosure will be apparent from the following examples, which are intended to be illustrative rather than limiting.

EXAMPLES

Example 1—Phase 2 Trial of CNP Variant in Achondroplasia Patients 0-5 Years Old

In order to determine the effect of CNP variant peptides on symptoms of skeletal dysplasia, such as achondroplasia, and on long bone growth and/or growth velocity (as measured by the rate of increase in the patient's standing height post-treatment as compared to pre-treatment) in younger achondroplasia patients, dose studies were carried out in achondroplaisa (ACH) children less than 2 years old (inclusive) and 2 to 5 years old who have documented ACH, as documented by clinical grounds and confirmed by genetic testing.

Prior to administration of a formulation comprising a CNP variant peptide as described herein. More specifically, Pro-Gly-CNP-37 peptide was formulated into a sterile, preservative-free composition comprising either 2.0 mg/ml CNP peptide in combination with 0.28 mg/ml citric acid monohydrate, 1.08 mg/ml sodium citrate dihydrate, 58.01 mg/ml trehalose dihydrate, 15 mg/ml D-mannitol, 0.73 mg/ml L-methionine and 0.05 mg/ml polysorbate 80, pH 5.5. This liquid composition was reconstituted from an originally lyophilized formulation comprising the described components and was supplied in a sterile, single use, type I untreated borosilicate clear glass vial. This reconstituted liquid formulation was employed in all human clinical treatment studies described herein.

To assess the safety and efficacy of daily SC injections of vosoritide in younger children with ACH a Phase 2, randomized, double-blind, placebo-controlled, global, multi-center from 0 to 5 years old was undertaken (Study 111-206 and extension study 111-208).

Cohort 1—children aged≥24 to <60 months (n≥30 total: three sentinel subjects who receive vosoritide, and at least 27 additional subjects randomized 1:1 to treatment or placebo control), stratified by age (≥24 to <36 months and ≥36 months to <60 months). All subjects Cohort 1: 15 µg/kg/day subcutaneous injection (all subjects).

Cohort 2—children aged≥6 to <24 months (n≥20 total: three sentinel subjects who receive vosoritide, and at least 17 additional subjects randomized 1:1 to treatment or placebo control), stratified by age (≥6 months to <15 months and ≥15 months to <24 months). All subjects in this cohort are treated with 30 µg/kg/day adjusted to 15 µg/kg/day when subjects reach 2 years of age.

Cohort 3—children aged 0 to <6 months (n≥20 total: three sentinel subjects receive vosoritide, and at least 17 additional subjects randomized 1:1 to treatment or placebo control). Treatment begins at ≥3 months to <6 months after 3 months of observation.

Cohort 1 and 2 subjects must have at least a 6-month period of pre-treatment growth assessment immediately before screening, and have one documented measurement of height/body length a minimum of 6 months prior to the screening visit for 111-206. Cohort 3 subjects must have a minimum of 3 months of observation prior to treatment. This observational period can be obtained either (1) via prior enrolment in another related study or (2) via enrollment in this 111-206 for a minimum of 3 months of non-treatment observation prior to commencement of treatment.

Primary endpoints include length/height Z-score at Week 52 and evaluation of any adverse events. Secondary endpoints include AGV at Week 52, Bilateral X-rays of lower extremities, Lumbar spine X-rays, DXA of whole body and spine, AUC0-∞, AUC0-t, $C_{max}$, $T_{max}$, $t_{1/2}$, CL/F, $V_z$/F, Hip monitoring clinical assessments, Bayley-III, WeeFIM, and ITQOL scores, CBCL scores, Anti-vosoritide total antibody (TAb), Anti-vosoritide antibody cross-reactivity with endogenous CNP, ANP, and BNP (TAb), Anti-vosoritide neutralizing antibody (NAb), CXM and bone-specific alkaline phosphatase, Collagen type II (CTX-II), Cyclic guanosine monophosphate (cGMP), anthropometric measurements, upper to lower body segment ratio, upper arm length to lower arm (forearm) length ratio, upper leg length (thigh) to knee to heel length ratio, upper leg length (thigh) to tibial length ratio, and arm span to standing height ratio.

Exploratory imaging assessment data included measurements and morphology of the spine, long bones and extremities, as well as measures of growth plate, bone age, and bone mineral density. Assays include anterior-posterior (AP) x-ray of pelvis for baseline hip assessment; posterior-anterior (PA) radiographs of the left hand and wrist to assess bone age (Greulich, 1971, Stanford University Press.); (Tanner, 1975, Academic Press.), growth plates, hand length, and cortical thickness; AP lower extremity radiograph to assess growth plates, tibial length, cortical thickness, and bowing, AP radiographs of lumbar spine to assess transverse interpedicular distance. Lateral radiographs of lumbar spine to assess thoracolumbar lordosis angle, vertebral morphology, as well as other potential changes related to spinal stenosis, QCT scan of forearm and tibia to assess bone mineral density, growth plate morphology, and bone length are per-formed. This scan can be acquired with a standard CT scanner, calibration phantom, and designated software, using a predetermined low radiation dose protocol, which avoids direct radiation to the head and torso.

Flexion-extension measures of elbow joint range of motion are measured with a goniometer.

Biomarkers are evaluated by change from baseline and include, but are not limited to, assessment for cartilage turnover (CTX-II), chondrocyte and osteoblast activity (bone-specific alkaline phosphatase), bone formation (P1NP), bone turnover (osteocalcin); and markers of CNP bioactivity (cGMP, NT-proCNP, and ANP) as well as additional biomarkers. Samples for blood and urine biochemical markers of collagen and bone turnover, and for markers of CNP activity, are collected at the designated time points.

Adverse events. All patients in each of the above described cohorts were regularly assessed for the presence of adverse events (as defined by Common Terminology Criteria for Adverse Events (CTCAE) (Version 5.0 Published: Nov. 27, 2017) specifically caused by treatment with the CNP variant peptide. No patient in any of the three study cohorts evidenced an adverse event of grade two or higher that was determined to be related to the study drug, demonstrating that treatment of achondroplasia patients with CNP variant peptides does not result in serious adverse physiological events.

All patients in each study cohort are regularly monitored for blood hemoglobin concentration, blood platelet number, blood electrolyte concentration, blood urea nitrogen concentration, blood creatinine concentration, blood alkaline phosphatase concentration, blood alanine amino transferase concentration and blood aspartate aminotransferase concentration.

Each measurement of standing height was converted to age- and sex-appropriate standard deviations score (SDS), also referred to as a height Z-score, by comparison with reference data available for average stature children from the Centre for Disease Control (CDC). Height Z-score, and its changes from baseline at Week 26 and Week 52 was summarized and presented for sentinel subjects by cohort and overall.

AGV, upper to lower body segment ratio, and standing and sitting height were summarized similarly to height Z-score. Results were summarized for sentinel subjects by cohort and overall. Other anthropometric measures (sitting height, head circumference, etc.) were summarized at each time point and were evaluated for changes from baseline). For younger subjects, body length was measured and used in the analyses instead of standing height. Similarly, crown-to-rump was measured instead of sitting height.

44 subjects had enrolled into Study 111-206 and received treatment, four sentinel subjects and 31 randomized subjects in Cohort 1, and 4 sentinel subjects and 16 randomized subjects in Cohort 2. 3 sentinel subjects and 4 randomized subjects were included in Cohort 3. At the first assessment period, in Cohort 1, four sentinels subjects have completed 52 weeks of treatment, while all 26 randomized subjects have completed the Week 13 visit and nine randomized subjects have completed the Week 39 visit. In Cohort 2, two sentinel subjects have completed the Week 26 visit. No subjects had discontinued from the study drug or the 111-206 study at the time of the data-cutoff date. At a later assessment period, 67 subjects had been enrolled and all 37 treated subjects were included in both the safety analysis population and the full analysis set (FAS), which was considered the primary efficacy analysis set. In addition, study 206 and study 208 are both ongoing, and the randomized subjects were still blinded as of the data cutoff point, so the results that are presented below are the results from the sentinel subjects. FIG. 1 provides demographics of the study participants.

Results: 52 Weeks of Treatment

A summary of the results for the sentinel subjects is presented in Table 1.

TABLE 1

Change from Baseline in Annualized Growth Velocity, Height Z-score, and Body Proportion (Sentinel Subjects)

| Endpoint | Analysis Visit [a] | Cohort (n = 4) | Cohort 2 (n = 4) | Cohort 3 (n = 3) |
|---|---|---|---|---|
| AGV (cm/year) [c] | Baseline [b] | 6.21 ± 1.73 (n = 4) | 11.93 ± 1.32 (n = 4) | 24.78 ± 5.39 (n = 3) |
| | Week 26 | 6.90 ± 1.64 (n = 4) | 10.40 ± 2.15 (n = 4) | 14.43 (n = 1) |
| | Change from baseline to Week 26 | 0.69 ± 1.70 (n = 4) | −1.53 ± 3.03 (n = 4) | −5.03 (n = 1) |
| | Week 52 | 6.78 ± 1.00 (n = 4) | 9.17 ± 1.06 (n = 4) | — |
| | Change from baseline to Week 52 | 0.57 ± 0.91 (n = 4) | −2.75 ± 1.65 (n = 4) | — |
| | Week 78 | 6.48 ± 0.90 (n = 4) | 9.39 (n = 1) | — |
| | Change from baseline to Week 78 | 0.27 ± 1.13 (n = 4) | −3.26 (n = 1) | — |
| | Week 104 | 6.45 ± 0.70 (n = 3) | — | — |
| | Change from baseline to Week 104 | −0.27 ± 1.09 (n = 3) | — | — |
| | Baseline | −4.51 ± 0.33 (n = 4) | −4.72 ± 0.53 (n = 4) | −4.18 ± 0.77 (n = 3) |
| | Week 26 | −4.35 ± 0.23 (n = 4) | −4.29 ± 0.65 (n = 4) | −4.39 (n = 1) |
| | Change from baseline to Week 26 | 0.15 ± 0.19 (n = 4) | 0.43 ± 0.69 (n = 4) | 0.08 (n = 1) |
| | Week 52 | −4.16 ± 0.47 (n = 4) | −3.88 ± 0.35 (n = 4) | — |
| | Change from baseline to Week 52 | 0.34 ± 0.27 (n = 4) | 0.84 ± 0.25 (n = 4) | — |
| | Week 78 | −4.06 ± 0.50 (n = 4) | −3.35 (n = 1) | — |
| | Change from baseline to Week 78 | 0.45 ± 0.29 (n = 4) | 0.78 (n = 1) | — |
| | Week 104 | −3.77 ± 0.41 (n = 3) | — | — |
| | Change from baseline to Week 104 | 0.62 ± 0.36 (n = 3) | — | — |
| | Baseline | 2.25 ± 0.36 (n = 4) | 2.56 ± 0.25 (n = 4) | 3.12 ± 0.37 (n = 3) |
| | Week 26 | 2.21 ± 0.35 (n = 4) | 2.49 ± 0.22 (n = 4) | 3.00 (n = 1) |
| | Change from baseline to Week 26 | −0.04 ± 0.06 (n = 4) | −0.07 ± 0.05 (n = 4) | −0.37 (n = 1) |
| | Week 52 | 2.23 ± 0.24 (n = 4) | 2.37 ± 0.21 (n = 4) | — |
| | Change from baseline to Week 52 | −0.02 ± 0.12 (n = 4) | −0.19 ± 0.28 (n = 4) | — |
| | Week 78 | 2.15 ± 0.29 (n = 4) | 2.30 (n = 1) | — |
| | Change from baseline to Week 78 | −0.11 ± 0.08 (n = 4) | −0.29 (n = 1) | — |
| | Week 104 | 2.19 ± 0.22 (n = 3) | — | — |
| | Change from baseline to Week 104 | −0.19 ± 0.10 (n = 3) | — | — |

Mean ± SD, Individual values for 2 or less subjects, —: Not measured AGV: annualized growth velocity.
[a] Period from the start of study 206
[b] For Cohorts 1 and 2, the calculations were based on height data from study 901 over the past 6 months; for Cohort 3, the calculations were based on height data from study 901 over the past 3 months.
[c] AGV at each visit was calculated using height data for the previous 12 months.

Height Z-score Change from Baseline

For Cohort 1 sentinel subjects the mean (SD) baseline height Z-score was −4.51 (0.33). For Cohort 1 sentinel subjects (N=4), the mean (SD) change from Baseline in height Z score at Week 26 was +0.15 (0.19) and at Week 52 was +0.34 (0.27).

For Cohort 2 sentinel subjects the mean (SD) baseline height Z-score was −4.72 (0.53). For Cohort 2 sentinel subjects (N=4), mean (SD) change from Baseline at Week 26 was +0.43 (0.69) and at Week 52 was +0.84 (0.25). For cohort 3, sentinel subjects the mean (SD) baseline height Z-score was −4.18 (0.77). For Cohort 3 sentinel subjects (N=3), the mean (SD) change from Baseline in height Z score at Week 26 was +0.08.

Annualized Growth Velocity Change from Baseline

Baseline AGV was 6.21 cm/year for Cohort 1 sentinel subjects, 11.93 cm/year for Cohort 2 sentinel subjects, and 24.78 cm/yr for Cohort 3. In Cohort 1 sentinel subjects (N=4), following 26 weeks of treatment, there was a mean (SD) increase in AGV from Baseline of 0.69 (1.70) cm/year and after 52 weeks of treatment there was a mean (SD) increase of 0.57 (0.91) cm/year in AGV from Baseline.

In four Cohort 2 sentinel subjects, following 26 weeks of treatment, there was a mean (SD) decrease of 1.53 (3.03) cm/year in AGV from Baseline and of 2.75 (1.65) cm/year in AGV from Baseline at Week 52. In Cohort 3 sentinel subjects, following 26 weeks of treatment, there was a mean (SD) decrease of 5.03 cm/year in AGV from Baseline.

Upper to Lower Body Segment Ratio

There was no change in upper to lower body ratio over time in both cohorts at the initial checkpoint. In Cohort 1 sentinel subjects (N=4), mean (SD) change in upper to lower body segment ratio from Baseline to Week 26 was −0.04 (0.06) and −0.02 (0.12) to Week 52. For Cohort 2 sentinel subjects (N=2), the mean (SD) change in upper to lower body segment ratio from Baseline to Week 26 was −0.07 (0.05) and −0.19 (0.28) cm at Week 52. At later checkpoints, the same effect was noted for Cohort 3, with the change in ratio of −0.37 at week 26.

Standing Height and Sitting Height

In Cohort 1 sentinel subjects (N=4), mean (SD) change in standing height from baseline was 3.38 (0.82) cm at Week 26 and 6.78 (1.12) cm at Week 52. A consistent improvement was noted in standing height over 2 years of treatment in each of the subjects. Mean (SD) change in sitting height from baseline was 1.98 (1.12) cm at Week 26 and 4.69 (0.43) cm at Week 52.

In the Cohort 2 sentinel subjects (N=2), mean (SD) change in standing height from baseline was 5.15 (1.01) cm at Week 26 and 9.22 (0.98) cm at Week 52. Mean (SD) change in sitting height from baseline in 2 sentinel subjects was 3.70 (0.19) cm at Week 26.

Body Proportion Ratios of the Extremities Change from Baseline and Growth Measures Change from Baseline There were no clinically significant changes in body proportions at Weeks 26 and 52. Across all growth measures (head circumference, arm span, upper arm length, lower arm length, lower body length, upper leg length, knee to heel length, and tibial length) there were consistent positive improvements in growth in both Cohort 1 and 2.

In Study 111-206, over 52 weeks of treatment at 15 µg/kg daily, the mean Cmax and AUC0-∞ of ACH subjects aged 2 to 5 years were generally consistent with 15 µg/kg in older ACH subjects (aged 5-18 years), ranging from 3810 to 6860 µg/mL and 118000 to 350000 µg-min/mL, respectively. Median Tmax ranged from 14.0 to 15.5 minutes, and mean t1/2 ranged from 15.2 to 29.3 minutes. Mean CL/F and Vz/F ranged from 82.1 to 150 mL/min/kg and 2650 to 3800 mL/kg respectively. evidence suggesting that at 15 rig/kg, exposure from study 111-206 Cohort 1 subjects aged 2 to <5 years was similar to that from subjects aged 5 to 18 years in study 111-301.

The same dose of 15 µg/kg was used for Cohort 2 sentinels. Analysis of PK data for Cohort 2 indicated that the appropriate dose to achieve the desired exposure is 30 µg/kg/day, subsequent for 3 sentinels were increased to 30 µg/kg/day until the subjects reach 2 years where they were returned to 15 µg/kg dosing. Cohort 3 will be evaluated the same way.

Analysis of the full data set (FAS) for the placebo and Cohorts 1-3 at week 52 is presented below.

TABLE 2

Analysis of Covariance of Height Z-Score at Week 52 (Overall, Cohort 1, 2 and 3)

| Analysis Population | Assessment | Overall Placebo | Overall Vosoritide | Cohort 1 Placebo | Cohort 1 Vosoritide | Cohort 2 Placebo | Cohort 2 Vosoritide | Cohort 3 Placebo | Cohort 3 Vosoritide |
|---|---|---|---|---|---|---|---|---|---|
| FAS (randomized) | N | 32 | 32 | 16 | 15 | 8 | 8 | 8 | 9 |
| | Baseline, mean (SD) | −4.28 (0.26) | −3.79 (0.17) | −5.13 (1.15) | −4.27 (0.81) | −4.21 (1.24) | −3.39 (0.84) | −2.65 (0.28) | −3.34 (0.34) |
| | LSM change from baseline (95% CI) | −0.31 (−0.48, −0.13) | −0.06 (−0.26, 0.15) | −0.06 (−0.28, 0.16) | 0.27 (0.04, 0.50) | −0.19 (−0.58, 0.20) | 0.02 (−0.38, 0.41) | −0.91 (−1.36, −0.45)[c] | −0.68 (−1.21, −0.15)[c] |
| | Difference in LSM (95% CI)[a] | 0.25 (−0.02, 0.53) | | 0.33 (0.00, 0.67) | | 0.21 (−0.37, 0.79) | | 0.23 (−0.45, 0.91)[c] | |
| | p-value[b] | 0.0712 | | 0.0510 | | 0.4427 | | 0.5083 | |
| FAS | N | 32 | 43 | 16 | 19 | 8 | 12 | 8 | 12 |
| | Baseline, mean (SD) | −4.28 (0.26) | −3.88 (0.14) | −5.13 (1.15) | −4.32 (0.73) | −4.21 (1.24) | −3.67 (0.83) | −2.65 (0.28) | −3.39 (0.28) |
| | LSM change from baseline (95% CI) | −0.30 (−0.47, −0.13) | 0.01 (−0.15, 0.17) | −0.03 (−0.24, 0.18) | 0.26 (0.07, 0.45) | −0.17 (−0.53, 0.18) | 0.24 (−0.05, 0.52) | −0.91 (−1.33, −0.49)[c] | −0.64 (−1.08, −0.20)[c] |
| | Difference in LSM (95% CI)[a] | 0.30 (0.07, 0.54) | | 0.29 (−0.01, 0.58) | | 0.41 (−0.06, 0.87) | | 0.27 (−0.34, 0.89)[c] | |
| | p-value[b] | 0.0110 | | 0.0589 | | 0.0804 | | 0.3876[c] | |

CI: confidence interval;
FAS: full analysis set;
SD: standard deviation
[a]Difference is vosoritide minus placebo.
[b]Two-sided p-value.
[c]Based on 10 imputed datasets.
LS means and difference in LS means were obtained from an analysis of covariance model. Model terms included treatment, sex, age stratum, baseline age, baseline AGV and baseline height Z-score.
For participants aged <24 months, body length takes precedence over standing height. Subjects aged <24 months at baseline and >=24 months at Week 52, body length takes precedence.
If there was no height assessment available within the Week 52 analysis visit window, height Z-score at Week 52 was derived based on imputed height.

TABLE 3

Analysis of Covariance of Annualized Growth Velocity at Week 52 (Overall, Cohort 1, 2 and 3)

| Analysis Population | Assessment | Overall Placebo | Overall Vosoritide | Cohort 1 Placebo | Cohort 1 Vosoritide | Cohort 2 Placebo | Cohort 2 Vosoritide | Cohort 3 Placebo | Cohort 3 Vosoritide |
|---|---|---|---|---|---|---|---|---|---|
| FAS (randomized) | N | 32 | 32 | 16 | 15 | 8 | 8 | 8 | 9 |
| | Baseline, mean (SD) | 9.60 (1.37) | 11.06 (1.34) | 4.20 (1.78) | 4.74 (1.68) | 10.55 (4.78) | 11.51 (4.66) | 19.45 (2.67) | 21.19 (0.93) |
| | LSM change from baseline (95% CI) | −2.95 (−3.45, −2.45) | −2.17 (−2.76, −1.58) | 0.89 (0.23, 1.55) | 1.99 (1.31, 2.67) | −3.00 (−3.86, −2.13) | −2.36 (−3.22, −1.50) | −10.14 (−11.48, −8.79)[c] | −9.34 (−10.78, −7.91)[c] |
| | Difference in LSM (95% CI)[a] | 0.78 (0.02, 1.54) | | 1.10 (0.13, 2.07) | | 0.63 (−0.60, 1.87) | | 0.79 (−1.08, 2.67)[c] | |
| | p-value[b] | 0.0452 | | 0.0276 | | 0.2802 | | 0.4072 | |
| FAS | N | 32 | 43 | 16 | 19 | 8 | 12 | 8 | 12 |
| | Baseline, mean (SD) | 9.60 (1.37) | 11.66 (1.19) | 4.20 (1.78) | 5.07 (1.74) | 10.55 (4.78) | 11.66 (4.61) | 19.45 (2.67) | 22.09 (1.07) |
| | LSM change from baseline (95% CI) | −3.32 (−3.81, −2.84) | −2.41 (−2.88, −1.94) | 0.77 (0.14, 1.40) | 1.78 (1.20, 2.35) | −3.14 (−3.96, −2.31) | −2.23 (−2.90, −1.55) | −10.84 (−12.11, −9.57)[c] | −9.79 (−10.97, −8.62)[c] |
| | Difference in LSM (95% CI)[a] | 0.92 (0.24, 1.59) | | 1.00 (0.13, 1.88) | | 0.91 (−0.17, 1.99) | | 1.04 (−0.62, 2.71)[c] | |
| | p-value[b] | 0.0075 | | 0.0256 | | 0.0932 | | 0.2200 | |

Figure 3:
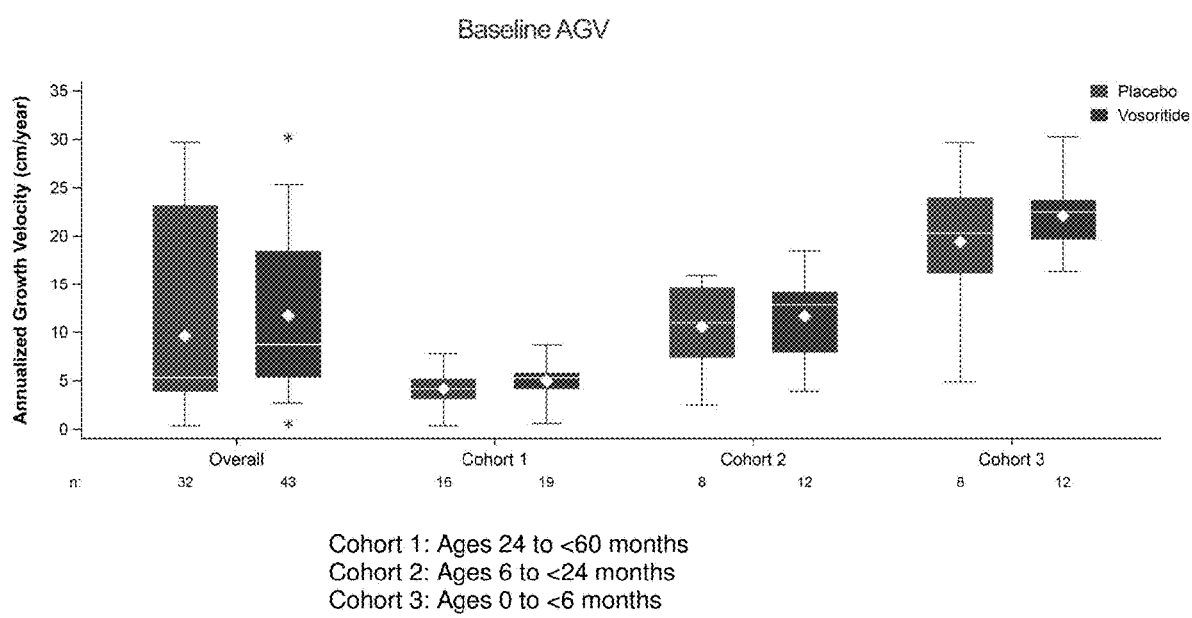
FIG. 3 represents baseline AGV and change in baseline AGV for study Cohorts 1-3 over 52 weeks.
Figure 4:
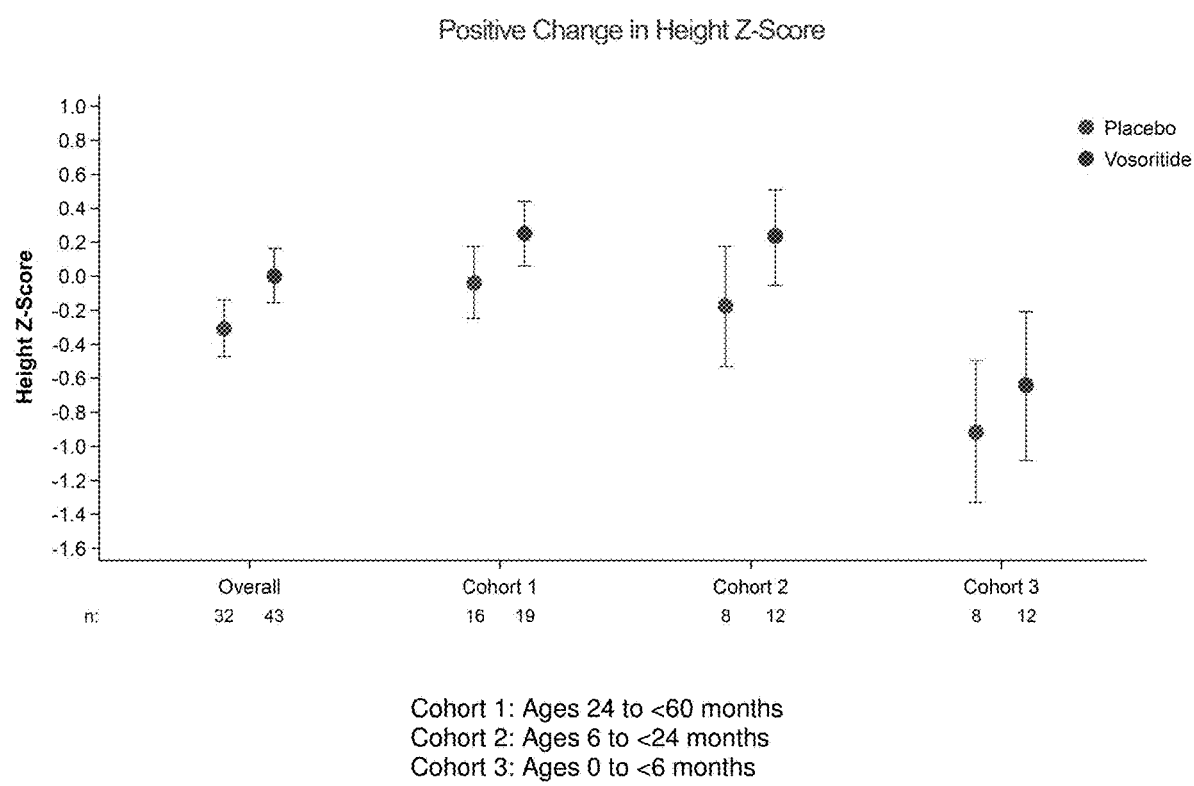
FIG. 4 illustrates the positive change in height Z score over time after 52 weeks of treatment.

FIG. 2 represents baseline Z score for each cohort at 52 weeks of treatment. FIG. 3 represents baseline AGV for each cohort over 52 weeks and FIG. 4 illustrates the positive change in height Z score over time after 52 weeks of treatment. Overall results at week 52 showed that vosoritide (n=43), compared to placebo (n=32): increased height Z-score by 0.30 SD (95% CI 0.07, 0.54), increased AGV by 0.92 cm/year (95% CI 0.24, 1.59), and did not worsen upper-to-lower body segment ratio, which changed by −0.06 (95% CI −0.15, 0.03). The data at week 52 show that vosoritide treatment improves annualized growth velocity, and also improves overall height Z score in treated patients compared to controls in all cohorts.

The pharmacokinetics of vosoritide in the different populations of patients was also analyzed for any change in PK (Table 4). PD information (plasma cGMP and serum CXM) in 4 sentinel subjects and 33 randomized subjects (aged≥24 to <60 months) receiving 30 μg/kg vosoritide was available.

TABLE 4

Pharmacokinetic Parameters at Multiple Subcutaneous Doses of BMN 111

| Cohort (age) | Dose (μg/kg) | Analysis Visit | n | Cmax (ng/mL) | AUC0-t (ng*min/mL) | tmax (min) | t½ (min) | CL/F (mL/min/kg) | Vz/F (mL/kg) |
|---|---|---|---|---|---|---|---|---|---|
| Cohort 1 (24 to <60 months) | 15 | Day 1 | 3 | 4.47 ± 3.30 | 167 ± 110 | 15.0 [15.0, 15.0] | 21.9 ± 3.4 | 111 ± 58.6 | 3700 ± 2410 |
| | | Week 13 | 4 | 3.81 ± 1.67 | 114 ± 64.3 | 15.5 [15.0, 16.0] | 15.2 ± 2.7 | 150 ± 58.5 | 3240 ± 1180 |
| | | Week 26 | 4 | 6.86 ± 4.59 | 327 ± 336 | 15.0 [15.0, 17.0] | 29.3 ± 11.0 | 82.1 ± 57.6 | 3800 ± 3950 |
| | | Week 39 | 4 | 4.98 ± 1.33 | 204 ± 123 | 15.0 [15.0, 21.0] | 27.1 ± 9.0 | 90.3 ± 51.6 | 3170 ± 1350 |
| | | Week 52 | 4 | 5.65 ± 3.01 | 218 ± 138 | 14.0 [7.0, 17.0] | 21.8 ± 4.2 | 85.7 ± 44.4 | 2650 ± 1470 |
| Cohort 2 (6 months to <24 months) | 15 | Day 1 | 3 | 2.84 ± 1.23 | 65.9 ± 33.6 | 15.0 [4.0, 15.0] | 26.1 [a] | 147 [a] | 5550 [a] |
| | | Week 26 | 1 | 10.1 | 398 | 17.0 | 37.6 | 35.4 | 1920 |
| | | Week 39 | 2 | 1.01, 4.39 | 29.9, 229 | 5.0, 35.0 | 22.1 [a] | 63.1 [a] | 2010 [a] |
| | | Week 52 | 2 | 1.01, 2.87 | 17.7, 77.1 | 5.0, 15.0 | 12.5 [a] | 182 [a] | 3290 [a] |
| | 30 | Week 13 | 3 | 12.5 ± 9.19 | 530 ± 370 | 13.0 [5.0, 16.0] | 25.8 ± 4.67 | 77.3 ± 54.2 | 2740 ± 1820 |
| | | Week 26 | 1 | 8.96 | 243 | 6.0 | 6.41 | 123 | 1130 |
| | | Week 39 | 1 | 6.18 | 333 | 15.0 | 22.3 | 86.0 | 2770 |
| | | Week 52 | 1 | 17.6 | 798 | 14.0 | 22.6 | 35.9 | 1170 |
| Cohort 3 (birth to <6 months) | 30 | Day 1 | 3 | 12.3 ± 3.68 | 372 ± 119 | 5.0 [5.0, 13.0] | 60.4 ± 14.9 | 82.0 ± 25.9 | 6800 ± 577 |
| | | Week 13 | 1 | 16.4 | 489 | 5.0 | 23.3 | 59.3 | 1990 |
| | | Week 39 | 1 | 23.6 | 638 | 12.0 | — | — | — |

Mean ± SD, tmax: Median [minimum, maximum], Individual values for 2 or less subjects, —: uncalculated Cmax: maximum plasma concentration, AUC0-t: area under the plasma concentration-time curve from time 0 to t after administration, tmax: time taken to reach the maximum plasma concentration, t½: elimination half-life at terminal phase, CL/F: apparent total body clearance, Vz/F: apparent volume of distribution
[a] n=1

Table 5 shows the changes from baseline at each assessment time point in the urine cGMP/Cr, and Table 6 shows the changes over time from baseline in the serum CXM. The PD parameters were analyzed only in the sentinel subjects in Cohorts 1 and 2.

TABLE 5

Change from Pre-dose in Urinary cGMP/Cr at Each Evaluation Time Point

| Cohort (age) | Dose (µg/kg) | Collection Time | Day 1 | Week 13 | Week 26 | Week 39 | Week 52 |
|---|---|---|---|---|---|---|---|
| Cohort 1 (24 to <60 months) | 15 | pre-dose | 4620 ± 1730 (4) | 3350 ± 515 (4) | 3290 ± 917 (4) | 3420 ± 1230 (4) | 3290 ± 400 (3) |
| | | 2-4 hr post dose | 4880 ± 6710 (4) | 2450 ± 1130 (4) | 6290 ± 4790 (4) | 7620 ± 4220 (4) | 4820 ± 4110 (3) |
| Cohort 2 (6 months to <24 months) | 15 | pre-dose | 6770 ± 3440 (3) | 9020 (1) | 4940 (1) | — | — |
| | | 2-4 hr post dose | -1260 ± 2230 (3) | -1260 (1) | 6040 (1) | — | — |
| | 30 | pre-dose | — | 3340 (1) | 5600 ± 1120 (3) | 8900 (1) | — |
| | | 2-4 hr post dose | — | 10300 (1) | 5090 ± 5140 (3) | 4910 (1) | — |

Mean ± SD(n), Individual values for 2 or less subjects, —: uncalculated, unit: pmol cGMP/mg Cr
a) Evaluated using values approximately 2 to 4 hours after administration.

TABLE 6

Change from Baseline in Serum CXM [a] at Each Evaluation Time Point

| Cohort | Dose (µg/kg) | Baseline | Day 8 | Week 6 | Week 20 | Week 39 |
|---|---|---|---|---|---|---|
| Cohort 1 (24 to <60 months) | 15 | 8050 ± 1017 (4) | 3645 ± 4392 (4) | 10325 ± 7962 (4) | 5750 ± 2859 (4) | 4880 ± 3724 (4) |
| Cohort 2 (6 months to <24 months) | 15 | 8920 ± 3662 (4) | 5180 ± 2963 (4) | 2325 ± 1633 (4) | 10300 (1) | — |
| | 30 | — | — | — | -2790, 6210 (2) | — |

Mean ± SD (n), Individual values for 2 or less subjects, —: uncalculated ` unit: pg/mL
[a] Serum CXM was evaluated using values prior to BMN 111 administration.

Increases in post-dose plasma cGMP concentrations were observed, which remained constant over the time period of 52 weeks and were similar to the changes observed in older age group. CXM (mean and median) on vosoritide was increased in serum throughout the study (over up-to 39 weeks) compared to baseline and placebo. However, values overlapped considerably between vosoritide and placebo. High variability was noted in the measured parameters.

An updated blinded analysis in Cohort 1 subjects (19 vosoritide-treated subjects and 16 placebo-treated subjects aged≥24 to <60 months) showed that levels in serum CXM (averaged across all visits and per treatment) were roughly similar to those observed in older children (i.e. study 111-301) for the respective treatment.

Results: Greater Than 100 Weeks of Treatment

Updated results for subjects treated over 100 weeks demonstrated similar results as at week 52. Subjects in Cohort 1 (N=4) have received vosoritide for a median of 978 days (range: 921 to 1012 days) and in Cohort 2 (N=4) for a median of 733.5 days (range: 706 to 741 days). All sentinel subjects in Cohort 1 had treatment follow up for at least 130 weeks across the two studies 111-206/208 and in Cohort 2 up to Week 104; of note, one subject in Cohort 2 did not have a height assessment at the Week 104 visit as the visit was scheduled post the data cut-off date.

Height Z-Score

In Cohort 1 sentinels, the reduction in height deficit as evaluated by the height Z-score was sustained with vosoritide treatment over 2.5 years. At Week 104, two of the three sentinel subjects showed an improvement in the height Z-scores of +0.77 SDS and +0.86 SDS, while an improvement of +0.27 SDS (at Week 78) and +0.20 SDS was noted in the other two subjects. Cohort 1 exhibited mean (standard deviation [SD]) change from baseline at Week 52 (N=4) of +0.34 (0.27) standard deviation score (SDS), at Week 104 (N=3) of +0.62 (0.36) SDS, and at Week 130 (N=4) of +0.49 (0.34) SDS. For Cohort 2 sentinels, the mean (SD) change from baseline in height Z-score at Week 52 (N=4) was +0.84 (0.25) SDS and was sustained at Week 104 (N=3) with a mean (SD) change from baseline of +0.69 (0.55) SDS.

AGV

In Cohort 1 sentinels the mean (SD) AGV at baseline was 6.21 (1.73) cm/year. The AGV at Week 104 in 2 subjects and Week 78 for 1 subject was higher than the AGV at Baseline; with only a slight decline noted in the fourth subject at Week 104. The subject with the decline in the AGV had a high baseline AGV and was youngest in the Cohort; the decline in the AGV is likely due to the subject being in the steeper curve of the growth decline. The mean (SD) AGV in the first year of treatment in 111-206 remained at 6.78 (1.00) cm/year and in the second year of treatment in 111-208 was 5.85 (0.39) cm/year. In the Cohort 2 sentinels, the mean (SD) AGV at baseline was 11.93 (1.32) cm/year, in the first year of treatment was 9.17 (1.06) and was 6.55 (0.38) in the second year of treatment. This decline in AGV is not as pronounced as would be expected in the untreated children with ACH of this age range, thus illustrating positive effect of vosoritide on growth velocity.

Standing Height/Body Length

For Cohort 1 sentinels, at week 104, a consistent reduction was noted in upper to lower body segment ratios in each of the subjects. The mean (SD) increase in standing height from baseline at Week 52 was 6.78 (1.12) cm, at Week 104 was 12.91 (1.61) and at Week 130 was 15.28 (1.39). In Cohort 2 sentinels, mean (SD) change in standing height from baseline was 9.22 (0.98) cm at Week 52 and at Week 104 was 15.76 (1.42).

Upper to Lower Body Ratio

In Cohort 1 sentinels, there was a reduction in the upper to lower body segment ratio over time with treatment with mean (SD) change in the ratio from baseline at Week 52 of −0.02 (0.12), at Week 104 (N=3) of −0.19 (0.10), and at Week 130 (N=4) of −0.19 (0.14). In Cohort 2 sentinels, the mean (SD) reduction in the upper to lower body segment ratio at Week 52 (N=4) was −0.19 (0.28) with further decline observed at Week 104 (N=3), showing a mean (SD) change from baseline of −0.33 (0.20).

Based on biological/mechanistic considerations, vosoritide is expected to exert favorable effects in all patients with ACH as long as their growth plates are open, although the benefit in young patients with a higher growth potential is likely greater than in older children.

Based upon the human clinical data described above, daily subcutaneously administered doses of 30 μg/kg/day to child and infant achondroplasia patients will also be tested for efficacy and safety as described above. It is fully expected that such administration regimes will provide both efficacious and safe for the treatment of achondroplasia in human patients.

Numerous modifications and variations to the disclosure, as set forth in the embodiments and illustrative examples described herein, are expected to occur to those skilled in the art. Consequently only such limitations as appear in the appended claims should be placed on the disclosure.

What is claimed is:

1. A method of treating skeletal dysplasia in a subject about 0 month to about 2 years old comprising administering to the subject a composition comprising a C-type natriuretic peptide (CNP) variant in an amount effective to treat the skeletal dysplasia in the subject, wherein the CNP variant is selected from the group consisting of:

(Pro-Gly-CNP37)
(SEQ ID NO: 1)
PGQEHPNARKYKGANKKGLSKGCFGLKLDRIGSMSGLGC;

(Gly-CNP53)
(SEQ ID NO: 2)
GDLRVDTKSRAAWARLLQEHPNARKYKGANKKGLSKGCFGLKLDRIGSMSGLGC;

(Pro-CNP53)
(SEQ ID NO: 3)
PDLRVDTKSRAAWARLLQEHPNARKYKGANKKGLSKGCFGLKLDRIGSMSGLGC;

(Met-CNP53)
(SEQ ID NO: 4)
MDLRVDTKSRAAWARLLQEHPNARKYKGANKKGLSKGCFGLKLDRIGSMSGLGC;

[CNP-53(M48N)]
(SEQ ID NO:)
DLRVDTKSRAAWARLLQEHPNARKYKGANKKGLSKGCFGLKLDRIGSNSGLGC;

(CNP-52)
(SEQ ID NO: 6)
LRVDTKSRAAWARLLQEHPNARKYKGANKKGLSKGCFGLKLDRIGSMSGLGC;

(CNP-51)
(SEQ ID NO: 7)
RVDTKSRAAWARLLQEHPNARKYKGANKKGLSKGCFGLKLDRIGSMSGLGC;

(CNP-50)
(SEQ ID NO: 8)
VDTKSRAAWARLLQEHPNARKYKGANKKGLSKGCFGLKLDRIGSMSGLGC;

(CNP-49)
(SEQ ID NO: 9)
DTKSRAAWARLLQEHPNARKYKGANKKGLSKGCFGLKLDRIGSMSGLGC;

(CNP-48)
(SEQ ID NO: 10)
TKSRAAWARLLQEHPNARKYKGANKKGLSKGCFGLKLDRIGSMSGLGC;

(CNP-47)
(SEQ ID NO: 11)
KSRAAWARLLQEHPNARKYKGANKKGLSKGCFGLKLDRIGSMSGLGC;

(CNP-46)
(SEQ ID NO: 12)
SRAAWARLLQEHPNARKYKGANKKGLSKGCFGLKLDRIGSMSGLGC;

(CNP-45)
(SEQ ID NO: 13)
RAAWARLLQEHPNARKYKGANKKGLSKGCFGLKLDRIGSMSGLGC;

(CNP-44)

(SEQ ID NO: 14)
AAWARLLQEHPNARKYKGANKKGLSKGCFGLKLDRIGSMSGLGC;

(CNP-43)

(SEQ ID NO: 15)
AWARLLQEHPNARKYKGANKKGLSKGCFGLKLDRIGSMSGLGC;

(CNP-42)

(SEQ ID NO:16)
WARLLQEHPNARKYKGANKKGLSKGCFGLKLDRIGSMSGLGC;

(CNP-41)

(SEQ ID NO: 17)
ARLLQEHPNARKYKGANKKGLSKGCFGLKLDRIGSMSGLGC;

(CNP-40)

(SEQ ID NO: 18)
RLLQEHPNARKYKGANKKGLSKGCFGLKLDRIGSMSGLGC;

(CNP-39)

(SEQ ID NO: 19)
LLQEHPNARKYKGANKKGLSKGCFGLKLDRIGSMSGLGC;

(CNP-38)

(SEQ ID NO: 20)
LQEHPNARKYKGANKKGLSKGCFGLKLDRIGSMSGLGC;

(CNP-37)

(SEQ ID NO: 21)
QEHPNARKYKGANKKGLSKGCFGLKLDRIGSMSGLGC;

(CNP-36)

(SEQ ID NO: 22)
EHPNARKYKGANKKGLSKGCFGLKLDRIGSMSGLGC;

(CNP-35)

(SEQ ID NO: 23)
HPNARKYKGANKKGLSKGCFGLKLDRIGSMSGLGC;

(CNP-34)

(SEQ ID NO: 24)
PNARKYKGANKKGLSKGCFGLKLDRIGSMSGLGC;

(CNP-33)

(SEQ ID NO: 25)
NARKYKGANKKGLSKGCFGLKLDRIGSMSGLGC;

(CNP-32)

(SEQ ID NO: 26)
ARKYKGANKKGLSKGCFGLKLDRIGSMSGLGC;

(CNP-31)

(SEQ ID NO: 27)
RKYKGANKKGLSKGCFGLKLDRIGSMSGLGC;

(CNP-30)

(SEQ ID NO: 28)
KYKGANKKGLSKGCFGLKLDRIGSMSGLGC;

(CNP-29)

(SEQ ID NO: 29)
YKGANKKGLSKGCFGLKLDRIGSMSGLGC;

(CNP-28)

(SEQ ID NO: 30)
KGANKKGLSKGCFGLKLDRIGSMSGLGC;

(CNP-27)

(SEQ ID NO: 31)
GANKKGLSKGCFGLKLDRIGSMSGLGC;

(CNP-26)

(SEQ ID NO: 32)
ANKKGLSKGCFGLKLDRIGSMSGLGC;

(CNP-25)

(SEQ ID NO: 33)
NKKGLSKGCFGLKLDRIGSMSGLGC;

(CNP-24)

(SEQ ID NO: 34)
KKGLSKGCFGLKLDRIGSMSGLGC;

(CNP-23)

(SEQ ID NO: 35)
KGLSKGCFGLKLDRIGSMSGLGC;

(CNP-21)

(SEQ ID NO: 36)
LSKGCFGLKLDRIGSMSGLGC;

(CNP-20)

(SEQ ID NO: 37)
SKGCFGLKLDRIGSMSGLGC;

(CNP-19)

(SEQ ID NO: 38)
KGCFGLKLDRIGSMSGLGC;

(CNP-18)

(SEQ ID NO: 39)
GCFGLKLDRIGSMSGLGC;

[CNP37(M32N)

(SEQ ID NO: 40)
QEHPNARKYKGANKKGLSKGCFGLKLDRIGSNSGLGC;

(Pro-CNP37)

(SEQ ID NO: 41)
PQEHPNARKYKGANKKGLSKGCFGLKLDRIGSMSGLGC;

(Met-CNP37)

(SEQ ID NO: 42)
MQEHPNARKYKGANKKGLSKGCFGLKLDRIGSMSGLGC;

(Gly-CNP37)

(SEQ ID NO: 43)
GQEHPNARKYKGANKKGLSKGCFGLKLDRIGSMSGLGC;

[Gly-CNP37(M32N)]

(SEQ ID NO: 44)
GQEHPNARKYKGANKKGLSKGCFGLKLDRIGSNSGLGC;

(Met-Gly-CNP37)

(SEQ ID NO: 45)
MGQEHPNARKYKGANKKGLSKGCFGLKLDRIGSMSGLGC;

(HSA-CNP27)

(SEQ ID NO: 46)
GHKSEVAHRFKGANKKGLSKGCFGLKLDRIGSMSGLGC;

[HSA-CNP27 (M22N)]

(SEQ ID NO: 47)
GHKSEVAHRFKGANKKGLSKGCFGLKLDRIGSNSGLGC;

(Pro-HSA-CNP27)

(SEQ ID NO: 48)
PGHKSEVAHRFKGANKKGLSKGCFGLKLDRIGSMSGLGC;

(Met-HSA-CNP27)

(SEQ ID NO: 49)
MGHKSEVAHRFKGANKKGLSKGCFGLKLDRIGSMSGLGC;

[CNP27(K4, 5, 9R)]

(SEQ ID NO: 50)
GANRRGLSRGCFGLKLDRIGSMSGLGC;

[CNP27(K4, 5, 9R, M22N)]

(SEQ ID NO: 51)
GANRRGLSRGCFGLKLDRIGSNSGLGC;

[Pro-CNP27(K4, 5, 9R)]

(SEQ ID NO: 52)
PGANRRGLSRGCFGLKLDRIGSMSGLGC;

[Met-CNP27(K4, 5, 9R)]

(SEQ ID NO: 53)
MGANRRGLSRGCFGLKLDRIGSMSGLGC;

```
[PEG1 K-CNP27(K4, 5, 9R)]
                                              (SEQ ID NO: 54)
PEG1K-GANRRGLSRGCFGLKLDRIGSMSGLGC;

[PEG1 K-CNP27(K4, 5, 9R, M22N)]
                                              (SEQ ID NO: 55)
PEG1K-GANRRGLSRGCFGLKLDRIGSNSGLGC;

[PEG1K-Pro-CNP27(K4, 5, 9R)]
                                              (SEQ ID NO: 56)
PEG1K-PGANRRGLSRGCFGLKLDRIGSMSGLGC;

[PEG1 K-Met-CNP27(K4, 5, 9R)]
                                              (SEQ ID NO: 57)
PEG1K-MGANRRGLSRGCFGLKLDRIGSMSGLGC;

[PEO12-CNP27(K4, 5, 9R)]
                                              (SEQ ID NO: 58)
PEO12-GANRRGLSRGCFGLKLDRIGSMSGLGC;

[PEO12-CNP27(K4, 5, 9R, M22N)]
                                              (SEQ ID NO: 59)
PEO12-GANRRGLSRGCFGLKLDRIGSNSGLGC;

[PEO12-Pro-CNP27(K4, 5, 9R)]
                                              (SEQ ID NO: 60)
PEO12-PGANRRGLSRGCFGLKLDRIGSMSGLGC;

[PEO12-Met-CNP27(K4, 5, 9R)]
                                              (SEQ ID NO: 61)
PEO12-MGANRRGLSRGCFGLKLDRIGSMSGLGC;

[PEO24-CNP27(K4, 5, 9R)]
                                              (SEQ ID NO: 62)
PEO24-GANRRGLSRGCFGLKLDRIGSMSGLGC;

[PEO24-CNP27(K4, 5, 9R, M22N)]
                                              (SEQ ID NO: 63)
PEO24-GANRRGLSRGCFGLKLDRIGSNSGLGC;

[PEO24-Pro-CNP27(K4, 5, 9R)]
                                              (SEQ ID NO: 64)
PEO24-PGANRRGLSRGCFGLKLDRIGSMSGLGC;
and

[PEO24-Met-CNP27(K4, 5, 9R)]
                                              (SEQ ID NO: 65)
PEO24-MGANRRGLSRGCFGLKLDRIGSMSGLGC.
```

2. The method of claim 1, wherein
(a) said composition is administered once daily;
(b) said composition is administered once daily over a period of at least 6 months; or
(c) said composition is administered once daily over a period of at least 12 months.

3. The method of claim 1, wherein the composition is administered to the subject via subcutaneous administration.

4. The method of claim 1, wherein the composition is administered daily, every other day, 3 times weekly, 2 times weekly, or once weekly.

5. The method of claim 1, wherein the composition is administered at a dose of 30 µg/kg.

6. The method of claim 1, wherein the subject is about 6 months to about 2 years old.

7. The method of claim 1, wherein the subject is about 0 to about 6 months old.

8. The method of claim 5, wherein the dosage may be decreased to 15 µg/kg when the subject is 2 years old.

9. The method of claim 1, wherein the skeletal dysplasia is selected from the group consisting of hypophosphatemic rickets, achondroplasia, hypochondroplasia, short stature, dwarfism, osteochondrodysplasias, thanatophoric dysplasia, osteogenesis imperfecta, achondrogenesis, chondrodysplasia punctata, homozygous achondrogenesis, campomelic dysplasia, congenital lethal hypophosphatasia, perinatal lethal type of osteogenesis imperfecta, short-rib polydactyly syndromes, hypochondroplasia, rhizomelic type of chondrodysplasia punctata, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, spondyloepimetaphyseal dysplasia, NPR2 mutation, SHOX mutation, Turner's syndrome/Leri Weill, PTPN11 mutations, Noonan's syndrome, and idiopathic short stature.

10. The method of claim 3, wherein the skeletal dysplasia is achondroplasia.

11. The method of claim 1, wherein the composition further comprises one or more pharmaceutical excipients.

12. The method of claim 11, wherein the composition comprises citric acid monohydrate, sodium citrate dihydrate, trehalose dihydrate, D-mannitol, L-methionine and polysorbate 80.

13. The method of claim 1, wherein the CNP variant is selected from the group consisting of

```
(Pro-Gly-CNP-37)
                                               (SEQ ID NO: 1)
PGQEHPNARKYKGANKKGLSKGCFGLKLDRIGSMSGLGC;

(Gly-CNP-37)
                                              (SEQ ID NO: 43)
GQEHPNARKYKGANKKGLSKGCFGLKLDRIGSMSGLGC;

(CNP-38)
                                              (SEQ ID NO: 20)
LQEHPNARKYKGANKKGLSKGCFGLKLDRIGSMSGLGC;

[CNP-37(M32N)]
                                              (SEQ ID NO: 40)
QEHPNARKYKGANKKGLSKGCFGLKLDRIGSNSGLGC;

(Met-CNP-37)
                                              (SEQ ID NO: 42)
MQEHPNARKYKGANKKGLSKGCFGLKLDRIGSMSGLGC;

(Pro-CNP-37)
                                              (SEQ ID NO: 41)
PQEHPNARKYKGANKKGLSKGCFGLKLDRIGSMSGLGC;

[Gly-CNP-37(M32N)
                                              (SEQ ID NO: 44)
GQEHPNARKYKGANKKGLSKGCFGLKLDRIGSNSGLGC;

(Met-Gly-CNP-37)
                                              (SEQ ID NO: 45)
MGQEHPNARKYKGANKKGLSKGCFGLKLDRIGSMSGLGC;

(CNP-37)
                                              (SEQ ID NO: 21)
QEHPNARKYKGANKKGLSKGCFGLKLDRIGSMSGLGC;

(CNP-36)
                                              (SEQ ID NO: 22)
EHPNARKYKGANKKGLSKGCFGLKLDRIGSMSGLGC;

(CNP-35)
                                              (SEQ ID NO: 23)
HPNARKYKGANKKGLSKGCFGLKLDRIGSMSGLGC;
and (CNP-34)
                                              (SEQ ID NO: 24)
PNARKYKGANKKGLSKGCFGLKLDRIGSMSGLGC.
```

14. The method of claim 1, wherein the CNP variant is selected from the group consisting of

```
                                        (SEQ ID NO: 1)
PGQEHPNARKYKGANKKGLSKGCFGLKLDRIGSMSGLGC
(Pro-Gly-CNP-37);
and (SEQ ID NO: 20)
LQEHPNARKYKGANKKGLSKGCFGLKLDRIGSMSGLGC (CNP-38).
```

\* \* \* \* \*

UNITED STATES PATENT AND TRADEMARK OFFICE
CERTIFICATE OF CORRECTION

PATENT NO. : 12,233,106 B2
APPLICATION NO. : 17/811748
DATED : February 25, 2025
INVENTOR(S) : Jonathan Day et al.

Page 1 of 1

It is certified that error appears in the above-identified patent and that said Letters Patent is hereby corrected as shown below:

On the Title Page

Item [57], Line 1, "treatment" should be -- Treatment --.

In the Claims

Column 63, Line 63, "(SEQ ID NO:)" should be -- (SEQ ID NO:5) --.

Column 66, Line 21, "[CNP37 (M32N)" should be -- [CNP37 (M32N)] --.

Column 68, Line 25, "consisting of" should be -- consisting of: --.

Column 68, Line 47, "[Gly-CNP-37 (M32N)" should be -- [Gly-CNP-37 (M32N)] --.

Column 69, Line 2, "consisting of" should be -- consisting of: --.

Signed and Sealed this
First Day of July, 2025

Coke Morgan Stewart
*Acting Director of the United States Patent and Trademark Office*